(12) United States Patent
Arora et al.

(10) Patent No.: US 12,371,461 B2
(45) Date of Patent: *Jul. 29, 2025

(54) NEMO COILED COIL MIMICS AND METHODS OF USING SAME

(71) Applicants: NEW YORK UNIVERSITY, New York, NY (US); CORNELL UNIVERSITY, Ithaca, NY (US)

(72) Inventors: Paramjit S. Arora, Cold Spring Harbor, NY (US); Ethel Cesarman, Jersey City, NJ (US); Michael G. Wuo, Brooklyn, NY (US); Jouliana Sadek, Roosevelt Island, NY (US)

(73) Assignees: NEW YORK UNIVERSITY, New York, NY (US); CORNELL UNIVERSITY, Ithaca, NY (US)

( * ) Notice: Subject to any disclaimer, the term of this patent is extended or adjusted under 35 U.S.C. 154(b) by 190 days.

This patent is subject to a terminal disclaimer.

(21) Appl. No.: 17/723,921

(22) Filed: Apr. 19, 2022

(65) Prior Publication Data

US 2022/0289802 A1 Sep. 15, 2022

Related U.S. Application Data

(63) Continuation of application No. 16/684,082, filed on Nov. 14, 2019, now Pat. No. 11,891,422.

(60) Provisional application No. 62/768,373, filed on Nov. 16, 2018.

(51) Int. Cl.
| | | |
|---|---|---|
| *A61K 39/00* | (2006.01) | |
| *A61K 47/65* | (2017.01) | |
| *A61P 35/00* | (2006.01) | |
| *C07C 49/04* | (2006.01) | |
| *C07K 7/02* | (2006.01) | |
| *C07K 7/08* | (2006.01) | |
| *C07K 14/47* | (2006.01) | |
| *A61K 38/00* | (2006.01) | |
| *A61K 45/06* | (2006.01) | |

(52) U.S. Cl.
CPC .......... *C07K 14/4702* (2013.01); *A61K 47/65* (2017.08); *A61P 35/00* (2018.01); *C07C 49/04* (2013.01); *C07K 7/02* (2013.01); *C07K 7/08* (2013.01); *A61K 38/00* (2013.01); *A61K 45/06* (2013.01)

(58) Field of Classification Search
CPC ........ C07K 14/4702; C07K 7/02; C07K 7/08; C07K 2319/00; A61K 47/65; A61K 38/00; A61K 45/06; A61K 38/04; A61K 38/16; A61K 38/10; A61P 35/00; C07C 49/04; C07D 227/02; C07D 255/02; C07D 333/02

See application file for complete search history.

(56) References Cited

U.S. PATENT DOCUMENTS

| | | | |
|---|---|---|---|
| 10,851,133 B2 | 12/2020 | Arora et al. | |
| 11,440,938 B2 | 9/2022 | Arora et al. | |
| 11,891,422 B2 * | 2/2024 | Arora .................. | C07D 227/02 |
| 2018/0162907 A1 | 6/2018 | Arora et al. | |
| 2020/0190155 A1 | 6/2020 | Arora et al. | |

FOREIGN PATENT DOCUMENTS

| | | |
|---|---|---|
| WO | 99/16883 A2 | 4/1999 |
| WO | 2016/201007 A1 | 12/2016 |

OTHER PUBLICATIONS

Del Rizzo et al., "ATP Synthase b Subunit Dimerization Domain: A Right-Handed Coiled Coil with Offset Helices," J. Mol. Biol. 364:735-46 (2006).
European Patent Application No. 16808232.9, Examination Report (Aug. 27, 2020).
Hodges, "De Novo Design of Alpha-Helical Proteins: Basic Research to Medical Applications, " Biochem. Cell Biol. 74:133-54 (1996).
Holub & Kirshenbaum, "Tricks with Clicks: Modification of Peptidomimetic Oligomers via Copper-Catalyzed Azide-Alkyne [3 + 2] Cycloaddition," Chem. Soc. Rev. 39:1325-37 (2010).
Monera et al., "Comparison of Antiparallel and Parallel Two-Stranded Alpha-Helical Coiled-Coils: Design, Synthesis, and Characterization," J. Biol. Chem. 268(26):19218-27 (1993).
Zhou et al., "Disulfide Bond Contribution to Protein Stability: Positional Effects of Substitution in the Hydrophobic Core of the Two-Stranded Alpha-Helical Coiled-Coil," Biochemistry 32:3178-87 (1993).
Examination Report for European Application No. 16808232.9 (dated May 27, 2022).
Hadley et al., "Preferred Side-Chain Constellations at Antiparallel Coiled-Coil Interfaces," PNAS 105(2):530-35 (2008).
Hadley et al., "Preferred Side-Chain Constellations at Antiparallel Coiled-Coil Interfaces," PNAS 105(2):530 (2008), Supporting Information (pp. 1-29), May 3, 2024.
Keating et al., "Side-Chain Repacking Calculations for Predicting Structures and Stabilities of Heterodimeric Coiled Coils," PNAS 98(26):14825-30 (2001).
Keating et al., "Side-Chain Repacking Calculations for Predicting Structures and Stabilities of Heterodimeric Coiled Coils," PNAS 98(26):14825 (2001), Supporting Information (pp. 1-4).

(Continued)

*Primary Examiner* — Jeanette M Lieb
(74) *Attorney, Agent, or Firm* — Troutman Pepper Locke LLP

(57) ABSTRACT

This invention relates to macrostructures (and pharmaceutical formulations containing them) that include a parallel coiled-coil structure, wherein the parallel coiled-coil comprises a first coil of Formula I and a second coil of Formula II:

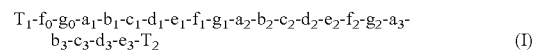

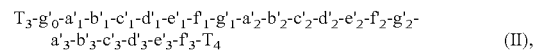

as described in the present application. Methods of using these macrostructures are also disclosed.

10 Claims, 38 Drawing Sheets

Specification includes a Sequence Listing.

(56) References Cited

OTHER PUBLICATIONS

Mason et al., "Semirational Design of Jun-Fos Coiled Coils with Increased Affinity: Universal Implications for Leucine Zipper Prediction and Design," PNAS 103(24):8989-94 (2006).
Mason et al., "Semirational Design of Jun-Fos Coiled Coils with Increased Affinity: Universal Implications for Leucine Zipper Prediction and Design," PNAS 103(24):8989-94 (2006), Supporting Information (pp. 1-7).
Oberoi et al., "Structural Basis for the Assembly of the SMRT/NCoR Core Transcriptional Repression Machinery," Nat. Struct. Mol. Biol. 18(2): 177-84 (2011) (Europe PMC Funders Author Manuscript Version).
Oberoi et al., "Structural Basis for the Assembly of the SMRT/NCoR Core Transcriptional Repression Machinery," Nat. Struct. Mol. Biol. 18(2):177 (2011), Supplementary Material (pp. 1-8).
PCT/US2016/036531, International Search Report and Written Opinion (Oct. 6, 2016).
Poster, Wuo & Arora, "An Effective Strategy for Stabilizing Minimal Coiled-Coil Mimetics," presented at Albany 2015: Conversation 19 (Jun. 9, 2015).
Poster, Wuo & Arora, "Short, Stabilized Coiled Coils as Potential Modulators of Protein-Mediated Interactions," presented at the New York Academy of Sciences (Sep. 15, 2014).
Wuo et al., "An Effective Strategy for Stabilizing Minimal Coiled Coil Mimetics," J. Am. Chem. Soc. 137:11618-21 (2015).
Wuo et al., "An Effective Strategy for Stabilizing Minimal Coiled Coil Mimetics," J. Am. Chem. Soc. 137:11618 (2015), Supporting Information (pp.S1-S23).
PCT/US2016/36531, International Preliminary Report on Patentability (Dec. 21, 2017).
U.S. Appl. No. 15/580,987, Restriction Requirement and Election of Species (Jan. 11, 2019).
U.S. Appl. No. 15/580,987, Restriction Requirement and Election of Species (Jul. 25, 2019).
U.S. Appl. No. 15/580,987, Office Action Dated Nov. 27, 2019.
European Patent Application No. 16808232.9, Supplementary European Search Report (Jan. 22, 2019).
Horne et al., "Heterocyclic Peptide Backbone Modifications in an α-Helical Coiled Coil," J. Am. Chem. Soc. 126:15366-15367 (2004).
Sun et al., "A Stable Transcription Factor Complex Nucleated by Oligomeric AML1-ETO Controls Leukaemogenesis," Nature 500:93-98 (2013).
Betts, "Amino Acid Properties and Consequences of Substitutions," Bioinformatics for Geneticists, Chapter 14, pp. 289-316 (2003).
Bagneris, "Crystal Structure of a vFlip-IKKg Complex: Insights into Viral Activation of the IKK Signalosome," Molecular Cell 30:620-631 (2008).
Watkins, "Protein-Protein Interactions Mediated by Helical Tertiary Structure Motifs," JACS 137:11622-11630 (2015).
Office Action in U.S. Appl. No. 16/684,082, mailed Jan. 19, 2022.

\* cited by examiner

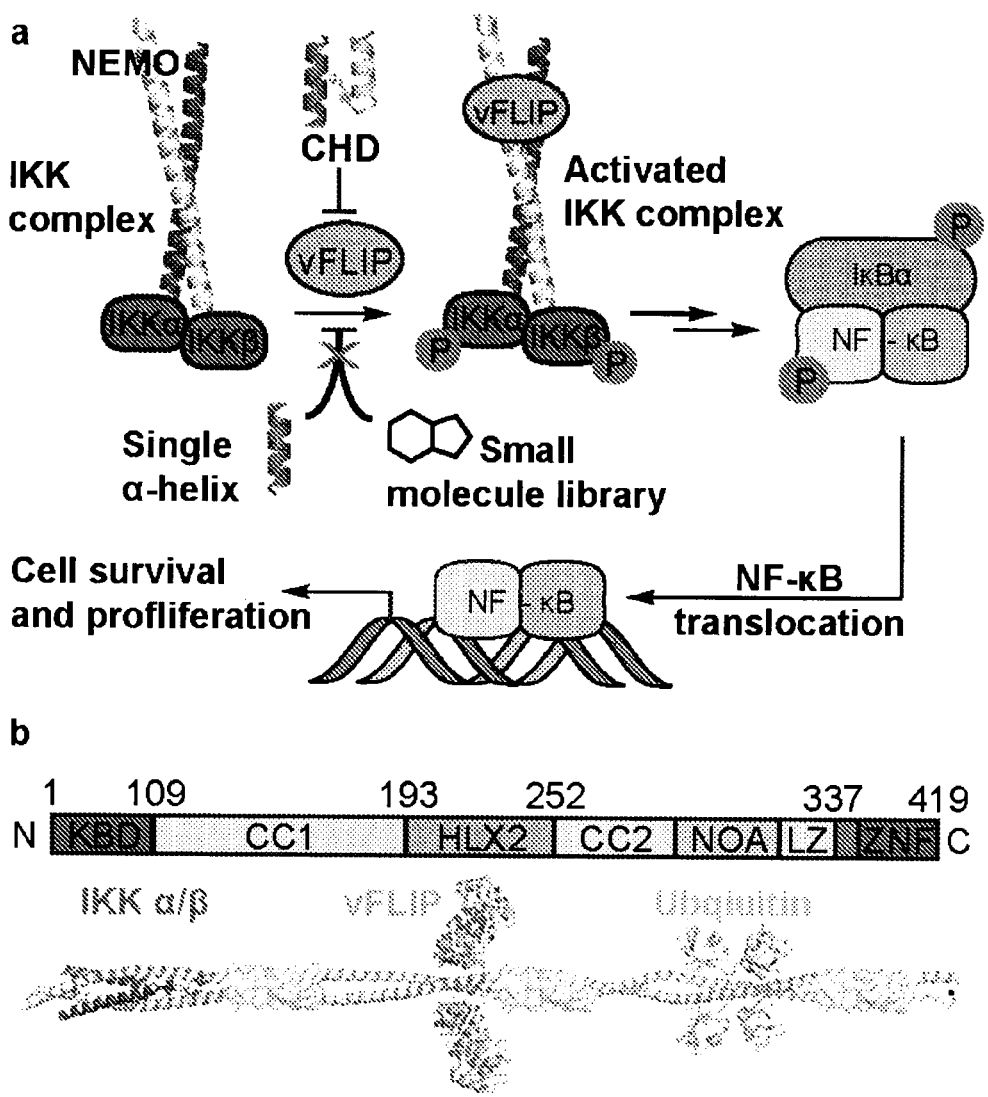
Figures 1A-B

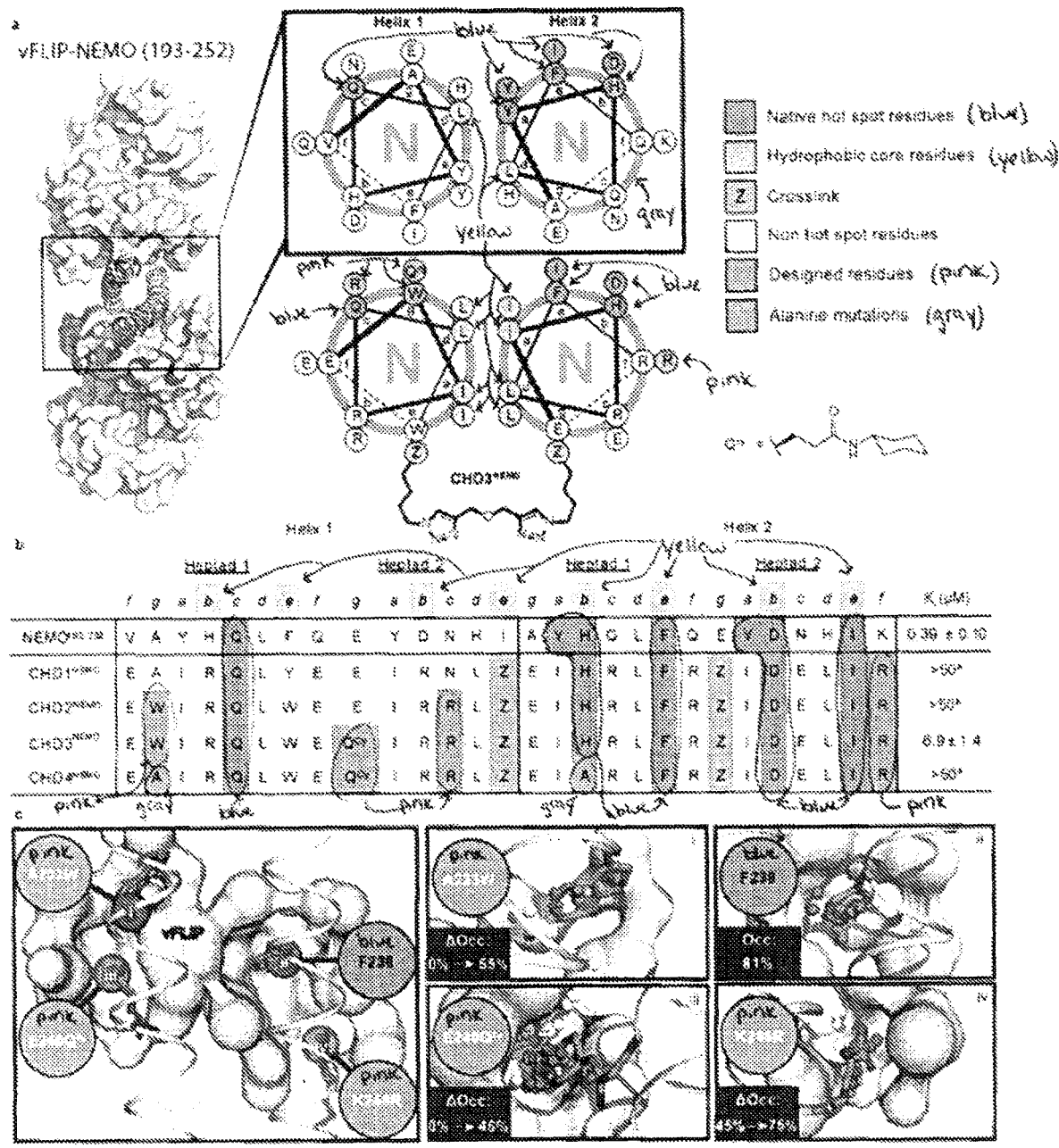
*Figures 2A-C*

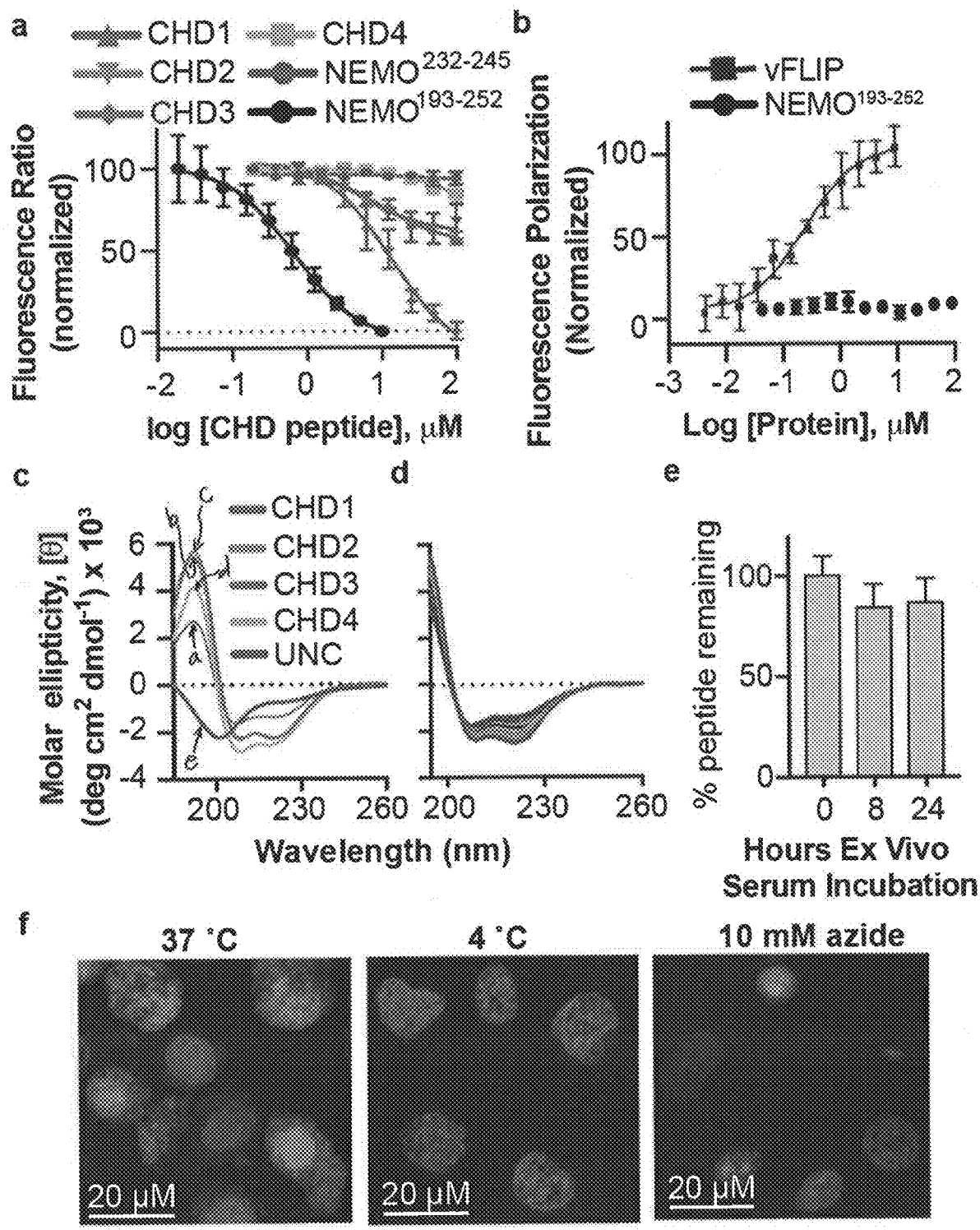
*Figures 3A–F*

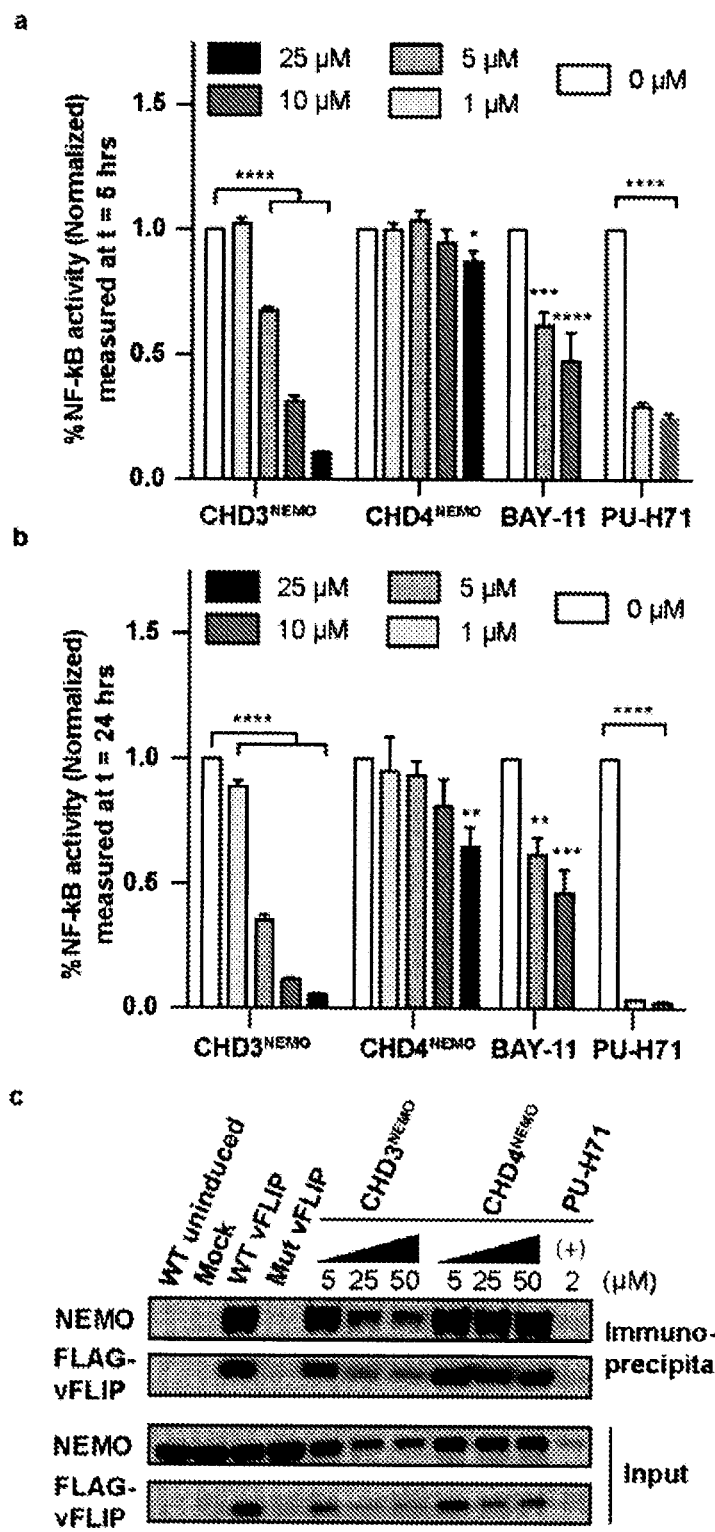
Figures 4A-C

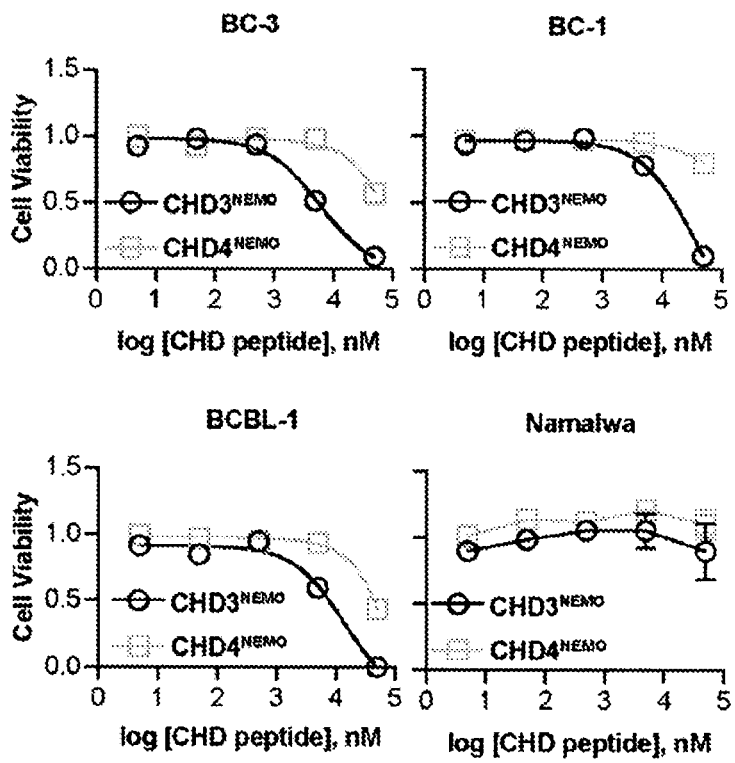
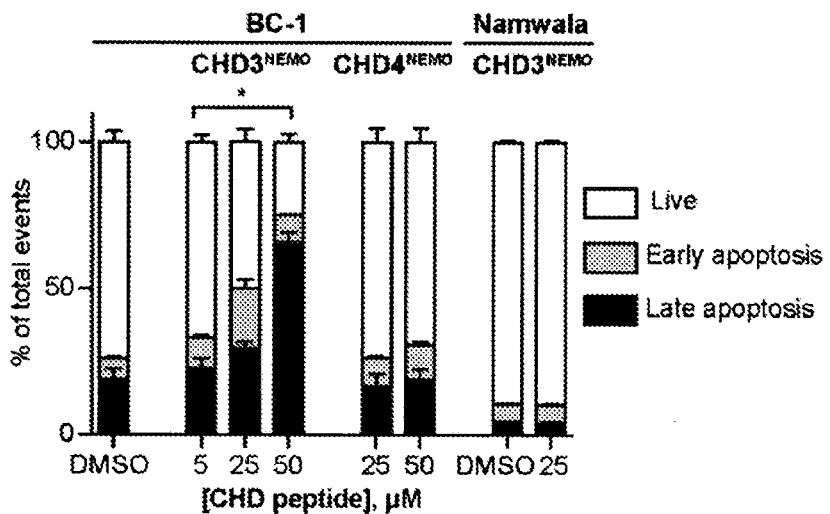
*Figures 5A-B*

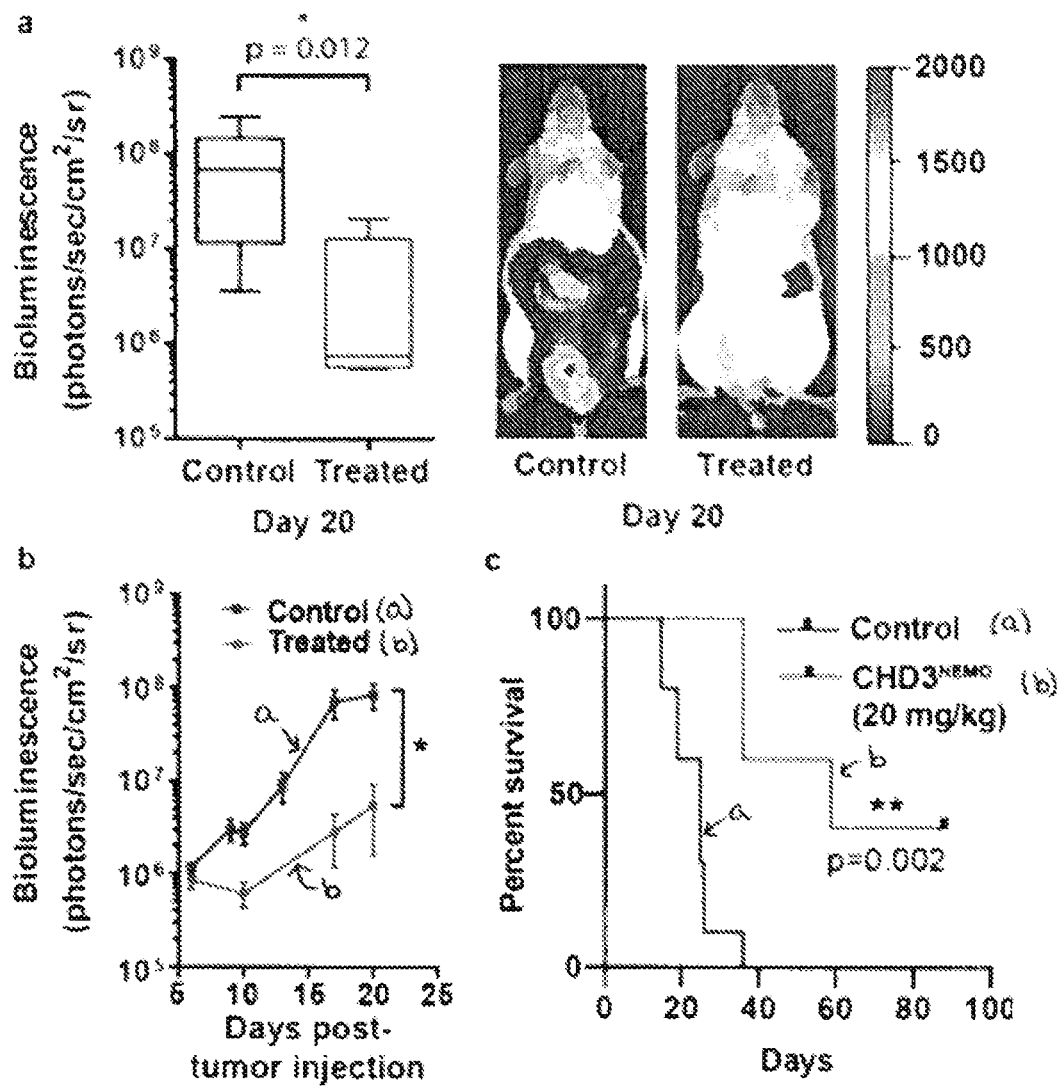
*Figure 6A-C*

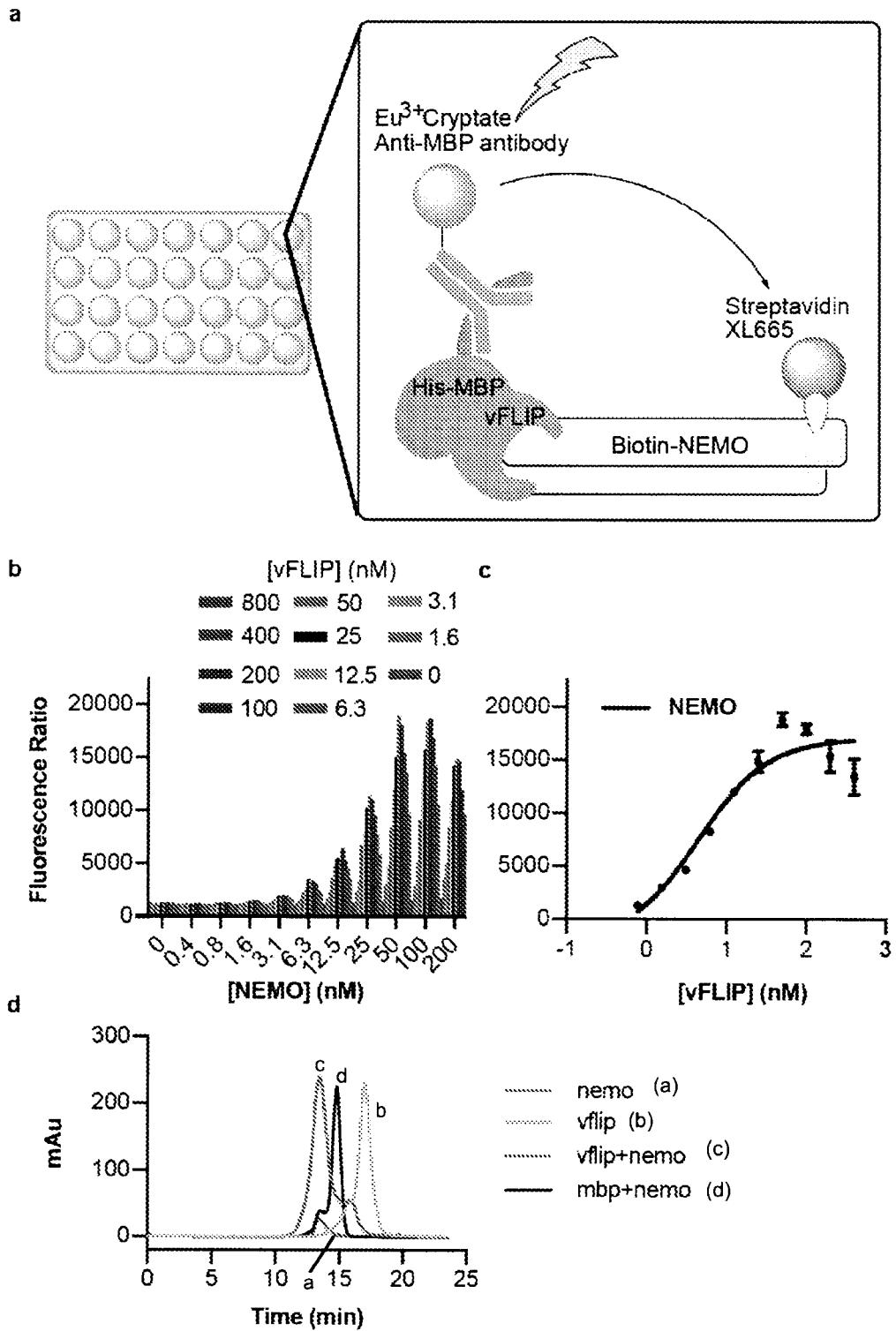
*Figures 7A-D*

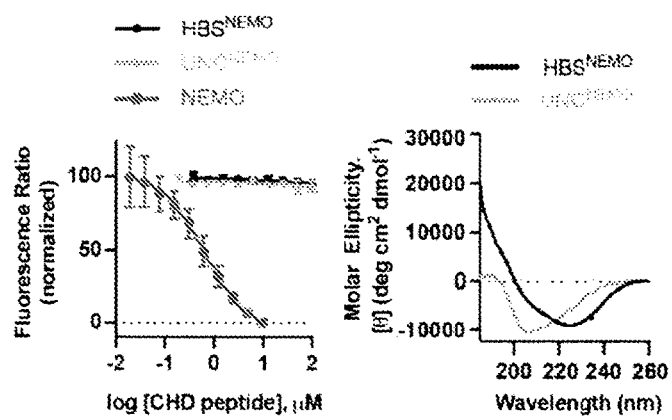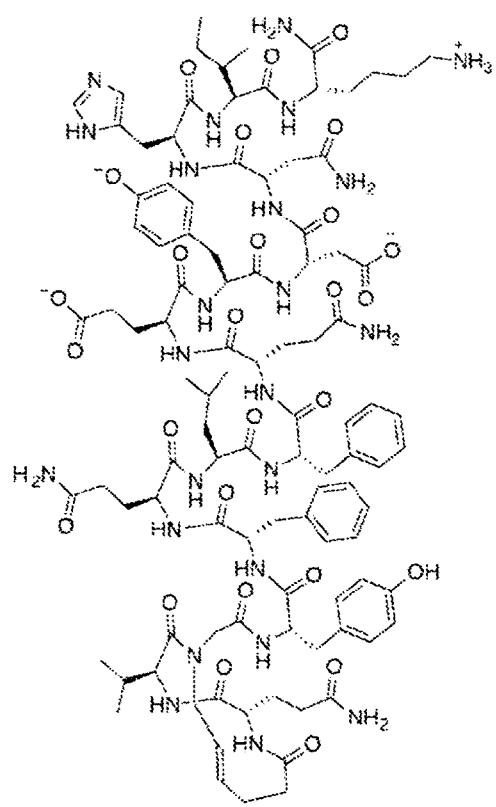
*Figures 8A-B*

Figure 15-1

Target Genes of NF-κB (*indicates that the gene has a κB site in the promoter but has not clearly been shown to be controlled by NF-κB; or the gene expression is associated with increased NF-kB activity but has not been shown to be a target directly)

Table 6A. Cytokines/Chemokines and Their Modulators

| Gene | Function | Reference | Accession No. | Human Gene Name |
|---|---|---|---|---|
| BAFF | B-cell Activating Factor | Moon & Park, 2007 | NM_006573 | TNFSF13B |
| BLIMP-1 | B lymphocyte-induced maturation protein-1 | Calame, 2008 | NM_00198 | BLIMP1/PRDM1 |
| CCL5 | T-cell secreted factor | Wickremasinghe et al, 2004 | NM_002985 | CCL5 |
| CCL15/Leukotactin/SCYA15 | Chemokine for cell attraction | Shin et al, 2005 | NM_032965 | CCL15 |
| CCL17 | Chemokine | Takegawa et al, 2008 | NM_002987 | CCL17 |
| CCL19 | Recruitment of naive T cells to dendritic cells | Pietila et al, 2007 | NM_006274 | CCL19 |
| CCL20 | Ligand of CC chemokine receptor 6 | Lee et al, 2008; Battaglia et al, 2007 | NM_004591 | CCL20 |
| CCL22 | Epithelial cell chemokine at mucosa | Nakayama et al, 2004 | NM_002990 | CCL22 |
| CCL23/SYA23 | Monocyte chemokine | Shin et al, 2007 | NM_005064 | CCL23 |
| CCL28 | Chemokine for T-cell attraction | Ogawa et al, 2004 | NM_148672 | CCL28 |
| CINC-1 | Cytokine-induced neutrophil chemoattractant | Blackwell et al, 1994; Ohtsuka et al, 1996 | NM_001511 | CXCL1 |
| *CXCL 11 | Chemokine ligand for CXCR3 | Tensen et al, 1999 | NM_005409 | CXCL11 |
| Eotaxin | beta Chemokine, eosinphil-specific | Hein et al, 1997 | NM_001565. | CXCL10 |
| Fractalkine | TNF-induced chemokine | Ahn et al, 2004;Bhavsar et al, 2008 | NP_002987 | CXCL3 |
| Gro alpha | Melanoma growth stimulating activity | Anisowicz et al, 1991 | NM_001511 | CXCL1 |
| Gro beta | Chemokine | Anisowicz et al, 1991 | AAP13104 | GRO-beta |
| Gro gamma | Chemokine | Anisowicz et al, 1991 | AAP13105. | GRO-gamma |
| Gro-1 | Growth regulated oncogene; chemokine | Wood, 1995 | NM_001511 | CXCL1 |

*Figure 15-2*

| Gene | Function | Reference | Accession No. | Human Gene Name |
|---|---|---|---|---|
| *ICOS | Inducible co-stimulator | Haaning Anderson et al. 2003 | NM_012092 | ICOS |
| IFN-g | Interferon | Sica et al. 1992; Sica et al. 1997 | NM_000619 | IFNG |
| IL-1a | Interleukin-1a | Mori & Prager, 1996 | NM_000575 | IL1A |
| IL-1b | Interleukin-1b | Hiscott et al. 1993 | NM_000576 | IL1B |
| IL-1 receptor antagonist | Inhibitor of IL-1 activity | Smith et al. 1994 | NM_173842 | IL1RN |
| IL-2 | Interleukin-2 | Serfling et al. 1989; Hoyos et al. 1989; Shimizu et al. 1995 | NM_000586 | IL2 |
| IL-6 | Interleukin-6, inflammatory cytokine | Libermann & Baltimore, 1990; Shimizu et al. 1990; Son et al. 2008 | NM_000600 | IL6 |
| IL-8 | Interleukin-8, alpha-chemokine | Kunsch & Rosen, 1993; Kang et al. 2007 | NM_000584 | IL8 |
| IL-9 | Interleukin-9 | Zhu et al. 1996; Chen et al. 2008 | NM_000590 | IL9 |
| IL-10 | Interleukin-10 | Xu & Shu, 2002; Cao et al. 2006 | NM_000572 | IL10 |
| IL-11 | Interleukin-11 | Bitko et al. 1997 | NM_000641 | IL11 |
| IL-12B (p40) | Interleukin-12 | Murphy et al. 1995 | NM_002187 | IL12B |
| IL-12A (p35) | Interleukin-12 | Homma et al. 2007 | NM_000882 | IL12A |
| IL-13 | Interleukin-13 | Hinz et al. 2002 | NM_002188 | IL13 |
| *IL-15 | Interleukin-15 | Azimi et al. 1998 | NM_172174 | IL15 |
| IL-17 | Interleukin-17 | Shen et al. 2006 | NM_002190 | IL17 |
| IL-23A (p19) | Interleukin-23 (p19 gene) | Carmody et al. 2006; Liu et al. 2007 | NM_016584 | IL23A |
| IL-27 (p28) | Interleukin-27 (p28 subunit) | Liu et al. 2007 | NM_145659 | IL27 |
| EBI3/IL-27B | EBV-induced gene 3 (IL-27beta chain) | Poleganov et al. 2008 | NM_005755 | EBI3 |
| beta-Interferon | Interferon | Hiscott et al. 1989; Lenardo et al. 1989 | NM_002176 | IFNB1 |
| IP-10 | alpha Chemokine | Ohmori & Hamilton, 1993; Yang et al. 2007 | NM_002994 | CXCL5 |
| KC | alpha Chemokine | Ohmori et al. 1995 | S79767 | KC |
| liGp1 | Cytokine | Bunting et al. 2007 | NM_021792 | ligp1 |
| | | | NM_002994 | CXCL5 |
| *LIX (mouse); ENA-78 (CXCL5) and GCP-2 (CXCL6) (human) | LPS-induced CXC chemokines | Smith et al. 2002 | NM_002993 | CXCL6 |

*Figure 15-3*

| Gene | Function | Reference | Accession No. | Human Gene Name |
|---|---|---|---|---|
| Lymphotoxin a | TNF-like cytokine | Worm et al, 1998 | NM_000595 | LTA |
| Lymphotoxin b | Anchors TNF to cell surface | Kuprash et al, 1996 | NM_002341 | LTB |
| MCP-1/JE | Macrophage chemotactic protein, beta Chemokine | Ueda et al, 1994; Ueda et al, 1997 Teferedegne et al, 2006; Xing & Remick, 2007; Ishikado et al, 2009 | NM_002982 | CCL2 |
| MIG | Monokine induced by IFN-gamma | Bunting et al, 2007 | NM_002416 | CXCL9 |
| MIP-1a,b | Macrophage inflammatory protein-1, b Chemokine | Grove & Plumb, 1993; Widmer et al, 1993 | NM_002983 | CCL3 |
|  |  |  | NM_002984 | CCL4 |
| aka (LAG-1) | Lymphocyte activation gene-1 | Xu et al, 2002; Modi et al, 2001 | NM_002984 | CCL4 |
| MIP-2 | Macrophage inflammatory protein-2, b Chemokine | Widmer et al, 1993; Lee et al, 2005 | NM_002090 | CXCL3 |
| MIP-3alpha/CCL20 | Macrophage inflammatory protein-3a | Kwon et al, 2002; Tomimori et al, 2007 | NM_004591 | CCL20 |
| *mob-1 | A C-X-C chemokine | Varley et al, 2003 | NM_001565 | CXCL10 |
| Neutrophil activating peptide-78 | Activates neutrophils | Keates et al, 2001 | NM_002994 | CXCL5 |
| RANTES | Regulated upon Activation Normal T lymphocyte Expressed and Secreted,b Chemokine | Moriuchi et al, 1997 | NM_002985 | CCL5 |
| TCA3, T-cell activation gene 3 | T-cell activation gene 3, beta chemokine | Oh & Metcalfe, 1994 | NM_002981 | CCL1 |
| TNFalpha | Tumor necrosis factor alpha | Shakhov et al, 1990; Collart et al, 1990 | NM_000594 | TNF |
| TNFbeta | Tumor necrosis factor beta | Paul et al, 1990; Messer et al, 1990 | NM_000595 | LTA |
| TRAIL (aka Apo2 ligand) | Cytokine | Baetu et al, 2001; Matsuda et al, 2005 | NM_003810 | TNFSF10 |
| TFF3 (Treefoil factor) | Peptide in response to gut irritation | Baus-Loncar et al, 2004 | NM_003226 | TFF3 |
| VEGI | Vascular endothelial growth inhibitor | Xiao et al, 2005 | NM_005118 | TNFSF15 |

Table 6B. Immunoreceptors

| Gene | Function | Reference | Accession No. | Human Gene Name |
|---|---|---|---|---|
| B7.1 (CD80) | Co-stimulation of T cells via CD28 binding | Fong et al, 1996; Zhao et al, 1996 | NM_005191 | CD80 |
| BRL-1 | B-cell homing receptor | Wolf et al, 1998 | NM_001716 | BLR1 |
| CCR5 | Chemokine receptor | Liu et al, 1998 | NM_000579 | CCR5 |

*Figure 15-4*

| Gene | Function | Reference | Accession No. | Human Gene Name |
|---|---|---|---|---|
| CCR7 | Chemokine receptor | Hopken et al, 2002 | NM_001838 | CCR7 |
| CXCR | Chemokine receptor | Maxwell et al, 2007 | NM_000634 | IL8RA |
| CXCR2 | Chemokine receptor | Maxwell et al, 2007 | NM_001557 | IL8RB |
| CD137 | TNF-like receptor | Kim et al, 2003 | NM_001561 | TNFRSF9 |
| CD154 | CD40 ligand | Srahna et al, 2001; Schubert et al, 2002; Pham et al, 2005 | NM_000074 | CD40LG |
| CD3gamma | T-cell marker | Willard-Gallo et al, 2005 | NM_000073 | CD3G |
| CD21 | B-cell surface molecule | Debnath et al, 2007 | NM_001006658 | CR2 |
| CD38 | NAD to cADP ribose converting molecule | Kang et al, 2006; Tirumurugaan et al, 2008 | NM_001775 | CD38 |
| CD40 | TNF-receptor family member | Hinz et al, 2001 | NM_001250 | CD40 |
| CD48 | Antigen of stimulated lymphocytes | Klaman & Thorley-Lawson, 1995 | NM_001778 | CD48 |
| CD83 | T-cell development molecule | McKinsey et al, 2000; Berchtold et al, 2002 | NM_004233 | CD83 |
| CD86 | Dendritic cell development molecule | Zou & Hu, 2005 | NM_175862 | CD86 |
| CD98 | Membrane receptor, survival blood cells | Yan et al, 2006 | NM_001012661 | SLC3A2 |
| CD134 | TNF-like receptor | Tone et al, 2007 | NM_003327 | TNFRSF4 |
| *F11-receptor | Ig-like receptor for platelet adhesion | Sobocki et al, 2005 | NM_016946 | F11R |
| FcRn | Neonatal receptor for IgG | Liu et al, 2007 | NM_004107 | FCGRT |
| Fc epsilon receptor II (CD23) | Receptor for IgE | Richards & Katz, 1997; Lu et al, 2006; Debnath et al, 2007 | NM_002002 | FCER2 |
| HLA-G | Human leukocyte antigen-G | Langat et al, 2007 | NM_002127 | HLA-G |
| *ICOS | T-cell activation factor | Shilling et al, 2005 | NM_012092 | ICOS |
| IL-2 receptor a-chain | IL-2 receptor subunit | Ballard et al, 1988 | NM_000417 | IL2RA |
| Immunoglobulin Cgamma1 | IgG heavy chain | Lin & Stavnezer, 1996 | J00230 | IGHG2 |
| Immunoglobulin gamma1 | IgG heavy chain | Dryer & Covey, 2005 | J00228 | IGHG1 |
| Immunoglobulin gamma4 | IgG heavy chain | Agresti & Vercelli, 2002 | K01316 | IGHG4 |
| Immunoglobulin e heavy chain | IgE heavy chain | Iciek et al, 1997 | J00222 | IGHE |
| Immunoglobulin k light chain | Antibody light chain | Sen & Baltimore, 1986 | J00241 | IGKC |
| Invariant Chain I<sub>i</sub> | Antigen presentation | Pessara & Koch, 1990 | | |
| Kinin B1 Receptor | Cardiovascular homeostasis; inflammation | Merino et al, 2005 | NM_000710 | BDKRB1 |

*Figure 15-5*

| Gene | Function | Reference | Accession No. | Human Gene Name |
|---|---|---|---|---|
| MHC class I (H-2Kb) | Major histocompatibility antigen | Israël et al, 1989a; Israël et al, 1989b | | |
| MHC Class I HLA-B7 | Major histocompatibility antigen | Johnson & Pober, 1994 | NM_005514 | HLA-B |
| b2 Microglobulin | Chaperone for MHC class I-like molecules | Israël et al, 1989a; Israël et al, 1989b; Gobin et al, 2002 | NM_004048 | B2M |
| Nod2 | Intracellular pathogen recognition | Gutierrez et al, 2002 | NM_022162 | NOD2 |
| Polymeric Ig receptor | Binds Ig | Schierven et al, 2001 | AJ276452 | pIgR |
| PGRP-S | Peptidoglycan recognition protein-S | Lang et al, 2007 | NM_005091 | PGLYRP1 |
| T-cell receptor b chain | T-cell receptor subunit | Jamieson et al, 1989; McMillan & Sikes, 2008 | NG_001333 | TCRB |
| T-cell receptor/CD3gamma | T-cell receptor subunit | Badran et al, 2002 | NM_000073 | CD3G |
| TLR-2 | Toll-like receptor | Wang et al, 2001; Johnson & Tapping, 2007 | NM_003264 | TLR2 |
| TLR9 | Toll-like receptor | Takeshita et al, 2004 | NM_017442 | TLR9 |
| *TNF-Receptor, p75/80 (CD120B) | High-affinity TNF receptor | Santee & Owen-Schaub, 1996 | NM_001066 | TNFRSF1B |
| TREM-1 | Neutrophil/monocyte Ig receptor | Zeng et al, 2007 | NM_018643 | TREM1 |

Table 6C. Proteins Involved in Antigen Presentation

| Gene | Function | Reference | Accession No. | Human Gene Name |
|---|---|---|---|---|
| Complement B | Activator of alternative complement pathway | Huang et al, 2002 | NM_001710 | CFB |
| Complement component 3 | Component of complement pathway | Moon et al, 1999 | NM_000064 | C3 |
| Complement Receptor 2 | Complement receptor for B-cell response to Ag | Tolnay et al, 2002 | NM_001006658 | CR2 |
| Proteasome Subunit LMP2 | Subunit of 26S proteasome, cysteine protease | Wright et al, 1995; Marques et al, 2004 | NM_002800 | PSMB9 |
| Peptide Transporter TAP1 | Peptide transporter for ER | Wright et al, 1995; Marques et al, 2004 | NM_000593 | TAP1 |
| Tapasin | MHC class I presentation and assembly | Herrmann et al, 2003 | NM_003190 | TAPBP |

Table 6D. Cell Adhesion Molecules

| Gene | Function | Reference | Accession No. | Human Gene Name |
|---|---|---|---|---|
| CD44 | Cell-surface receptor for hyaluronic acid | Hinz et al, 2002 | NP_000601 | CD44 |
| DC-SIGN | Dendritic cell surface C-type lectin | Liu et al, 2003 | NM_021155 | CD209 |

Figure 15-6

| Gene | Function | Reference | Accession No. | Human Gene Name |
|---|---|---|---|---|
| ELAM-1 (CD62E, E-selectin) | E-selectin, endothelial cell leukocyte adhesion molecule | Whelan et al, 1991; Schindler & Baichwal, 1994 | NM_000450 | SELE |
| Endoglin | Endothelial cell membrane glycoprotein | Botella et al, 2002 | NM_000118 | ENG |
| Fibronectin | Extracellular attachment | Lee et al, 2002; Norton et al, 2004 | NM_002026 | FN1 |
| ICAM-1 | Intercellular adhesion molecule-1 | van de Stolpe et al, 1994; Bunting et al, 2007 | NM_000201 | CD54 |
| MadCAM-1 | Mucosal addressin cell adhesion molecule | Takeuchi & Baichwal, 1995 | NM_130760 | MADCAM1 |
| NCAM | Neural cell adhesion molecule | Simpson & Morris, 2000 | NM_000615 | NCAM |
| P-selectin | Platelet adhesion receptor | Pan & McEver, 1995 | NM_003005 | SELP |
| Tenascin-C | ECM protein controls cell attachment and migration, cell growth | Mettouchi et al, 1997 | NM_002160 | TNC |
| VCAM-1 | Vascular cell adhesion molecule | Iademarco et al, 1992 | NM_001078 | VCAM1 |

Table 6E. Acute Phase Proteins

| Gene | Function | Reference | Accession No. | Human Gene Name |
|---|---|---|---|---|
| Angiotensinogen (Angiotensin II) | Angiotensin precursor, regulates blood pressure | Brasier et al, 1990; Ron et al, 1990 | NM_000029 | AGT |
| beta-defensin-2 | Anti-microbial peptide | Diamond et al, 2000; Tsutsumi-Ishii & Nagaoka, 2002; Kao et al, 2008 | AF040153 | DEFB2 |
| C4b binding protein | Complement binding protein | Moffat & Tack, 1992 | NM_000715 | C4BPA |
| Complement factor B | Complement factor | Nonaka & Huang, 1990 | NM_001710 | CFB |
| Complement factor C4 | Activates extrinsic pathway of complement activation | Yu et al, 1989 | NM_007293 | C4A |
| C-reactive protein | Host defense protein | Zhang et al, 1995; Agrawal et al, 2003a; Agrawal et al, 2003b | NM_000567 | CRP |
| Hepcidin | Acute phase protein | Liao et al, 2006 | NM_021175 | HAMP |
| Lipopolysaccharide binding protein | Binds to LPS receptor (CD14) with LPS | Schumann, 1995 | NM_004139 | LBP |
| Pentraxin PTX3 | Pentraxin | Basile et al, 1997 | NM_002852 | PTX3 |

*Figure 15-7*

| Gene | Function | Reference | Accession No. | Human Gene Name |
|---|---|---|---|---|
| Serum amyloid A proteins (SAA1, SAA2, SAA3) | Serum components | Edbrooke et al, 1991; Li & Liao, 1991; Thorn & Whitehead, 2002; Son et al, 2004 | NM_000331 | SAA1 |
| Serum amyloid A proteins (SAA1, SAA2, SAA3) | Serum components | | NM_030754 | SAA2 |
| Serum amyloid A proteins (SAA1, SAA2, SAA3) | Serum components | | S73444 | SAA3 |
| Tissue factor-1 | Activates extrinsic pathway of complement activation | Mackman et al, 1991 | NM_001993 | F3 |
| Urokinase-type plasminogen activator | Activates fibrinogen for fibrin clot lysis | Novak et al, 1991 | NM_002658 | PLAU |

Table 6F. Stress Response Genes

| Gene | Function | Reference | Accession No. | Human Gene Name |
|---|---|---|---|---|
| *CYP2E1 | Cytochrome p450 | Abdel-Razak et al, 2004 | NM_000773 | CYP2E1 |
| CYP2C11 | Cytochrome p450 | Morgan et al, 2002 | X79081 | CYP2C11 |
| CYP7b | Cytochrome p450 | Dulos et al, 2005 | NM_004820 | CYP7B1 |
| COX-2 | Cyclooxygenase, prostaglandin endoperoxide synthase | Yamamoto et al, 1995; Ackerman et al, 2008; Kaltschmidt et al, 2002 | NM_000963 | PTGS2 |
| Ferritin H chain | Iron storage protein | Kwak et al, 1995 | NM_002032 | FTH1 |
| Glutamate-cysteine ligase | GSH biosynthesis | Peng et al, 2010 | | GCLC |
| Glutamate-cysteine ligase modifier | GCLC modifier protein | Peng et al, 2010 | | GCLM |
| HSP90-alpha | Heat shock protein | Ammirante et al, 2007 | NM_001017963 | HSP90AA1 |
| *5-Lipoxygenase (guinea pig) | Arachidonic acid metabolic enzyme, leukotriene synthesis | Chopra et al, 1992 | XM_001127464 | ALOX5 |
| 12-Lipoxygenase | Arachidonic acid metabolic enzyme | Arakawa et al, 1995 | NM_000697 | ALOX12 |
| Inducible NO-Synthase | NO synthesis | Geller et al, 1993 | NM_000625 | NOS2A |
| *MAP4K1 | Activator of stress-induced protein kinase pathway | Carter et al, 2002 | NM_001042600 | MAP4K1 |
| SENP2 | SUMO-specific protease | S Miyamoto, pers commun | NC_000013.10 | SENP2 |
| Cu/Zn SOD | Superoxide dismutase | Rojo et al, 2004 | NM_000454 | SOD1 |
| SOD1 | Manganese uperoxide dismutase | Das et al, 1995 | NM_000454 | SOD1 |

*Figure 15-8*

| Gene | Function | Reference | Accession No. | Human Gene Name |
|---|---|---|---|---|
| SOD2 | Manganese superoxide dismutase | Xu et al, 1999a; 1991b; 2007a; 2007b | NM_000636 | SOD2 |
| *Mx1 | Viral resistance gene | Gerardin et al, 2004 | NM_002462 | MX1 |
| NAD(P)H quinone oxidoreductase (DT-diaphorase) | Bioreductive enzyme | Yao & O'Dwyer, 1995 | NM_000903 | NQO1 |
| Phospholipase A2 | Fatty acid metabolism | Morri et al, 1994 | AF058921 | PLA2 |
| SEPS1 | Involved in cytokine production | Gao et al, 2006 | NM_018445 | SELS |

Table 6G. Cell-Surface Receptors

| Gene | Function | Reference | Accession No. | Human Gene Name |
|---|---|---|---|---|
| ABCA1 | ATP-binding cassette transporter | Gerbod-Giannone et al, 2006 | NM_005502 | ABCA1 |
| ABCC6 | ATP-binding, multidrug resistance-associated protein 6 transporter | Jiang et al, 2005 | NM_001171 | ABCC6 |
| A1 adenosine receptor | Pleiotropic physiological effects | Nie et al, 1998; Jhaveri et al, 2007 | NM_000674 | ADORA1 |
| A2A | Adenosine receptor | Morello et al, 2006 | NM_000675 | ADORA2A |
| *ADAM19 | Dendritic cell marker | Ehrnsperger et al, 2005 | NM_023038 | ADAM19 |
| Amiloride-sensitive sodium channel | Sodium channel | Baines et al, 2002; Haddad, 2005 | NM_001038 | SCNN1A |
| *alpha2B-adrenergic receptor | adrenergic receptor | Cayla et al, 2004 | NM_000682 | ADRA2B |
| Bradykinin B1-Receptor | Pleiotropic physiological effects | Ni et al, 1998 | NM_000710 | BDKRB1 |
| *CD23 | Cell-surface molecule | Tinnell et al, 1998 | NM_002002 | FCER2/CD23 |
| CD69 | Lectin mainly on activated T cells | Lopez-Cabrera et al, 1995 | NM_001781 | C69 |
| DOR | Delta opiod receptor | Chen et al, 2005, 2006 | NM_000911 | OPRD1 |
| Epidermal Growth Factor Receptor | Receptor for EGF | Nishi et al, 2003; Thornburg & Raab-Traub, 2007 | NM_005228 | EGFR |
| ErbB2 | EGF-like receptor | Kitamura et al, 2005 | NM_001005862 | ERBB2 |
| Gal1 Receptor | Galanin receptor, neuroendocrine peptide | Lorimer et al, 1997 | NM_002256 | KISS1 |
| Lox-1 | Receptor for Oxidized low density lipoprotein | Nagase et al, 1998 | NM_002543 | OLR1 |
| Ly49 | Receptor on NK cells | Pascal et al, 2007 | NM_006611 | KLRA1 |
| Mdr1 | Multiple drug resistance mediator (P-) | Zhou & Kuo, 1997; Wang et al, 2007 | NM_018849 | ABCB4 |

*Figure 15-9*

| Gene | Function | Reference | Accession No. | Human Gene Name |
|---|---|---|---|---|
| Mu-opioid receptor | Opioid Receptor (glycoprotein) | Kraus et al, 2003 | EU360599 | OPRM1 |
| mGlu2 | Metabotropic glutamate receptor 2 | Chiechio et al, 2006 | NM_000839 | GRM2 |
| Neuropeptide Y-Y1 receptor | Pleiotropic physiological effects | Musso et al, 1997 | NM_000909 | NPY1R |
| *NMDA receptor subunit 2A (rat) | Neural receptor for N-methyl-D-aspartate | Richter et al, 2002 | NM_000833 | GRIN2A |
| *NMDA receptor subunit NR-1 (GRIN1 gene) | Subunit of neural receptor for N-methyl-D-aspartate | Begni et al, 2003 | NM_021569 | GRIN1 |
| Oxytocin receptor | Oxytocin receptor | Terizidou et al, 2006 | NM_000916 | OXTR |
| PAF receptor 1 | Platelet activator receptor | Mutoh et al, 1994 | NM_000952 | PTAFR |
| P-gp | P-glycoprotein-Drug resistance | Wang et al, 2007 | NM_000927 | ABCB1 |
| RAGE- receptor for advanced glycation end products | Receptor for Advanced Glycation End products | Li & Schmidt, 1997 | NM_001136 | AGER |

Table 6H. Regulators of Apoptosis

| Gene | Function | Reference | Accession No. | Human Gene Name |
|---|---|---|---|---|
| ASC | Apoptosis-associated speck-like protein containing a CARD | Sun et al, 2007 | NM_013258 | PYCARD |
| Bax | Pro-apoptotic Bcl-2 homologue | Grimm et al, 2004 | NM_004324 | BAX |
| Bfl1/A1 | Pro-survival Bcl-2 homologue | Grumont et al, 1999; Zong et al, 1999 | NM_004049 | BCL2A1 |
| Bcl-xL | Pro-survival Bcl-2 homologue | Chen et al, 1999; Lee et al, 1999 | NM_138578 | BCL2L1 |
| Bcl-2 | Pro-survival factor | Catz & Johnson, 2001 | NM_000633 | BCL2 |
| Bim | Pro-apoptotic Bcl-2 homolog | Wang et al, 2008 | NM_138621 | BCL2L11 |
| B7-H1 | Programmed cell death ligand 1 | Lee et al, 2005 | NM_014143 | CD274 |
| BNIP3 | Hypoxia-inducible death factor | Baetz et al, 2005; Shaw et al, 2006 | NM_004052 | BNIP3 |
| Caspase-11 | Caspase | Schauvliege et al, 2002 | NM_001225 | CASP4 |
| Nr13 | Pro-survival Bcl-2 homologue | Lee et al, 1999 | | |
| c-FLIP | Pro-survival factor | Kreuz et al, 2001 | NM_003879 | CFLAR |
| CD95 (Fas) | Pro-apoptotic receptor | Chan et al, 1999; Zhou et al, 2005; Singh et al, 2006 | NM_000043 | FAS |

*Figure 15-10*

| Gene | Function | Reference | Accession No. | Human Gene Name |
|---|---|---|---|---|
| CIDEA | Cell death-inducing DFFA-like effector A | Pettersson et al, 2008 | NP 001270.1; NP 938031.1 | CIDEA |
| *Fas-associated phosphatase-1 | Protein phosphatase | Irie et al, 2001 | NM 006264 | PTPN13 |
| Fas-Ligand | Inducer of apoptosis | Matsui et al, 1998; Singh et al, 2006 | NM 000639 | FASLG |
| IAPs | Inhibitors of Apoptosis | You et al, 1997; Stehlik et al, 1998a, 1998b | | |
| IEX-1L | Immediate early gene | Wu et al, 1998 | NM 052815 | IER3 |
| TRAF-1 | TNF-receptor associated factor | Schwenzer et al, 1999 | NM 005658 | TRAF1 |
| TRAF-2 | TNF-receptor associated factor | Wang et al, 1998 | NM 021138 | TRAF2 |
| *TRAF-2 binding protein (Carp) | TRAF2 binding protein | Chang et al, 2005 | NM 052864 | TIFA |
| XIAP | X-linked inhibitor of apoptosis | Turner et al, 2007 | NM 001167 | XIAP |

Table 6I. Growth Factors, Ligands, and Their Modulators

| Gene | Function | Reference | Accession No. | Human Gene Name |
|---|---|---|---|---|
| Activin A | TGF-beta-like factor | Alexander et al, 2007 | NM 002192 | INHBA |
| Angiopoietin | Tie-2 receptor ligand | Scott et al, 2005 | NM 001146 | ANGPT1 |
| BCAP | B-cell Adaptor for Phosphoinositide 3-kinase | Gupta et al, 2008 | NM 152309 | PI3KAP1 |
| BDNF | Brain-derived neurotrophic factor | Saha et al, 2007 | NM 001709 | BDNF |
| BLyS | B-lymphocyte stimulator | Fu et al, 2006 | NM 006573 | TNFSF13B |
| BLNK | B-cell linker | Gupta et al, 2008 | NM 013314 | BLNK |
| BMP-2 | Bone Morphogenic Protein-2 | Feng et al, 2003; Fukui et al, 2006 | NM 001200 | BMP2 |
| BMP-4 | Bone Morphogenic Protein-4 | Zhu et al, 2007 | NM 001202 | BMP4 |
| CGRP | Calcitonin gene-related peptide | Bowen et al, 2005 | NM 000728 | CALCB |
| FGF8 | Fibroblast Growth Factor 8 | Armstrong et al, 2006 | NM 006119 | FGF8 |
| FLRG | Follistatin-related gene | Bartholin et al, 2007 | NM 005860 | FSTL3 |
| G-CSF | Granulocyte Colony Stimulating Factor | Nishizawa & Nagata, 1990 | NM 000759 | CSF3 |
| GM-CSF | Granulocyte Macrophage Colony Stimulating Factor | Schreck & Baeuerle, 1990; Bunting et al, 2007 | NM 000758 | CSF2 |
| *HGF/SF | Hepatocyte growth factor/scatter factor | Harrison & Farzaneh, 2000 | NM 000601 | HGF |
| EPO | Erythropoietin | Figueroa et al, 2002 | NM 000799 | EPO |
| *IGFBP-1 | Insulin-like growth factor binding protein-1 | Lang et al, 1999 | NM 001013029 | IGFBP1 |

*Figure 15-11*

| Gene | Function | Reference | Accession No. | Human Gene Name |
|---|---|---|---|---|
| IGFBP-2 | Insulin-like growth factor binding protein-2 | Cazals et al, 1999 | NM_000597 | IGFBP2 |
| M-CSF (CSF-1) | Macrophage Colony Stimulating Factor | Brach et al, 1991; Hohensinner et al, 2007 | NM_000757 | CSF1 |
| Midkine (neurite growth promoting factor-2) | Heparin Binding Growth Factor | You et al, 2008 | NM_001012334 | MDK |
| NGF | Nerve Growth Factor | Heese et al, 2006 | NM_002506 | NGFB |
| NK-1R | Neurokinin-1 Receptor | Simeonidis et al, 2003; Ramkissoon et al, 2007 | NM_015727 | TACR1 |
| NK4 | Hepatocyte growth factor | Zhou et al, 2003 | NM_001012635 | NK4 |
| Nrg1 | Neuregulin | Frensing et al, 2007 | NM_004495 | NRG1 |
| OPN | Osteopontin | Samant et al, 2007 | NM_001040058 | SPP1 |
| PDGF B chain | Platelet-derived Growth Factor | Khachigian et al, 1995; Au et al, 2005 | NM_002608 | PDGFB |
| PIGF | Placenta Growth Factor | Cramer et al, 2005 | NM_002643 | PIGF |
| Proenkephalin | Hormone | Rattner et al, 1991 | NM_006211 | PENK |
| Prolactin | Pituitary hormone | Friedrichsen et al, 2005 | NM_000948 | PRL |
| Stem Cell Factor | Mast Cell Growth Factor | Da Silva et al, 2003; 2004 | NM_000899 | KITLG |
| *Thrombospondin-1 (TSP-1) | Matrix glycoprotein t | Yang et al, 2003 | NM_003246 | THBS1 |
| *Thrombospondin-2 (THBS2) | Matrix glycoprotein t | Adolph et al, 1997 | NM_003247 | THBS2 |
| VEGF C | Vascular Endothelial Growth Factor | Chilov et al, 1997 | NM_005429 | VEGFC |
| *WNT10B | Secreted glycoprotein | Katoh & Katoh, 2007 | NM_003394 | WNT10B |

Table 6J. Early Response Genes

| Gene | Function | Reference | Accession No. | Human Gene Name |
|---|---|---|---|---|
| *B94 | Early response gene | Zhou et al, 2003 | NM_006291 | TNFAIP2 |
| *Egr-1 | Mitogen-induced early response gene; zinc finger | Zhou et al, 2003 | NM_001964 | EGR1 |
| p22/PRG1 | Rat homologue of IEX | Schafer et al, 1998 | NM_052815 | IER3 |
| *p62 | Non-proteasomal multi-ubiquitin chain binding protein | Vadlamudi & Shin, 1998 | NM_016221 | DCTN4 |
| *TIEG | TGF-b early response gene; zinc finger protein | Zhou et al, 2003 | NM_001032282 | KLF10 |

Figure 15-12

Table 6K. Transcription Factors and Their Modulators

| Gene | Function | Reference | Accession No. | Human Gene Name |
|---|---|---|---|---|
| A20 | TNF-inducible zinc finger | Krikos et al, 1992 | NM_006290 | TNFAIP3 |
| ABIN-3 | NF-kB inhibitor | Verstrepen et al, 2007 | NM_024873 | TNIP3 |
| Androgen receptor | Hormone receptor | Zhang et al, 2004 | NM_000044 | AR |
| Bcl-3 | Coactivator for NF-kB p50 and p52 | Brocke-Heidrich et al, 2006 | NM_005178 | BCL3 |
| BMI-1 | Polycomb chromatin modifier | Dutton et al, 2006 | NM_005180 | BMI1 |
| CDX1 | Homeobox protein | Wong et al, 2005 | NM_001804 | CDX1 |
| *c-fos (fish gene) | Proto-oncogene | Li et al, 2004 | NM_005252 | FOS |
| c-myb | Proto-oncogene | Toth et al, 1995 | NM_005375 | MYB |
| c-myc | Proto-oncogene | Duyao et al, 1990 | NM_002467 | MYC |
| c-rel | Proto-oncogene | Hannink & Temin, 1990; Capobianco & Gilmore, 1991 | NM_002908 | REL |
| C/EBPdelta | Transcription factor | Liu et al, 2007 | NM_005195 | CEBPD |
| *DC-SCRIPT | Dendritic cell zinc finger protein | Triantis et al, 2006 | NM_152625 | ZNF366 |
| Dmp1 | Myb-like transcription factor | Taneja et al, 2007 | NM_001079911 | DMP1 |
| E2F3a | Cell cycle regulator | Cheng et al, 2003 | NM_001949 | E2F3 |
| Elf3 | Ets family transcription factor | Hou et al, 2004 | NM_004433 | ELF3 |
| *ELYS | Embryonic large molecule derived from yolk sac | Okita et al, 2003 | NM_015446 | AHCTF1 |
| *ETR101 | TPA-inducible, Jun-like transcription factor | Zhou et al, 2003 | NM_004907 | IER2 |
| Gata-3 | T-cell differentiation Factor | Corn et al, 2005 | NM_001002295 | GATA3 |
| *Glucocorticoid receptor | Promoter 1B of the GR | Schaff & Cidlowski, 2002 | NM_000176 | NR3C1 |
| HIF-1alpha | Hypoxia-inducible factor | Bonello et al, 2007; Belaiba et al, 2007; van Uden et al, 2008; Gorlach & Bonello, 2008 | NM_001530 | HIF1A |
| HOXA9 | Homeobox protein | Trivedi et al, 2007 | NM_152739 | HOXA9 |
| IRF-1 | Interferon regulatory factor-1 | Harada et al, 1994; Robinson et al, 2006 | NM_002198 | IRF1 |
| IRF-2 | Interferon regulatory factor-2 | Harada et al, 1994 | NM_002199 | IRF2 |
| IRF-4 | Interferon regulatory factor-4 | Grumont & Gerondakis, 2000; Saito et al, 2007 | NM_002460 | IRF4 |
| IRF-7 | Interferon regulatory factor -7 | Lu et al, 2002 | NM_001572 | IRF7 |

Figure 15-13

| Gene | Function | Reference | Accession No. | Human Gene Name |
|---|---|---|---|---|
| IkB-a | Inhibitor of Rel/NF-kB | Haskill et al, 1991; Sun et al, 1993; de Martin et al, 1993 | NM_020529 | NFKBIA |
| IkB-e | Inhibitor of Rel/NF-kB | Tian et al, 2005 | NM_004556 | NFKBIE |
| junB | Proto-oncogene | Brown et al, 1995 | NM_002229 | JUNB |
| jmjD3 | Histone lysine demethylase | G Natoli, pers comm | XM_043272 | JMJD3 |
| Lef1 | Transcription factor in Wnt/b-catenin pathway | Yun et al, 2007 | NM_016269 | LEF1 |
| LZIP | Leukocyte cell mobility | Jang et al, 2007 | NM_006368 | CREB3 |
| Mail | IkB-like protein | Shiina et al, 2001; Ito et al, 2004 | NM_001005474 | NFKBIZ |
| nfkb2 | NF-kB p100 precursor | Lombardi et al, 1995 | NM_001077493 | NFKB2 |
| nfkb1 | NF-kB p105 precursor | Ten et al, 1992 | NM_003998 | NFKB1 |
| NLRP2 | NF-kB pathway inhibitor | Fontalba et al, 2007 | NM_017852 | NLRP2 |
| NURR1 | Nuclear orphan receptor | McEvoy et al, 2002 | NM_006186 | NR4A2 |
| Osterix | Bone transcription factor | Lu et al, 2006 | AF477981 | Osterix |
| p53 | TF, Tumor suppressor | Wu & Lozano, 1994; Schumm et al, 2006 | NM_000546 | TP53 |
| Progesterone receptor | Transcription factor | Condon et al, 2005 | NM_000926 | PGR |
| PU.1 | Transcription factor | Bonadies et al, 2009 | NM_001080547.1 | SPI1 |
| relb | Transcription factor | Bren et al, 2001 | NM_006509 | RELB |
| Snail | Transcription repressor | Barbera et al, 2004; Julien et al, 2007 | NM_005985 | SNAI1 |
| Sox9 | Transcription factor | Murakami et al, 2000 | NM_000346 | SOX9 |
| Stat5a | Transcription factor | Hinz et al, 2002 | NM_003152 | STAT5A |
| Tfec | Transcription factor | Rehli et al, 2005 | NM_001018058 | TFEC |
| Twist | Transcription repressor | Horikawa et al, 2007; Pham et al, 2007 | NM_000474 | TWIST1 |
| WT1 | Zinc finger transcription factor | Dehbi et al, 1998; Chen & Williams, 2000 | NM_000378 | WT1 |
| YY1 | Transcription factor | Wang et al, 2007 | NM_003403 | YY1 |

*Figure 15-14*

Table 6L. Enzymes

| Gene | Function | Reference | Accession No. | Human Gene Name |
|---|---|---|---|---|
| *ABC Transporters | ATP-binding membrane transporters | Mutch et al, 2003 | NM_019625 | ABCB9 |
| *N-acetylglucosaminyltransferase I (rat gene) | N-acetylglucosaminyltransferase | Fukuda et al, 2003 | NM_001097634 | GCNT1 |
| ADH | Liver alcohol dehydrogenase | Potter et al, 2002 | NM_000667 | ADH1A |
| AID | Activation-induced cytidine deaminase | Gourzi et al, 2007; Endo et al, 2007 | NM_020661 | AICDA |
| AMACR | alpha-methylacyl-CoA racemase | Chen et al, 2007 | NM_014324 | AMACR |
| ARF-related protein-1 | GTPase | Mueller et al, 2007 | NM_003224 | ARFRP1 |
| Argininosuccinate synthetase | Arginine synthesis | Fan et al, 2005; Brasse-Lagnel et al, 2007 | NM_000050 | ASS1 |
| Aromatase (promoter II) | Estrogen synthesis | Brasse-Lagnel et al, 2004 | NM_000103 | CYP19A1 |
| ART2.1 | Ecto-ADP-ribosyltransferase | Hong et al, 2007 | NM_004314 | ART1 |
| alpha 1ACT | Anti-chymotrypsin | Kiss et al, 2005 | NM_001085 | SERPINA3 |
| BACE-1 | beta site APP cleaving enzyme | Sambamurti et al, 2004; Rossner et al, 2006; Bourne et al, 2007; Bruggia-Prevot et al, 2008 | NM_012104 | BACE1 |
| Btk | Bruton's Tyrosine kinase | Yu et al, 2008 | NM_000061 | BTK |
| Cathepsin B | Lysosomal cysteine protease | Bien et al, 2004 | NM_001908 | CTSB |
| *Cathepsin L | Lysosomal cysteine protease | Seth et al, 2003 | NM_001912 | CTSL1 |
| cdk6 | Cell-dependent kinase 6 | Iwanaga et al, 2008 | | CDK6 |
| *Ceramide glycosyltransferase | Glycosphingolipid | Ichikawa et al, 1998 | NM_020120 | UGCGL1 |
| Chitinase 3-like protein | Chitinase | Recklies et al, 2005 | NM_001276 | CHI3L1 |
| *cis-retinoid/androgen dehydrogenase type 1 (CRAD1) | Short chain dehydrogenase | Chai et al, 2001 | NM_080436 | Rdh1 |
| *cis-retinoid/androgen dehydrogenase type 2 (CRAD2) | Short chain dehydrogenase | Tomita et al, 2000 | NM_017473 | Rdh7 |
| Collagenase 1 | Matrix metalloproteinase | Vincenti et al, 1998 | NM_002421 | MMP1 |
| *Dihydrodiol dehydrogenase | Oxidoreductase, oxidation of trans-hydodiols | Ciaccio et al, 1996 | NM_00135 | AKR1C1 |
| *DYPD | Dihydropyrimidine dehydrogenase | Ukon et al, 2005 | NM_000110 | DPYD |
| DNASIL2 | DNAse-like endonuclease | Shiokawa et al, 2004 | NM_001374 | DNASE1L2 |

*Figure 15-15*

| Gene | Function | Reference | Accession No. | Human Gene Name |
|---|---|---|---|---|
| EL | Endothelial lipase | Kempe et al, 2005 | NM_006033 | LIPG |
| *ENO2 | Enolase 2 gamma | Carter et al, 2002 | NM_001975 | ENO2 |
| *GAD67 | Glutamic acid decarboxylase | Szabo et al, 1996 | NM_000817 | GAD1 |
| GD3-synthase | Sialyltransferase | Zeng et al, 1998; Kang et al, 2007 | NM_003034 | ST8SIA1 |
| gp91 phox | Subunit of NADPH oxidase | Anrather et al, 2006 | NM_007052 | NOX1 |
| Gelatinase B | Matrix metalloproteinase | He, 1996 | NM_004994 | MMP9 |
| GSTP1-1 | Glutathione S-transferase | Xia et al, 1996 | NM_000852 | GSTP1 |
| Glutamate-cysteine ligase | Glutathione S-transferase synthesis enzyme | Yang et al, 2001; Nagashima et al, 2007 | NM_001498 | GCLC |
| GCLC | Glutamate-cysteine ligase catalytic subunit | Yang et al, 2005 | NM_002061 | GCLM |
| *Glutamate-cysteine ligase modifier | Glutathione S-transferase synthesis enzyme | Yang et al, 2001 | NM_001498 | GCLC |
| *gamma glutamylcysteine synthetase | Glutatamylcysteine synthesis | Cheng et al, 2005 | NM_001498 | GCLC |
| *Glucose l-6-phosphate dehydrogenase | Hexose monophosphate | Garcia-Nogales et al, 1999 | NM_000402 | G6PD |
| Glucose-6-phosphatase | Hexose phosphatase | Xu et al, 2007 | NM_000151 | G6PC |
| GnRH II | Gonadotropin-releasing hormone II | Hoo et al, 2007 | NM_001501 | GNRH2 |
| Granzyme B | NK cell cytotoxicity | Huang et al, 2006 | NM_004131 | GZMB |
| *Soluble Guanylyl cyclase alpha (1) | Receptor for NO | Vazquez-Padron et al, 2004 | NM_000855 | GUCY1A2 |
| *Heparanase | Cleaves heparin | Cao et al, 2005 | NM_006665 | HPSE |
| HO-1 | Hemeoxygenase | Lavrovsky et al, 1994; Rushworth & O'Connell, 2004; Wu et al, 2004; Lin et al, 2007 | NM_002133 | HMOX1 |
| Hyaluronan synthase | Synthesizes hyaluronic acid | Ohkawa et al, 1999; Kim, 2006; Saavalainen et al, 2007 | NM_001523 | HAS1 |
| 11bHSD2 | 11beta-hydroxysteroid dehydrogenase type 2 | Kostadinova et al, 2005 | NM_000196 | HSD11B2 |
| *17bHSD | 17beta-hydroxysteroid dehydrogenase | Villar et al, 2007 | NM_014234 | HSD17B8 |
| H+-K+ATPase alpha2 | Role in potassium homeostasis | Zhang & Kone, 2002; Saha et al, 2008 | NM_000702 | ATP1A2 |
| Iodothyronine deiodinase (type 2) | Converts T4 to T3 | Fekete et al, 2003; Zeold et al, 2006 | NM_000793 | DIO2 |

Figure 15-16

| Gene | Function | Reference | Accession No. | Human Gene Name |
|---|---|---|---|---|
| *Indoleamine 2,3-dioxygenase | Enzyme for Trp synthesis | Ogasawara et al, 2009 | NM_002164 | IDO1 |
| Lipocalin-type prostaglandin D synthase (L-PGDS) | Prostaglandin D2 synthase in brain | Fujimori et al, 2003 | NM_000954 | PTGDS |
| Lysozyme | Hydrolyzes bacterial cell walls | Phi van, 1996 | NM_000239 | LYZ |
| Mthfr | Methylenetetrahydrofolate reductase | Pickell et al, 2005 | NM_005957 | MTHFR |
| *MKP-1 | MAP kinase phosphatase | Zhou et al, 2003 | NM_004417 | DUSP1 |
| MMP-3, matrix metalloproteinaase-3 | Secreted collagenase involved in metastasis | Borghaei et al, 2004 | NM_002422 | MMP3 |
| MMP-9, matrix metalloproteinaase-9 | Secreted collagenase involved in metastasis | Bond et al, 1998; Farina et al, 1999; Yan et al, 2004 | NM_004994 | MMP9 |
| MLCK | (Long) Myosin light chain kinase | Graham et al, 2006 | NM_053025 | MYLK |
| iNOS | Inducible nitric oxide synthase | Morris et al, 2003; Guo et al, 2006; Hughes et al, 2008 | NM_000625 | NOS2A |
| n-NOS | Neuronal nitric oxide synthase | Nakata et al, 2006; Li et al, 2007a, 2007b | NM_000620 | NOS1 |
| *PDE7A1 | Phosphodiesterase 7A1 | Torras-Llort, & Azorin, 2003 | NM_002603 | PDE7A |
| PIM-1 | Ser/Thr kinase | Zhu et al, 2002 | NM_002648 | PIM1 |
| Plk3 | Polo-like (Ser/Thr) kinase 3 | Li et al, 2005 | NM_004073 | PLK3 |
| PIK3CA | Phosphatidylinositol 3-kinase catalytic subunit | Yang et al, 2008 | NM_006218 | PIK3CA |
| *PP5 | Protein phosphatase 5 | Matsuda et al, 2003 | NM_006247 | PPP5C |
| PKAalpha | Protein kinase A isoform | Kaltschmidt et al, 2006 | NM_002730 | PRKACA |
| PKCdelta | Protein kinase D isoform | Suh et al, 2003 | NM_006254 | PRKCD |
| PLCdelta 1 | Phospholipase C isoform | Kim et al, 2003 | NM_006225 | PLCD1 |
| *PTGIS, prostaglandin synthase | Prostaglandin synthase | Yokoyama et al, 1996 | NM_000961 | PTGIS |
| *PGES, prostaglandin E synthase | Prostaglandin synthase | Zhou et al, 2003 | NM_004878 | PTGES |
| PTP1B | Protein tyrosine phosphatase 1B | Zabolotny et al, 2008 | NM_002827 | PTPN1 |
| PTHrP | Parathyroid hormone related protein | Nadella et al, 2007 | NM_002820 | PTHLH |
| RACK1 | Receptor for Activated C kinase | Choi et al, 2003 | NM_006098 | GNB2L1 |
| *REV3 | DNA polymerase zeta | Yu et al, 2004 | NM_002912 | REV3L |
| Slfn-2 | Schlafen-2 DNA/RNA helicase | Sohn et al, 2007 | NM_011408 | Slfn2 |
| Serpin 2A | Serine protease | Hampson et al, 2001 | XM_372532 | SERPINA2 |

*Figure 15-17*

| Gene | Function | Reference | Accession No. | Human Gene Name |
|---|---|---|---|---|
| SIAT1 | Sialyltransferase | Lo & Lau, 1999 | NM_173216 | ST6GAL1 |
| SNARK | SNF1/AMPK-related kinase | Legembre et al, 2004 | NM_030952 | NUAK2 |
| SSAT | Spermidine/spermine N1-acetyltransferase | Babbar et al, 2006 | NM_002970 | SAT1 |
| *SUV3 | ATP-dependent RNA and DNA helicase | Minczuk et al, 2005 | NM_003171 | SUPV3L1 |
| TERT | Telomerase catalytic subunit | Yin et al, 2000; Hrdlickova et al, 2006 | NM_198253 | TERT |
| Transglutaminase | Forms isopeptide bonds | Mirza et al, 1997 | NM_000359 | TGM1 |
| TTG | Tissue transglutaminase | Chen et al, 2008 | NM_004613 | TGM2 |
| Type II-secreted phospholipase A2 | Proinflammatory phospholipase | Couturier et al, 1999 | NM_000437 | PAFAH2 |
| Uridine phosphorylase | 5-fluorouracil and capecitabine metabolism | Wan et al, 2006 | NM_003364 | UPP1 |
| *Xanthine Dehydrogenase | Oxidative metabolism of purines | Xu et al, 1996 | NM_000379 | XDH |

Table 6M. Miscellaneous

| Gene | Function | Reference | Accession No. | Human Gene Name |
|---|---|---|---|---|
| *ABCG5 (bovine) | ATP-binding cassette sterol transporters | Viturro et al, 2006 | NM_022436 | ABCG5 |
| ABCG8 (bovine) | ATP-binding cassette sterol transporters | Viturro et al, 2006 | NM_022437 | ABCG8 |
| AbetaH-J-J | Tripartite gene: aspartyl-beta-hydroxylase, junctin), junctate | Feriotto et al, 2005 | NM_004318 | ASPH |
| alpha-1 acid glycoprotein | Serum protein | Meidoubi et al, 1999 | NM_000607 | ORM1 |
| alpha-fetoprotein | Liver cancer marker | Cavin et al, 2004 | NM_001134 | AFP |
| AMH | Anti-Mullerian hormone | Lukas-Croisier et al, 2003 | NM_000479 | AMH |
| *beta-amyloid | Alzheimer's precursor | Song & Lahiri, 1998 | NM_000484 | A4 |
| APOBEC2 | Apolipoportein B mRNA-editing enzyme catalytic subunit 2 | Matsumoto et al, 2006 | NM_006789 | APOBEC2 |
| Apolipoprotein C III | Apoprotein of HDL | Gruber et al, 1994 | NM_000040 | APOC3 |
| Apolipoprotein D | Plasma lipocalin | Do Carmo et al, 2007 | NM_001647 | APOD |
| Apolipoprotein E | Protein assoc. with Alzheimers | Lahiri, 2004; Du et al, 2005 | NM_000041 | APOE |
| AQP4 | Aquaporin 4 | Ito et al, 2006 | NM_001650 | AQP4 |
| *Biglycan | Connective tissue proteoglycan | Ungefroren & Krull, 1996 | NM_001711 | BGN |

*Figure 15-18*

| Gene | Function | Reference | Accession No. | Human Gene Name |
|---|---|---|---|---|
| BRCA2 | Breast Cancer Susceptibility protein-2 | Wu et al, 2000 | NM_000059 | BRCA2 |
| Calsarcin-1 | Muscle cell calcineurin-interacting protein | Wang et al, 2007 | NM_021245 | MYOZ1 |
| *Caveolin-1 | Lipid raft protein | Deregowski et al, 2002 | NM_001753 | CAV1 |
| *Clone 330 | Possible secreted protein | Matsuda et al, 2003 | | |
| *Clone 156 | Unknown NF-kB inducer | Matsuda et al, 2003 | | |
| *Clone 68 | Unknown NF-kB inducer | Matsuda et al, 2003 | | |
| *p21-CIP1 | Cyclin-dependent kinase inhibitor | Hinata et al, 2003 | NM_000389 | CDKN1A |
| *Claudin-2 | Gap junction protein | Yamamoto et al, 2004 | NM_020384 | CLDN2 |
| a2(I) collagen | Type I collagen | Novitskiy et al, 2004; Nieto, 2007 | NM_000089 | COL1A2 |
| *Connexin32 | Gap junction protein | Yamamoto et al, 2004 | NM_000166 | GJB1 |
| Cyclin D1 | Cell-cycle regulation | Guttridge et al, 1999; Hinz et al, 1999; Toualbi-Abed et al, 2008 | NM_053056 | CCND1 |
| Cyclin D2 | Cell-cycle regulation | Huang et al, 2004; Iwanaga et al, 2008 | NM_001759 | CCND2 |
| *Cyclin D3 | Cell-cycle regulation | Wang et al, 1996 | NM_001760 | CCND3 |
| DIF2 | Monocyte differentiation gene | Witcher et al, 2007 | NM_003897 | IER3 |
| DMT1 | Divalent metal ion transporter | Paradkar et al, 2005 | NM_000617 | SLC11A2 |
| Elafin | Proteinase inhibitor | Bingle et al, 2001 | NM_002638 | SKALP, PI3 |
| Endothelin 1 | Vasoconstrictor peptide/mitogen | Quehenberger et al, 2000 | NM_001955 | EDN1 |
| Ephrin-A1 | Cell-cycle regulation | Deregowski et al, 2002 | NM_005232 | EPHA1 |
| Factor VIII | Hemostasis | Figueiredo & Brownlee, 1995 | NM_000132 | F8 |
| Ferritin Heavy Chain | Anti-oxidant | Kwak et al, 1995 | NM_002032 | FTH1 |
| Gadd45beta | DNA repair/cell cycle | De Smaele et al, 2001; Qiu et al, 2004 | NM_015675 | GADD45B |
| Galpha i2 | G protein | Arinze & Kawai, 2005 | NM_002070 | GNAI2 |
| *GIF | Cys-rich metal binding protein | Hinata et al, 2003 | NM_005954 | MT3 |
| Galectin 3 | b-galactosidase-binding lectin | Hsu et al, 1996 | NR_003225 | LGALS3 |
| GBP-1 | GTPase guanylate binding protein | Naschberger et al, 2004 | NM_002053 | GBP1 |
| epsilon-Globin | Globin protein | Hou et al, 2002, 2004 | NM_005330 | HBE1 |

*Figure 15-19*

| Gene | Function | Reference | Accession No. | Human Gene Name |
|---|---|---|---|---|
| zeta-Globin | Globin protein | Wang & Liebhaber, 1999 | NM_005332 | HBZ |
| *GS3686 | Homology to microtubule aggregating protein | Carter et al, 2002 | NM_006820 | IFI44L |
| Hair K5 keratin | Hair keratin protein | Gilon et al, 2007 | NM_000424 | KRT5 |
| *HCCS1 | Hepatocarcinoma suppressor 1 | Zhu et al, 2006 | NM_018289 | VPS53 |
| HMG14 | High mobility group 14 | Walker & Enrietto, 1996 | NM_004965 | HMGN1 |
| IBABP | Ileal bile acid binding protein | Fang et al, 2007 | NM_001445 | FABP6 |
| IMP2 | Insulin-like growth factor-II mRNA binding protein | Cleynen et al, 2007 | NM_000597 | IGFBP2 |
| K3 Keratin | Intermediate filament protein | Wu et al, 1994 | NM_057088 | KRT3 |
| K6b Keratin | Intermediate filament protein | Komine et al, 2000 | NM_005555 | KRT6B |
| K15 Keratin | Intermediate filament protein | Radoja et al, 2004 | NM_002275 | KRT15 |
| *Lactoferrin | Milk protein | Zheng et al, 2005 | NM_002343 | LTF |
| Laminin B2 Chain | Basement membrane protein | Richardson et al, 1995 | NM_002292 | LAMB2 |
| Lipocalin-2 | Iron-siderophore-binding protein | Fujino et al, 2005 | NM_005564 | LCN2 |
| Mts1 | Multiple tumor suppressor | Tulchinsky et al, 1997 | NM_002961 | S100A4 |
| Mir125b | Micro-RNA TNFa | Tili et al, 2007 | | |
| Mir146a, b | Micro-RNA for IRAK and Traf6 | Taganov et al, 2006 | | |
| Mir155 | Micro-RNA for FADD, IKKe, Ripk1 | Tili et al, 2007 | | |
| MNE1 | Monocyte/neutrophil elastase inhibitor | Zeng et al, 2000 | NM_030666 | SERPINB1 |
| Mucin (MUC-2) | Airway defense glycoprotein | Jono et al, 2002; Lee et al, 2000 | NM_002457 | MUC2 |
| Myelin basic protein | Neural sheath | Paez et al, 2006 | NM_001025081 | MBP |
| MCT1 | Monocarboxylate transporter isoform 1 | Borthakur et al, 2007 | NM_003051 | SLC16A1 |
| Naf1 | Associates with HIV Nef | Tian et al, 2005 | NM_006058 | TNIP1 |
| Neutrophil gelatinase-associated lipocalin | Anti-microbial protein in lung | Cowland et al, 2003 | NM_005564 | LCN2 |
| NLF1 | IL-1beta induced | Warton et al, 2004 | NM_207322 | FAM148A |
| *p11 | Annexin II ligand | Huang et al, 2003 | NM_002966 | S100A10 |
| PA28 alpha | Proteasome activator | Ossendorp et al, 2005 | NM_006263 | PSME1 |
| PA28 beta | Proteasome activator | Ossendorp et al, 2005 | NM_002818 | PSME2 |
| PAI-1 | Plasminogen activator inhibitor | Hou et al, 2004 | NM_000602 | SERPINE1, PAI-1 |
| *Pax8 | Paired box gene | Okladnova et al, 1997 | NM_003466 | PAX8 |

Figure 15-20

| Gene | Function | Reference | Accession No. | Human Gene Name |
|---|---|---|---|---|
| *PCBD | 6-pyruvoyl-tetrahydropterin synthase | Carter et al, 2002 | NM_000317 | PTS |
| Perforin | Pore-forming effector molecule | Zhou et al, 2002 | NM_005041 | PRF1 |
| PGC-1β | mitochondrial regulator PPAR-γ coactivator 1β | Bakkar et. al. 2012 | NM_001172698.1 | PPARGC1B |
| *PGK1 | Phosphoglycerate kinase 1 | Carter et al, 2002 | NM_000291 | PGK1 |
| POMC | Proopiomelanocortin | Karalis et al, 2004; Asaba et al, 2007 | NM_000939 | POMC |
| Pregnancy-specific glycoprotein rnCGM3 | Placental expression | Wang et al, 2001 | NM_019126 | CGM3 |
| Prodynorphin | Neuropeptide | Bakalkin et al, 1994 | NM_024411 | PDYN |
| Prostate-specific antigen | Serum protein in prostate cancer | Chen & Sawyers, 2002 | NM_001030047 | KLK3 |
| PTEN | Tumor suppressor | Xia et al, 2007 | NM_000314 | PTEN |
| RAG-1 | Immunoglobulin recombinase genes | Verkoczy et al, 2005 | NM_000448 | RAG1 |
| RAG-2 | Immunoglobulin recombinase genes | Verkoczy et al, 2005 | NM_000536 | RAG2 |
| RbAp48 | Retinoblastoma-associated protein 48 | Pacifico et al, 2007 | NM_005610 | RBBP4 |
| *RICK | Adaptor | Matsuda et al, 2003 | NM_003821 | RIPK2 |
| SerpinE2 | Serine protease inhibitor | Suzuki et al, 2006 | NM_006216 | SERPINE2 |
| S100A6 (calcyclin) | Calcium binding protein | Joo et al, 2003 | NM_014624 | S100A6 |
| SH3BGRL | SH3-binding glutamic acid-rich protein | Majid et al, 2005 | NM_003022 | SH3BGRL |
| SK2 channels | Small-conductance Ca2+-activated channels | Kye et al, 2007 | NM_021614 | KCNN2 |
| Skp2 | S-phase kinase-associated protein 2 | Schneider et al, 2006 | NM_005983 | SKP2 |
| *Spergen-1 | Sperm-specific mitochondrial protein | Matsuoka et al, 2004 | NM_174927 | SPATA19 |
| SWS1 | Rainbow trout opsin | Dann et al, 2004 | NM_001708 | OPN1SW |
| Syncytin-1 | Env glycoprotein of endogenous human retrovirus | Mameli et al, 2007 | NM_014590 | ERVWE1 |
| Syndecan-4 | Heparin sulfate proteoglycan | Zhang et al, 1999 | NM_002999 | SDC4 |
| TAUT | Taurine Uptake Transporter | Mochizuki et al, 2005 | NM_003043 | SLC6A6 |
| TASK-2 | Tandem P domain potassium channel | Brazier et al, 2005 | NM_003740 | KCNK5 |
| *Tissue factor pathway inhibitor-2 (TFPI-2) | Serine protease inhibitor | Konduri et al, 2003a, 2003b; Hube et al, 2003 | NM_006528 | TFPI2 |
| *Transferrin (mosquito) | Probable iron transport protein | Harizanova et al, 2005 | NM_001063 | TF |
| TRIF | TIR-containing adaptor protein inducing interferon beta | Hardy et al, 2004 | NM_014261 | TICAM1 |

*Figure 15-21*

| Gene | Function | Reference | Accession No. | Human Gene Name |
|---|---|---|---|---|
| TRPC1 | Thrombin activation of protease-activated receptor-1 | Paria et al, 2006 | NM_003304 | TRPC1 |
| *UBE2M | Ubiquitin conjugating enzyme E2M | Carter et al, 2002 | NM_003969 | UBE2M |
| *UCP-2 | Uncoupling protein-2 | Lee et al, 1999 | NM_003355 | UCP2 |
| Uroplakin Ib | Surface structural protein on urothelial cells | Varga et al, 2004 | NM_006952 | UPK1B |
| 25-hydroxyvtamin D3 1alpha hydroxylase | Enzyme for liver vitamin D3 production | Ebert et al, 2004 | NM_000785 | CYP27B1 |
| Vimentin | Intermediate filament protein | Lilienbaum et al, 1990; Zheng et al, 2005 | NM_003380 | VIM |
| a1-antitrypsin | Protease inhibitor | Ray et al, 1995 | NM_000295 | SERPINA1 |
| Gro-1 | Growth regulated oncogene; chemokine | Wood, 1995 | NM_001511 | CXCL1 |

Table 6N. Viruses

| Gene | Function | Reference |
|---|---|---|
| Adenovirus (E3 region) | Adenovirus | Williams et al, 1990 |
| Avian Leukosis Virus | Causes avian leukosis | Bowers et al, 1996 |
| Bovine Leukemia Virus | Causes bovine leukemia | Brooks et al, 1998 |
| CMV | Cytomegalovirus | Sambucetti et al, 1989 |
| EBV (Wp promoter) | Epstein-Barr virus | Sugano et al, 1997 |
| HBV (pregenomic promoter) | Hepatitis B virus | Kwon & Rho, 2002 |
| HIV-1 | Human immunodeficiency virus | Nabel & Baltimore, 1987; Griffin et al, 1989 |
| HSV (ICP90, ICP0) | Herpes simplex virus | Rong et al, 1992; La Frazia et al, 2006 |
| JC Virus | Polyoma virus | Ranganathan & Khalili, 1993 |
| HPV type 16 | Human Papillomavirus | Fontaine et al, 2000 |
| SIV | Simian immunodeficiency virus | Bellas et al, 1993 |
| SV-40 | Simian virus 40 | Kanno et al, 1989 |

Table 6O. Other

| For 135 additional potential NF-kB target genes, which are predicted by computer-based methods to have composite NF-kB/C/EBP regulatory sites, see Shelest et al., 2003. |
|---|
| For 9 additional potential NF-kB immune function target genes, see Liu et al., 2003. |

*Figure 15-22*

| |
|---|
| For several hundred predicted NF-kB target genes in pancreatic cells, see Naamane et al, 2007. |
| For additional c-Rel-specific target genes, see Bunting et al, 2007. |
| For 23 possible additional NF-kB targets from microarrays see Takase et al, 2008. |

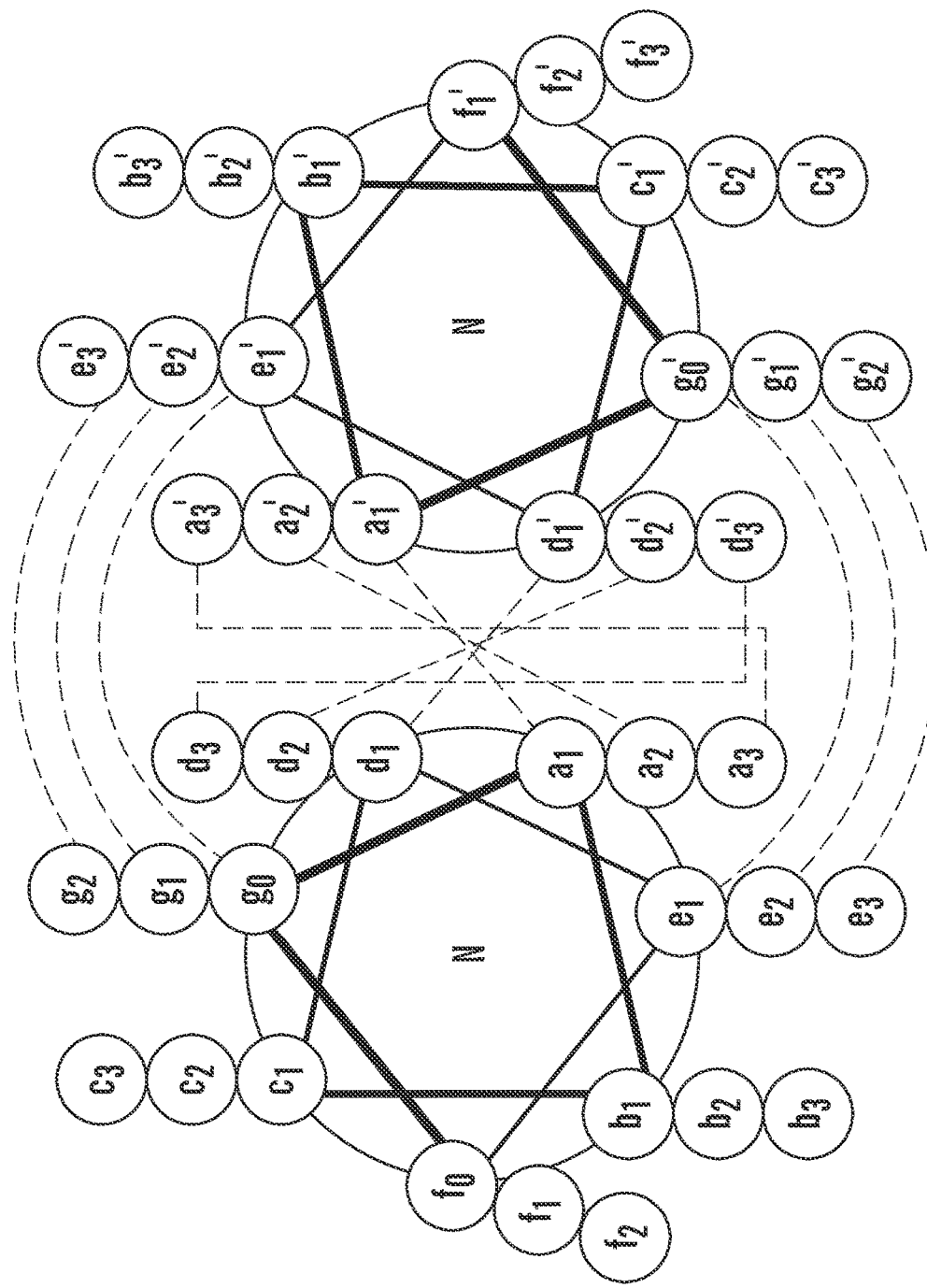
*FIG. 16* (helical wheel view)

(two-dimensional view)

SEQUENCE LISTING

```
<160> NUMBER OF SEQ ID NOS: 22

<210> SEQ ID NO 1
<211> LENGTH: 21
<212> TYPE: PRT
<213> ORGANISM: Artificial
<220> FEATURE:
<223> OTHER INFORMATION: First Coil of Formula I
<220> FEATURE:
<221> NAME/KEY: MISC_FEATURE
<222> LOCATION: (1)..(21)
<223> OTHER INFORMATION: Xaa at positions 1-21 are each independently
      absent or any amino acid residue selected from the group
      consisting of modified or unmodified amino acid residues and
      analogues thereof

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 2
<211> LENGTH: 21
<212> TYPE: PRT
<213> ORGANISM: Artificial
<220> FEATURE:
<223> OTHER INFORMATION: Second Coil of Formula II
<220> FEATURE:
<221> NAME/KEY: MISC_FEATURE
<222> LOCATION: (1)..(21)
<223> OTHER INFORMATION: Xaa at positions 1-21 are each independently
      absent or any amino acid residue selected from the group
```

-continued consisting of modified or unmodified amino acid residues and
analogues thereof

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 3
<211> LENGTH: 14
<212> TYPE: PRT
<213> ORGANISM: Artificial
<220> FEATURE:
<223> OTHER INFORMATION: First Coil
<220> FEATURE:
<221> NAME/KEY: MISC_FEATURE
<222> LOCATION: (1)..(1)
<223> OTHER INFORMATION: Xaa at position 1 can be any amino acid residue
<220> FEATURE:
<221> NAME/KEY: MISC_FEATURE
<222> LOCATION: (2)..(2)
<223> OTHER INFORMATION: Xaa at position 2 is a modified or unmodified
      Trp or analogue thereof
<220> FEATURE:
<221> NAME/KEY: MISC_FEATURE
<222> LOCATION: (3)..(3)
<223> OTHER INFORMATION: Xaa at position 3 can be any hydrophobic amino
      acid residue
<220> FEATURE:
<221> NAME/KEY: MISC_FEATURE
<222> LOCATION: (4)..(4)
<223> OTHER INFORMATION: Xaa at position 4 can be any positively charged
      amino acid residue
<220> FEATURE:
<221> NAME/KEY: MISC_FEATURE
<222> LOCATION: (5)..(5)
<223> OTHER INFORMATION: Xaa at position 5 is a modified or unmodified
      Gln or analogue thereof
<220> FEATURE:
<221> NAME/KEY: MISC_FEATURE
<222> LOCATION: (6)..(6)
<223> OTHER INFORMATION: Xaa at position 6 can be any hydrophobic acid
      residue
<220> FEATURE:
<221> NAME/KEY: MISC_FEATURE
<222> LOCATION: (7)..(7)
<223> OTHER INFORMATION: Xaa at position 7 can be any amino acid residue
<220> FEATURE:
<221> NAME/KEY: MISC_FEATURE
<222> LOCATION: (8)..(8)
<223> OTHER INFORMATION: Xaa at position 8 is any negatively charged
      amino acid residue or a modified or unmodified Gln or analogue
      thereof
<220> FEATURE:
<221> NAME/KEY: MISC_FEATURE
<222> LOCATION: (9)..(9)
<223> OTHER INFORMATION: Xaa at position 9 is a modified or unmodified
      QCy or analogue thereof
<220> FEATURE:
<221> NAME/KEY: MISC_FEATURE
<222> LOCATION: (10)..(10)
<223> OTHER INFORMATION: Xaa at position 10 can be any hydrophobic amino
      acid residue
<220> FEATURE:
<221> NAME/KEY: MISC_FEATURE
<222> LOCATION: (11)..(11)
<223> OTHER INFORMATION: Xaa at position 11 can be any amino acid
      residue
<220> FEATURE:
<221> NAME/KEY: MISC_FEATURE
<222> LOCATION: (12)..(12)
<223> OTHER INFORMATION: Xaa at position 11 is a modified or unmodified
      Arg or analogue thereof
<220> FEATURE:
<221> NAME/KEY: MISC_FEATURE

```
<222> LOCATION: (13)..(13)
<223> OTHER INFORMATION: Xaa at position 13 is any hydrophobic amino
      acid residue
<220> FEATURE:
<221> NAME/KEY: MISC_FEATURE
<222> LOCATION: (14)..(14)
<223> OTHER INFORMATION: Xaa at position 14 is azidolysine or an
      analogue thereof, a modified or unmodified Glu or analogue
      thereof, or a modified or unmodified Arg or analogue thereof

<400> SEQUENCE: 3

Xaa Xaa Xaa Xaa Xaa Xaa Xaa Xaa Xaa Xaa Xaa Xaa Xaa Xaa
1               5                   10

<210> SEQ ID NO 4
<211> LENGTH: 14
<212> TYPE: PRT
<213> ORGANISM: Artificial
<220> FEATURE:
<223> OTHER INFORMATION: First Coil
<220> FEATURE:
<221> NAME/KEY: MISC_FEATURE
<222> LOCATION: (1)..(1)
<223> OTHER INFORMATION: Xaa at position 1 is Val or Glu
<220> FEATURE:
<221> NAME/KEY: MISC_FEATURE
<222> LOCATION: (3)..(3)
<223> OTHER INFORMATION: Xaa at position 3 is independently Cys, HCys,
      Leu, lle, allylleucine, Val, allyglycine, Thr, selenocysteine,
      hexafluoroleucine, hexafluorovaline (or analogue of any of the
      preceding residues)
<220> FEATURE:
<221> NAME/KEY: MISC_FEATURE
<222> LOCATION: (4)..(4)
<223> OTHER INFORMATION: Xaa at position 4 is His or Arg
<220> FEATURE:
<221> NAME/KEY: MISC_FEATURE
<222> LOCATION: (6)..(6)
<223> OTHER INFORMATION: Xaa at positions 6 is independently Cys, HCys,
      Leu, lle, allylleucine, Val, allyglycine, Thr, selenocysteine,
      hexafluoroleucine, hexafluorovaline (or analogue of any of the
      preceding residues)
<220> FEATURE:
<221> NAME/KEY: MISC_FEATURE
<222> LOCATION: (7)..(7)
<223> OTHER INFORMATION: Xaa at position 7 is Phe, Tyr, Trp,
      azidolysine, or Cys
<220> FEATURE:
<221> NAME/KEY: MISC_FEATURE
<222> LOCATION: (8)..(8)
<223> OTHER INFORMATION: Xaa at position 8 is Gln or Glu
<220> FEATURE:
<221> NAME/KEY: MISC_FEATURE
<222> LOCATION: (9)..(9)
<223> OTHER INFORMATION: Xaa at position 9 is QCy
<220> FEATURE:
<221> NAME/KEY: MISC_FEATURE
<222> LOCATION: (10)..(10)
<223> OTHER INFORMATION: Xaa at position 10 is independently Cys, HCys,
      Leu, lle, allylleucine, Val, allyglycine, Thr, selenocysteine,
      hexafluoroleucine, hexafluorovaline (or analogue of any of the
      preceding residues)
<220> FEATURE:
<221> NAME/KEY: MISC_FEATURE
<222> LOCATION: (11)..(11)
<223> OTHER INFORMATION: Xaa at position 11 is Asp or Arg
<220> FEATURE:
<221> NAME/KEY: MISC_FEATURE
<222> LOCATION: (13)..(13)
<223> OTHER INFORMATION: Xaa at position 13 is independently Cys, HCys,
      Leu, lle, allylleucine, Val, allyglycine, Thr, selenocysteine,
      hexafluoroleucine, hexafluorovaline (or analogue of any of the
      preceding residues)
<220> FEATURE:
<221> NAME/KEY: MISC_FEATURE
<222> LOCATION: (14)..(14)
<223> OTHER INFORMATION: Xaa at position 14 is azidolysine, Glu, or Arg
```

<400> SEQUENCE: 4

Xaa Trp Xaa Xaa Gln Xaa Xaa Xaa Xaa Xaa Xaa Arg Xaa Xaa
1               5                   10

<210> SEQ ID NO 5
<211> LENGTH: 14
<212> TYPE: PRT
<213> ORGANISM: Artificial
<220> FEATURE:
<223> OTHER INFORMATION: Second Coil
<220> FEATURE:
<221> NAME/KEY: MISC_FEATURE
<222> LOCATION: (1)..(1)
<223> OTHER INFORMATION: Xaa at position 1 can be any amino acid residue
<220> FEATURE:
<221> NAME/KEY: MISC_FEATURE
<222> LOCATION: (2)..(2)
<223> OTHER INFORMATION: Xaa at position 2 can be any hydrophobic amino
      acid residue
<220> FEATURE:
<221> NAME/KEY: MISC_FEATURE
<222> LOCATION: (3)..(3)
<223> OTHER INFORMATION: Xaa at position 3 is a modified or unmodified
      His or analogue thereof
<220> FEATURE:
<221> NAME/KEY: MISC_FEATURE
<222> LOCATION: (4)..(4)
<223> OTHER INFORMATION: Xaa at position 4 can be any positively charged
      amino acid residue or a modified or unmodified Gln or analogue
      thereof
<220> FEATURE:
<221> NAME/KEY: MISC_FEATURE
<222> LOCATION: (5)..(5)
<223> OTHER INFORMATION: Xaa at position 5 can be any hydrophobic amino
      acid residue
<220> FEATURE:
<221> NAME/KEY: MISC_FEATURE
<222> LOCATION: (6)..(6)
<223> OTHER INFORMATION: Xaa at position 6 is a modified or unmodified
      Phe or analogue thereof
<220> FEATURE:
<221> NAME/KEY: MISC_FEATURE
<222> LOCATION: (7)..(7)
<223> OTHER INFORMATION: Xaa at position 7 can be any positively charged
      residue or a modified or unmodified Gln or analogue thereof
<220> FEATURE:
<221> NAME/KEY: MISC_FEATURE
<222> LOCATION: (8)..(8)
<223> OTHER INFORMATION: Xaa at position 8 is azidolysine or an analogue
      thereof, a modified or unmodified Glu or analogue thereof, or a
      modified or unmodified Asp or analogue thereof
<220> FEATURE:
<221> NAME/KEY: MISC_FEATURE
<222> LOCATION: (9)..(9)
<223> OTHER INFORMATION: Xaa at position 9 can be any hydrophobic amino
      acid residue
<220> FEATURE:
<221> NAME/KEY: MISC_FEATURE
<222> LOCATION: (10)..(10)
<223> OTHER INFORMATION: Xaa at position 10 can be any modified or
      unmodified Asp or analogue thereof
<220> FEATURE:
<221> NAME/KEY: MISC_FEATURE
<222> LOCATION: (11)..(11)
<223> OTHER INFORMATION: Xaa at position 11 can be any negatively
      charged amino acid residue, modified or unmodified Asn, or
      analogue thereof
<220> FEATURE:
<221> NAME/KEY: MISC_FEATURE
<222> LOCATION: (12)..(12)
<223> OTHER INFORMATION: Xaa at position 12 can be any hydrophobic
      residue
<220> FEATURE:
<221> NAME/KEY: MISC_FEATURE
<222> LOCATION: (13)..(13)
<223> OTHER INFORMATION: Xaa at position 13 can be any modified or unmodified Ile or analogue thereof
<220> FEATURE:
<221> NAME/KEY: MISC_FEATURE
<222> LOCATION: (14)..(14)
<223> OTHER INFORMATION: Xaa at position 14 can be any modified or
      unmodified Arg and positvely charged analogue thereof

<400> SEQUENCE: 5

Xaa Xaa Xaa Xaa Xaa Xaa Xaa Xaa Xaa Xaa Xaa Xaa Xaa Xaa
1               5                   10

<210> SEQ ID NO 6
<211> LENGTH: 14
<212> TYPE: PRT
<213> ORGANISM: Artificial
<220> FEATURE:
<223> OTHER INFORMATION: Second Coil
<220> FEATURE:
<221> NAME/KEY: MISC_FEATURE
<222> LOCATION: (1)..(1)
<223> OTHER INFORMATION: Xaa at position 1 is Ala, Glu, azidolysine, or
      Cys
<220> FEATURE:
<221> NAME/KEY: MISC_FEATURE
<222> LOCATION: (2)..(2)
<223> OTHER INFORMATION: Xaa at position 2 is independently Cys, HCys,
      Leu, Ile, allylleucine, Val, allylglycine, Thr, selenocysteine,
      hexafluoroleucine, hexafluorovaline (or analogues of any of the
      preceding residues
<220> FEATURE:
<221> NAME/KEY: MISC_FEATURE
<222> LOCATION: (4)..(4)
<223> OTHER INFORMATION: Xaa at position 4 is Gln or Arg
<220> FEATURE:
<221> NAME/KEY: MISC_FEATURE
<222> LOCATION: (5)..(5)
<223> OTHER INFORMATION: Xaa at position 5 is independently Cys, HCys,
      Leu, Ile, allylleucine, Val, allylglycine, Thr, selenocysteine,
      hexafluoroleucine, hexafluorovaline (or analogues of any of the
      preceding residues
<220> FEATURE:
<221> NAME/KEY: MISC_FEATURE
<222> LOCATION: (7)..(7)
<223> OTHER INFORMATION: Xaa as position 7 is Gln or Arg
<220> FEATURE:
<221> NAME/KEY: MISC_FEATURE
<222> LOCATION: (8)..(8)
<223> OTHER INFORMATION: Xaa at position 8 is azidolysine, Glu, or Arg
<220> FEATURE:
<221> NAME/KEY: MISC_FEATURE
<222> LOCATION: (9)..(9)
<223> OTHER INFORMATION: Xaa at position 9 is independently Cys, HCys,
      Leu, Ile, allylleucine, Val, allylglycine, Thr, selenocysteine,
      hexafluoroleucine, hexafluorovaline (or analogues of any of the
      preceding residues
<220> FEATURE:
<221> NAME/KEY: MISC_FEATURE
<222> LOCATION: (11)..(11)
<223> OTHER INFORMATION: Xaa at position 11 is Asn or Glu
<220> FEATURE:
<221> NAME/KEY: MISC_FEATURE
<222> LOCATION: (12)..(12)
<223> OTHER INFORMATION: Xaa at position 12 is independently Cys, HCys,
      Leu, Ile, allylleucine, Val, allylglycine, Thr, selenocysteine,
      hexafluoroleucine, hexafluorovaline (or analogues of any of the
      preceding residues

<400> SEQUENCE: 6

Xaa Xaa His Xaa Xaa Phe Xaa Xaa Xaa Asp Xaa Xaa Ile Arg
1               5                   10

<210> SEQ ID NO 7
<211> LENGTH: 14
<212> TYPE: PRT
<213> ORGANISM: Artificial

```
<220> FEATURE:
<223> OTHER INFORMATION: First Coil

<400> SEQUENCE: 7

Val Ala Tyr His Gln Leu Phe Gln Glu Tyr Asp Asn His Ile
1               5                   10

<210> SEQ ID NO 8
<211> LENGTH: 14
<212> TYPE: PRT
<213> ORGANISM: Artificial
<220> FEATURE:
<223> OTHER INFORMATION: NEMO-vFLIP inhibitor coil

<400> SEQUENCE: 8

Ala Tyr His Gln Leu Phe Gln Glu Tyr Asp Asn His Ile Lys
1               5                   10

<210> SEQ ID NO 9
<211> LENGTH: 14
<212> TYPE: PRT
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (14)..(14)
<223> OTHER INFORMATION: Xaa at position 14 is azidolysine or an
      analogue thereof

<400> SEQUENCE: 9

Glu Ala Ile Arg Gln Leu Tyr Glu Glu Ile Arg Asn Leu Xaa
1               5                   10

<210> SEQ ID NO 10
<211> LENGTH: 14
<212> TYPE: PRT
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (8)..(8)
<223> OTHER INFORMATION: Xaa at position 8 is azidolysine or an analogue
      thereof

<400> SEQUENCE: 10

Glu Ile His Arg Leu Phe Arg Xaa Ile Asp Glu Leu Ile Arg
1               5                   10

<210> SEQ ID NO 11
<211> LENGTH: 14
<212> TYPE: PRT
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (14)..(14)
<223> OTHER INFORMATION: Xaa at position 14 is azidolysine or an
      analogue thereof

<400> SEQUENCE: 11

Glu Trp Ile Arg Gln Leu Trp Glu Glu Ile Arg Arg Leu Xaa
1               5                   10

<210> SEQ ID NO 12
<211> LENGTH: 14
<212> TYPE: PRT
```

```
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (8)..(8)
<223> OTHER INFORMATION: Xaa at position 8 is azidolysine or an analogue
      thereof

<400> SEQUENCE: 12

Glu Ile His Arg Leu Phe Arg Xaa Ile Asp Glu Leu Ile Arg
1               5                   10

<210> SEQ ID NO 13
<211> LENGTH: 14
<212> TYPE: PRT
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (9)..(9)
<223> OTHER INFORMATION: Xaa at position 9 is a modified or unmodified
      QCy or analogue thereof
<220> FEATURE:
<221> NAME/KEY: MISC_FEATURE
<222> LOCATION: (14)..(14)
<223> OTHER INFORMATION: Xaa at position 14 is azidolysine or an
      analogue thereof

<400> SEQUENCE: 13

Glu Trp Ile Arg Gln Leu Trp Glu Xaa Ile Arg Arg Leu Xaa
1               5                   10

<210> SEQ ID NO 14
<211> LENGTH: 14
<212> TYPE: PRT
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (8)..(8)
<223> OTHER INFORMATION: Xaa at position 8 is azidolysine or an analogue
      thereof

<400> SEQUENCE: 14

Glu Ile His Arg Leu Phe Arg Xaa Ile Asp Glu Leu Ile Arg
1               5                   10

<210> SEQ ID NO 15
<211> LENGTH: 14
<212> TYPE: PRT
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (9)..(9)
<223> OTHER INFORMATION: Xaa at position 9 is a modified or unmodified
      QCy or analogue thereof
<220> FEATURE:
<221> NAME/KEY: MISC_FEATURE
<222> LOCATION: (14)..(14)
<223> OTHER INFORMATION: Xaa at position 14 is azidolysine or an
      analogue thereof

<400> SEQUENCE: 15

Glu Ala Ile Arg Gln Leu Trp Glu Xaa Ile Arg Arg Leu Xaa
1               5                   10
```

```
<210> SEQ ID NO 16
<211> LENGTH: 14
<212> TYPE: PRT
<213> ORGANISM: Artificial
<220> FEATURE:
<223> OTHER INFORMATION: NEMO-vFLIP inhibitor coil
<220> FEATURE:
<221> NAME/KEY: MISC_FEATURE
<222> LOCATION: (8)..(8)
<223> OTHER INFORMATION: Xaa at position 8 is azidolysine or an analogue
      thereof

<400> SEQUENCE: 16

Glu Ile Ala Arg Leu Phe Arg Xaa Ile Asp Glu Leu Ile Arg
1               5                   10

<210> SEQ ID NO 17
<211> LENGTH: 16
<212> TYPE: PRT
<213> ORGANISM: Artificial
<220> FEATURE:
<223> OTHER INFORMATION: UNC NEMO
<220> FEATURE:
<221> NAME/KEY: MISC_FEATURE
<222> LOCATION: (1)..(1)
<223> OTHER INFORMATION: Gln at position 1 is acetylated

<400> SEQUENCE: 17

Gln Val Ala Tyr His Gln Leu Phe Gln Glu Tyr Asp Asn His Ile Lys
1               5                   10                  15

<210> SEQ ID NO 18
<211> LENGTH: 16
<212> TYPE: PRT
<213> ORGANISM: Artificial
<220> FEATURE:
<223> OTHER INFORMATION: HBS NEMO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 18

Xaa Gln Val Gly Phe Gln Leu Phe Gln Glu Tyr Asp Asn His Ile Lys
1               5                   10                  15

<210> SEQ ID NO 19
<211> LENGTH: 29
<212> TYPE: PRT
<213> ORGANISM: Artificial
<220> FEATURE:
<223> OTHER INFORMATION: Signal peptide

<400> SEQUENCE: 19

Met Met Ser Phe Val Ser Leu Leu Leu Val Gly Ile Leu Phe Tyr Ala
1               5                   10                  15

Thr Glu Ala Glu Gln Leu Thr Lys Cys Glu Val Phe Gln
            20                  25

<210> SEQ ID NO 20
<211> LENGTH: 4
<212> TYPE: PRT
<213> ORGANISM: Artificial
<220> FEATURE:
<223> OTHER INFORMATION: ER Retention Signal

<400> SEQUENCE: 20

Lys Glu Asp Leu
1
```

```
<210> SEQ ID NO 21
<211> LENGTH: 8
<212> TYPE: PRT
<213> ORGANISM: Artificial
<220> FEATURE:
<223> OTHER INFORMATION: nuclear transport peptide

<400> SEQUENCE: 21

Pro Pro Lys Lys Lys Arg Lys Val
1               5

<210> SEQ ID NO 22
<211> LENGTH: 25
<212> TYPE: PRT
<213> ORGANISM: Artificial
<220> FEATURE:
<223> OTHER INFORMATION: transport peptide sequence

<400> SEQUENCE: 22

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25
```

NEMO COILED COIL MIMICS AND METHODS OF USING SAME

This application is a continuation of U.S. patent application Ser. No. 16/684,082, filed Nov. 14, 2019, which claims the benefit of U.S. Provisional Patent Application Ser. No. 62/768,373, filed Nov. 16, 2018, which is hereby incorporated by reference in its entirety.

This invention was made with government support under grant numbers R01CA154228, R01GM073943, and R01GM120736 awarded by the National Institutes of Health. The government has certain rights in the invention.

FIELD OF THE INVENTION

This invention is directed to stabilized coiled coils that mimic NEMO and methods of using such mimics.

SEQUENCE LISTING

This application contains a computer readable Sequence Listing, which has been submitted electronically in TXT format and is hereby incorporated by reference in its entirety. Said TXT copy, created on Sep. 11, 2023, is named 147462.002002_ST25.txt and is 14,661 bytes in size.

BACKGROUND OF THE INVENTION

Two herpesviruses cause cancer in humans: Epstein-Barr virus (EBV/HHV-4) and Kaposi sarcoma herpesvirus (KSHV/HHV-8). Cancers caused by KSHV include malignant lymphomas and Kaposi sarcoma (KS), which occur more frequently but not exclusively in individuals with AIDS and other immunodeficiencies. Primary effusion lymphomas (PELs) are associated with both KSHV and EBV. KSHV also causes multicentric Castleman disease (MCD), an aggressive lymphoproliferative disorder.

The occurrence of many herpesvirus-associated malignancies in sub-Saharan Africa (SSA) poses an enormous challenge to their accurate diagnosis and curative treatment. KS is a cancer of lymphatic endothelial cells, or possibly those of mesenchymal origin. There are four epidemiologic forms of KS: classic, endemic, iatrogenic, and epidemic or AIDS-KS, the most common AIDS-defining malignancy (Mesri et al., *Nat. Rev. Cancer* 10(10):707-19 (2010)). KSHV can be detected in virtually all cases of KS in spindle cells by immunohistochemistry using antibodies to the viral protein LANA or by PCR.

KS is one of the most common malignancies in SSA, where even before AIDS, the region had among the highest KS incidence in the world (Davies et al., *Br. Med. J.* 1(5379):336-41(1964); Maclean, C. M., *Br. J. Cancer* 17:195-205 (1963)). The AIDS epidemic has dramatically altered the epidemiology of KS in Africa as well as its severity. Many, but not all, patients with KS have AIDS, and better distribution of antiretroviral therapies has diminished the number of cases diagnosed in Africa in the previous decade from about 70,000 to a documented 37,500 in 2012 (likely an underestimate given the number of undiagnosed cases and suboptimal cancer registries in the region) (Parkin et al., *Cancer Epidemiol. Biomarkers Prev.* 23(6):953-66 (2014)). Thus, KS remains one of the most frequent malignancies and most common cause of cancer-related death in SSA, and is reported to be the cancer with the highest incidence in males in six countries in East Africa (Parkin et al., *Cancer Epidemiol. Biomarkers Prev.* 23(6):953-66 (2014)).

Prior to the availability of combined antiretroviral therapy (cART), survival after diagnosis of AIDS-related KS in Africa was dismal; one-year mortality was approximately 60% to 70% (Mwanda et al., *Ann. Trop. Med. Parasitol.* 99(1):81-91 (2005); Olweny et al., *Int. J. Cancer* 113(4): 632-9 (2005)). While cART improves outcome, mortality remains between 20% and 40% within one year of diagnosis and close to 70% three years after diagnosis (Makombe et al., *Trop. Doct.* 38(1):5-7 (2008); Geng et al., *JAMA* 300 (5):506-7 (2008); Chu et al., *J. Int. AIDS Soc.* 13:23 (2010); Mosam et al., *J. Acquir. Immune Defic. Syndr.* 60(2):150-7 (2012); Agaba et al., *Int. J. STD AIDS* 20(6):410-3 (2009)).

Poor survival of KS can be explained by a combination of late diagnosis, lack of medical infrastructure to support ill patients, and lack of accessible effective therapies. Around 80% of patients in SSA are seen for the first time with disseminated, advanced (T1) KS, with worse prognosis (Chu et al., *J. Int. AIDS Soc.* 13:23 (2010); Mosam et al., *J. Acquir. Immune Defic. Syndr.* 60(2):150-7 (2012); Agaba et al., *Int. J. STD AIDS* 20(6):410-3 (2009)). The treatment of choice is liposomal doxorubicin (e.g., Doxil), but even when available, rarely leads to complete responses in advanced KS and results only in partial responses in around half of the patients (Udhrain et al., *Int. J. Nanomedicine* 2(3):345-52 (2007)). In addition, in some HIV$^+$ patients, KS may progress dramatically and even fatally upon treatment with antiretrovirals, due to an immune reconstitution inflammatory syndrome (IRIS) (Letang et al., *AIDS* 27(10):1603-13 (2013); Feller et al, *Infect. Agent Cancer* 2008; Bower et al., *J Clin. Oncol.* 23(22):5224-8 (2005); Leidner et al., *AIDS Patient Care STDS* 19(10):635-44 (2005)). Systemic chemotherapy can suppress IRIS flares, but only when administered early (Leidner et al., *AIDS Patient Care STDS* 19(10):635-44 (2005)). Clearly, availability of specific targeted therapies without the toxicity of chemotherapy would facilitate early treatment of KS in SSA and improve outcome globally.

While KS has increased incidence in individuals with HIV infection, this cancer is also common in SSA in children and adults without HIV infection. Prevention and development of vaccines to KSHV would be ideal to prevent cancers associated with infection. While progress is being made towards vaccine development, this effort has been hampered due to specific biological features such as latency and immune evasion. A KSHV vaccine is not expected to be available in the foreseeable future (Maubach et al., *Trends Mol. Med.* 23:1138-55 (2017)).

KSHV also causes primary effusion lymphoma (PEL) and multicentric Castleman disease (MCD), two aggressive lymphoproliferative disorders. The geographic predilection of many herpesvirus-associated malignancies poses an enormous challenge to their accurate diagnosis and curative treatment. The patient survival in KS remains poor globally, and development and translation of new therapeutics that are more targeted and efficacious than standard chemotherapy treatment would be of great clinical benefit.

KSHV vFLIP (viral FLICE inhibitory protein) is a viral oncogene encoded by KSHV and latently expressed in tumor cells. vFLIP is a protein that results in activation of NFkB by binding to a double helical region of NEMO (IKKγ). KSHV vFLIP appears to be a viable therapeutic target for KSHV-associated malignancies, which continue to represent a global health problem. Identification of specific, pharmacologically viable inhibitors of vFLIP would lead to the first anti-viral therapeutics for cancer.

Inhibition of the vFLIP/NEMO interaction is challenging because it represents a protein-protein interaction (PPI). Many PPIs are thought to be difficult to disrupt with small molecules because of frequently large interacting surfaces. Protein-protein interactions have been recognized as challenging targets for synthetic inhibitors. It has also been recognized that the difficulty in targeting PPIs is directly correlated with the intricacy of the binding epitopes, with complexes of tertiary structures proving to be the most recalcitrant. Interactions of NEMO, a scaffolding protein that is a central component of NF-κB signaling, exemplify this challenge. Various regulators, including viral oncoproteins, are known to interact with different coiled coil regions of NEMO but the topological complexity of this scaffolding protein has limited inhibitor design.

The NF-κB essential modulator (NEMO or IKKγ) serves as a key fulcrum in the NF-κB signaling network by coupling the upstream NF-κB signaling to IKK complex catalytic subunits through its elongated coiled coil motif (Maubach et al., *Trends Mol. Med* 23:1138-55 (2017)). NEMO is hijacked by various external factors, including viral oncoproteins, to initiate aberrant signaling; however, the topological complexity of the NEMO-mediated protein-protein interactions (PPIs) has limited discovery of inhibitors. The challenge of disrupting intracellular tertiary structure mediated protein-protein interactions is well-appreciated (Arkin et al., *Chemistry & Biology* 21:1102-14 (2014); Checco et al., *Proc. Natl. Acad Sci. USA* 112:455-57 (2015); Thompson et al., *ACS Chem. Biol.* 7:1311-20 (2012)). While several examples of synthetic inhibitors of secondary structure-mediated protein interfaces have now been described (Azzarito et al., *Nat. Chem.* 5:161-73 (2013); Chang et al., *Proc. Natl. Acad Sci. USA* 110:E3445-54 (2013); Lao et al., *J. Am. Chem. Soc.* 136:7877-88 (2014)), it has been difficult to develop cell-permeable ligands that mimic the more topologically complex epitopes of tertiary structures such as those involving NEMO (Checco et al., *Proc. Natl. Acad Sci. USA* 112:455-57 (2015)).

Viral oncoproteins provide an attractive opportunity to develop specific inhibitors for carcinogenesis without engaging native cellular signaling. (Mesri et al., *Cell Host Microbe* 15:266-82 (2014)). The Kaposi sarcoma herpesvirus (KSHV), also called human herpesvirus 8 (HHV-8) is implicated in AIDS-associated malignancies, including primary effusion lymphoma (PEL) and Kaposi sarcoma (KS) (Field et al., *J. Cell. Sci.* 116:3721-8 (2003); Matta et al., *J. Biol. Chem.* 278:52406-11 (2003); Chugh et al., *Proc. Natl. Acad. Sci. USA* 102:12885-90 (2005); Lee et al., *Nat. Cell Biol.* 11:1355-62 (2009); Arvanitakis et al., *Blood* 88:2648-54 (1996); Boshoff et al., *Adv. Cancer. Res.* 75:57-86 (1998)). While anti-herpes viral drugs exist, these inhibit lytic virus and not the virus in tumor cells, which are latently infected. (Gramolelli et al., *Curr. Opin. Virol.* 26:156-62 (2017)) vFLIP is a viral oncoprotein expressed during KSHV latency, and is a promising viral therapeutic target (Chugh et al., *Proc. Natl. Acad. Sci. USA* 102:12885-90 (2005); Ballon et al., *PLoS Pathog.* 11:e1004581 (2015); Briggs et al., *J. Virol.* 91(2017)) that can act by engaging NEMO and constitutively activating the NF-iB pathway (FIGS. 1A-B) (Ballon et al., *J. Clin. Invest.* 121:1141-53 (2011); Liu et al., *J. Biol. Chem.* 277:13745-51 (2002); Shimizu et al., *J. Virol.* 85:7444-8 (2011); Bagneris et al., *J. Biol. Chem.* 290:16539-49 (2015); Tolani et al., *J Virol.* 88:6345-54 (2014)). Complex formation between NEMO HLX2 coiled-coil domain (aa, 193-252) and vFLIP induces nuclear translocation and dimerization of p65/p50 or p65/c-Rel heterodimeric transcription factors, leading to transcription of critical genes whose expression is linked to cell survival, inflammation, and protection against death-receptor-mediated apoptosis (Tolani et al., *J. Virol.* 88:6345-54 (2014); Bagneris et al., *Mol. Cell* 30:620-31 (2008); Keller et al., *Blood* 107:3295-302 (2006)).

The present invention is directed to overcoming these and other deficiencies in the art.

SUMMARY OF THE INVENTION

One aspect of the present invention relates to a macrostructure. This macrostructure includes a parallel coiled-coil, wherein the parallel coiled-coil comprises:

a first coil of Formula I and a second coil of Formula II:

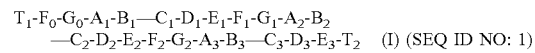

$$T_1\text{-}F_0\text{-}G_0\text{-}A_1\text{-}B_1\text{---}C_1\text{-}D_1\text{-}E_1\text{-}F_1\text{-}G_1\text{-}A_2\text{-}B_2$$
$$\text{---}C_2\text{-}D_2\text{-}E_2\text{-}F_2\text{-}G_2\text{-}A_3\text{-}B_3\text{---}C_3\text{-}D_3\text{-}E_3\text{-}T_2 \quad \text{(I) (SEQ ID NO: 1)}$$

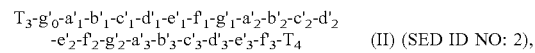

$$T_3\text{-}g'_0\text{-}a'_1\text{-}b'_1\text{-}c'_1\text{-}d'_1\text{-}e'_1\text{-}f'_1\text{-}g'_1\text{-}a'_2\text{-}b'_2\text{-}c'_2\text{-}d'_2$$
$$\text{-}e'_2\text{-}f'_2\text{-}g'_2\text{-}a'_3\text{-}b'_3\text{-}c'_3\text{-}d'_3\text{-}e'_3\text{-}f'_3\text{-}T_4 \quad \text{(II) (SED ID NO: 2),}$$

wherein:

each $a_{1-3}$, $b_{1-3}$, $C_{1-3}$, $d_{1-3}$, $e_{1-3}$, $f_{0-2}$, $g_{0-2}$, $a'_{1-3}$, $b'_{1-3}$, $c'_{1-3}$, $d'_{1-3}$, $e'_{1-3}$, $f'_{1-3}$, and $g'_{0-2}$ is independently absent or a residue selected from the group consisting of modified or unmodified amino acid residues and analogues thereof, one or more of the following residue pairs are covalently bound by a linker:

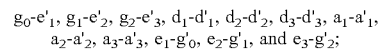

$g_0$-$e'_1$, $g_1$-$e'_2$, $g_2$-$e'_3$, $d_1$-$d'_1$, $d_2$-$d'_2$, $d_3$-$d'_3$, $a_1$-$a'_1$,
$a_2$-$a'_2$, $a_3$-$a'_3$, $e_1$-$g'_0$, $e_2$-$g'_1$, and $e_3$-$g'_2$;

each $T_1$ and $T_3$ is independently a point of attachment from a terminal nitrogen to one or more (preferably one or two) moieties, wherein each moiety independently H, —$PG_1$, —C(O)R, —C(O)$NR_2$, —C(O)$NH_2$, —R, —C(O)OR, an amino acid or analogue thereof, a peptide, a targeting moiety, or a tag, where $PG_1$ is an amine protecting group and each R is independently hydrogen, an alkyl, an alkenyl, an alkynyl, a cycloalkyl, an aryl, a heteroaryl, a heterocyclyl, an arylalkyl, a peptide, a targeting moiety, or a tag; and each $T_2$ and $T_4$ is independently a point of attachment from a terminal carbonyl to H, —OPG2, —$NPG_2$, —OR, —OH, —$NR_2$, —$NH_2$, —N(R)C(O)$C_{1-6}$ alkyl, N(H)C(O)$C_{1-6}$ alkyl, an amino acid or analogue thereof, a peptide, a targeting moiety, or a tag, where $PG_2$ is a carboxylic acid protecting group and each R is independently hydrogen, an alkyl, an alkenyl, an alkynyl, a cycloalkyl, an aryl, a heteroaryl, a heterocyclyl, an arylalkyl, a peptide, a targeting moiety, or a tag;

and wherein:

the first coil comprises at least fourteen contiguous residues, wherein the at least fourteen contiguous residues have the formula $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$;

the second coil comprises at least fourteen contiguous residues, wherein the at least fourteen contiguous residues have the formula $X'_1$-$X'_2$-$X'_3$-$X'_4$-$X'_5$-$X'_6$-$X'_7$-$X'_8$-$X'_9$-$X'_{10}$-$X'_{11}$-$X'_{12}$-$X'_{13}$-$X'_{14}$; and wherein each residue is selected from the groups indicated below (superscript letters indicate each residue's location within Formula I and Formula II; residues in the a, a', d, d', e, e', g, and g' positions can optionally be modified to facilitate attachment of a linker or replaced with a linker)

| Residue | Group | Preferred Residue(s) |
|---|---|---|
| First Coil | | |
| $^f X_1$ | any residue | Val, Glu |
| $^g X_2$ | modified or unmodified Trp and analogues thereof | Trp |
| $^a X_3$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^b X_4$ | any positively charged residue | His, Arg |
| $^c X_5$ | modified or unmodified Gln and analogues thereof | Gln |
| $^d X_6$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^e X_7$ | any residue | Phe, Tyr, Trp, azidolysine, Cys |
| $^f X_8$ | any negatively charged residue, modified or unmodified Gln and analogues thereof | Gln, Glu |
| $^g X_9$ | modified or unmodified $Q^{Cy}$ and analogues thereof | $Q^{Cy}$ |
| $^a X_{10}$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^b X_{11}$ | any residue | Asp, Arg |
| $^c X_{12}$ | modified or unmodified Arg and analogues thereof | Arg |
| $^d X_{13}$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^e X_{14}$ | azidolysine and analogues thereof, modified or unmodified Glu and analogues thereof, modified or unmodified Arg and analogues thereof | azidolysine, Glu, Arg |
| Second Coil | | |
| $^g X'_1$ | any residue | Ala, Glu, azidolysine, Cys |
| $^a X'_2$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^b X'_3$ | modified or unmodified His and analogues thereof | His |
| $^c X'_4$ | any positively charged residue, modified or unmodified Gln and analogues thereof | Gln, Arg |
| $^d X'_5$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^e X'_6$ | modified or unmodified Phe and analogues thereof | Phe |
| $^f X'_7$ | any positively charged residue, modified or unmodified Gln and analogues thereof | Gln, Arg |
| $^g X'_8$ | azidolysine and analogues thereof, modified or | azidolysine, Glu, Arg |

-continued

| Residue | Group | Preferred Residue(s) |
|---|---|---|
| | unmodified Glu and analogues thereof, modified or unmodified Arg and analogues thereof | |
| $^aX'_9$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^bX'_{10}$ | modified or unmodified Asp and analogues thereof | Asp |
| $^cX'_{11}$ | any negatively charged residue, modified or unmodified Asn and analogues thereof | Asn, Glu |
| $^dX'_{12}$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^eX'_{13}$ | modified or unmodified Ile and analogues thereof | Ile |
| $^fX'_{14}$ | modified or unmodified Arg and positively charged analogues thereof | Arg |

Another aspect of the present invention is a method of inhibiting interaction between NEMO and a target molecule that binds to a helix dimer consisting of HLX1 and HLX2 of NEMO. This method involves contacting NEMO and/or the target molecule with a macrostructure as described herein under conditions effective to inhibit interaction between NEMO and the target molecule.

Another aspect of the present invention is a method of modulating transcription of a gene in a cell, wherein transcription of the gene is regulated by interaction between NEMO and a target molecule that binds to a helix dimer consisting of HLX1 and HLX2 of NEMO. This method involves contacting the cell with a macrostructure as described herein under conditions effective to modulate transcription of the gene.

Another aspect of the present invention is a method of inhibiting NFκB signalling in a cell. This method involves contacting the cell with a macrostructure as described herein under conditions effective to inhibit NFκB signalling in the cell, wherein NFκB signalling in the cell is mediated by interaction between NEMO and a target molecule that binds to a helix dimer consisting of HLX1 and HLX2 of NEMO.

Another aspect of the present invention is a method of treating in a subject a disorder mediated by interaction between NEMO and a target molecule that binds to a helix dimer consisting of HLX1 and HLX2 of NEMO. This method involves administering to the subject a macrostructure or a pharmaceutical formulation as described herein under conditions effective to treat the disorder in the subject.

As demonstrated herein, the macrostructures described herein can be used, among other things, to selectively downregulate NF-κB signaling in vFLIP-driven primary effusion lymphoma and delay tumor growth in vivo. These optimized helical tertiary structure mimics of NEMO provide specificity and potency in modulating cellular signaling.

BRIEF DESCRIPTION OF THE DRAWINGS

FIGS. 1A-B are an overview of vFLIP-mediated activation of NF-κB signaling pathway. (FIG. 1A) Binding of vFLIP, a viral oncoprotein, to NEMO activates NF-κB signaling. NEMO adopts a helical coiled coil motif to bind to vFLIP (PDB Code 3CL3). We explored small molecule libraries, stabilized α-helices, and crosslinked helix dimers (CHDs) to inhibit NEMO-vFLIP complex formation. Potent inhibition required a CHD motif that captured critical contacts from both helices of NEMO coiled coil. (FIG. 1B) Cartoon depicts various binding partners of NEMO responsible for activating and repressing NF-κB. vFLIP shown here in green binds the second helical domain (HLX2) downstream of the IKKα/β binding region.

FIGS. 2A-C show the rational design of inhibitors of the NEMO-vFLIP interaction. (FIG. 2A) Helical wheel diagram depicting native (top) NEMO coiled coil and optimized (bottom) sequences. A crosslinker is placed at the e and g positions to constrain the dimer. (FIG. 2B) (SEQ ID NOs: 7-16) Peptide sequences of designed compounds and their respective inhibitory constants from the TR-FRET assay. Representative inhibitory constants from at least three replicate experiments are shown. (FIG. 2C) Cartoon depicts four high-ranking pockets identified by AlphaSpace and corresponding residues from CHD3$^{NEMO}$. The changes in % pocket occupancy as a result of three mutations are highlighted. $^a$Incomplete dissociation of the NEMO-vFLIP complex observed at 100 μM concentrations (FIG. 3A).

FIGS. 3A-F show the biophysical characterization, stability and cellular uptake of NEMO mimics. (FIG. 3A) The potential of NEMO mimics to inhibit vFLIP-NEMO interaction was evaluated in a TR-FRET assay by monitoring the fluorescence ratio of the acceptor/donor. These studies illustrated the potency of the optimized derivative CHD3$^{NEMO}$. Data plotted represent mean±s.e.m of three replicate experiments. TR-FRET signal was normalized to DMSO control and expressed as percent inhibition. (FIG. 3B) The specific association of the FITC-derivatized CHD3$^{NEMO}$ with vFLIP over full length NEMO was further probed in a fluorescence polarization assay. Data shown represent mean±s.d. of two independent experiments performed in triplicate. Data was normalized to c. (FIG. 3C) The conformation of the coiled coil mimics was investigated by circular dichroism spectroscopy in aqueous buffer. The reported values represent mean±s.e.m of two independent experiments. (FIG. 3D) The conformational stability of CHD3$^{NEMO}$ was further evaluated in a thermal denaturation study. The circular dichroism spectra were collected at regular intervals between 5-95° C. Data shown represent one experiment where scans were recorded five times over the temperature range. (FIG. 3E) CHD3$^{NEMO}$ was found to resist serum proteases. Peptide degradation was probed over 24 h by HPLC. (FIG. 4F) Cellular uptake of FITC-labeled CHD3$^{NEMO}$ into live BC-1 cells. Cells were visualized by fluorescence microscopy after 1 hour incubation. Effect of temperature and 10 mM sodium azide on the cellular uptake of the NEMO mimic was also explored. Hoechst stain was used to detect the nuclei. Representative live confocal images from at least three replicate experiments are shown.

FIGS. 4A-C show CHD3$^{NEMO}$ suppresses vFLIP-mediated NF-κB transcriptional activity and disrupts NEMO-vFLIP complex formation. (FIG. 4A) CHD3$^{NEMO}$ inhibits NF-κB transcriptional activity in BC-3 NF-κB-luc PEL cells in a dose-dependent manner at (FIG. 4A) t=5 h and (FIG. 4B) t=24 h post-treatment. BC-3 reporter cell line was treated with increasing concentrations of the different NEMO mimetics or in the presence of the NF-κB inhibitor Bay 11-7082 or HSP90 inhibitor PU-H71. Luciferase assays were performed at the indicated time points. Data plotted represent mean±s.e.m of at least three independent experiments. Statistical analysis was performed using unpaired t-test comparing treated samples to DMSO control (**p≤0.0001, *p≤0.001, **p≤0.01, *p≤0.05 and non-significant p>0.05). (FIG. 4C) CHD3$^{NEMO}$ disrupts vFLIP/NEMO interaction in live cells. Co-immunoprecipitation with an anti-FLAG antibody was performed using a vFLIP-FLAG doxycycline-inducible Namalwa cell line. Results show a dose-dependent reduction in the levels of interacting NEMO upon treating cells with the vFLIP inhibitor CHD3$^{NEMO}$ but not with the mutant CHD4$^{NEMO}$ peptide. WT uninduced: Namalwa WT vFLIP stable cell line without induction with doxycycline; Mock: parental Namalwa cell line; Mut vFLIP: Namalwa stable cell line carrying vFLIP NF-κB dead mutant that lacks the ability to bind to NEMO. Mut vFLIP and WT vFLIP were treated with doxycycline to induce vFLIP expression 24 hrs prior to treating with DMSO or CHDs. Data shown is representative of three independent experiments showing similar results.

FIGS. 5A-C show CHD3$^{NEMO}$ induces apoptotic cell death in vFLIP-expressing PEL cell lines. (FIG. 5A) CHD3$^{NEMO}$ but not CHD4$^{NEMO}$ mutant induces cell death in a panel of PEL cell lines. vFLIP (−) Namalwa cell line was used as a control. Cells were treated with increasing concentrations of CHD3$^{NEMO}$ or CHD4$^{NEMO}$ and cytotoxicity was quantified after 48 h using a CellTiter-Glo assay that measures ATP content as a proxy for cell viability. Results plotted represent mean±s.e.m of at least three independent experiments performed in duplicates. (FIGS. 5B-C) Flow cytometry analysis showing that CHD3$^{NEMO}$ induces apoptosis in vFLIP (+) BC-1 PEL cell line, but not vFLIP (−) Namalwa. BC-1 cells were treated with DMSO, 5 μM, 25 μM or 50 μM of CHD3$^{NEMO}$ for 48 hours. After staining for DAPI and Annexin V, cells were examined using flow cytometry. Results were quantified into percentages of live (Annexin V−, DAPI−), early apoptotic cells (Annexin V+) or late apoptotic cells (Annexin V+/DAPI+ and DAPI+). Results shown are the average of 3 independent experiments.

FIGS. 6A-C show the effect of CHD3$^{NEMO}$ on tumor growth in a traceable reporter BC-3-Luc PEL xenograft mouse model. (FIG. 6A) Box- and Whisker plots of relative tumor burden at day 20 post-engraftment quantified using bioluminescence imaging. Statistical analysis was performed using Mann Whitney test (p=0.012, *p≤0.05). One representative mice for each group is presented (right). (FIG. 6B) Bioluminescence quantitation representing tumor burden after 20 days of tumor engraftment in the vehicle group (blue line, n=10) versus CHD3$^{NEMO}$ treated group (red line, n=5). (FIG. 6C) Kaplan-Meier survival analysis showing that mice treated with the CHD3$^{NEMO}$ peptide (in red) has a survival advantage compared to the control group (in blue). The difference in survival curves was analyzed by log-rank (Mantel-Cox) test (P=0.002).

FIGS. 7A-D are schematic representations of the Time-resolved Fluorescence Energy Transfer (TR-FRET) binding assay. (FIG. 7A) Complexes of recombinant his-MBP vFLIP, biotinylated His-NEMO, Europium cryptate conjugated anti-MBP antibody, and strepavidin XL665 were used to generate proximity for a FRET signal between the donor fluorophore Europium cryptate and the acceptor fluorophore strepavidin XL665. The TR-FRET signal was calculated as a ratiometric measurement of the acceptor fluorescence emission at 665 nm over the donor emission at 620 nm multiplied by 10000. (FIG. 7B) Matrix grid with serial dilutions of NEMO and vFLIP to optimize protein concentration and TR-FRET signal. Data plotted represent mean±s.e.m of two independent experiments. At each concentration of NEMO, the concentration of vFLIP reads, from left to right: 0 nM, 1.6 nM, 3.1 nM, 6.3 nM, 12.5 nM, 25 nM, 50 nM, 100 nM, 200 nM, 400 nM, 800 nM. (FIG. 7C) Direct binding assay of highest ratio signal (50 nM). (FIG. 7D) Size exclusion chromatography of NEMO-vFLIP complex indicating a shift to the left in absorbance at 280 nm when NEMO binds specifically to vFLIP. MBP is used as a negative control.

FIGS. 8A-B. (FIG. 8A) TR-FRET (left) and Circular Dichroism (CD) spectra (right) of UNC$^{NEMO}$ (SEQ ID NO: 17) and HBS$^{NEMO}$ (SEQ ID NO: 18). Peptides used in CD studies were dissolved at 50 μM concentration in 50 mM Potassium Fluoride pH 7.4 supplemented with 10% TFE. Data represented is mean±s.e.m of three replicate experiments. (FIG. 8B) Structure of HBS$^{NEMO}$.

FIG. 15 lists target genes of NFκB (Tables 6A-60).

DETAILED DESCRIPTION OF THE INVENTION

Figure 5C:
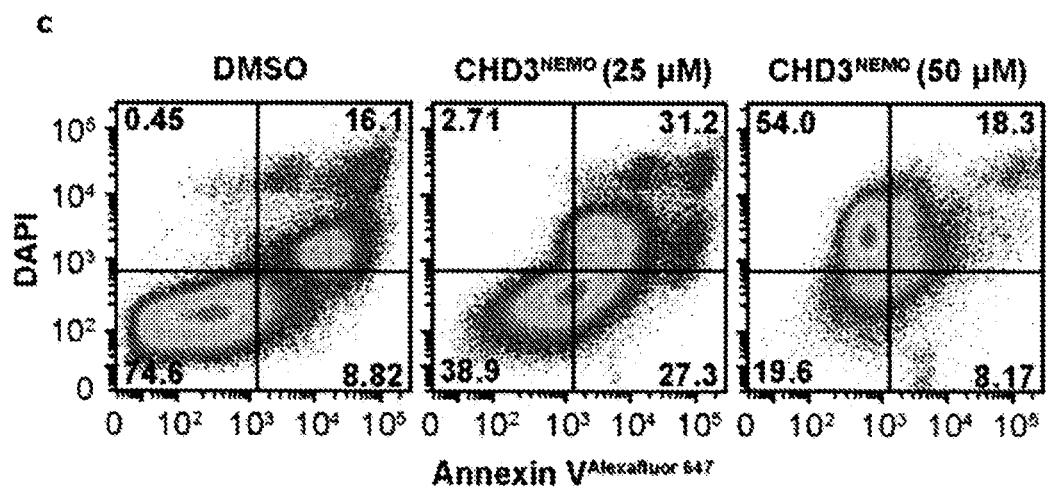

The following detailed description is presented to enable any person skilled in the art to make and use the subject technology. For purposes of explanation, specific nomenclature is set forth to provide a thorough understanding of the present invention. However, it will be apparent to one skilled in the art that these specific details are not required to practice the technology. Descriptions of specific applications are provided only as representative examples. The present technology is not intended to be limited to the embodiments shown, but is to be accorded the widest possible scope consistent with the principles and features disclosed herein. Preferences and options for a given aspect, feature, or parameter of the invention should, unless the context indicates otherwise, be regarded as having been disclosed in combination with any and all preferences and options for all other aspects, features, and parameters of the invention.

One aspect of the present invention relates to a macrostructure. This macrostructure includes a parallel coiled-coil, wherein the parallel coiled-coil comprises:

a first coil of Formula I and a second coil of Formula II:

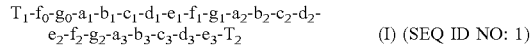

(I) (SEQ ID NO: 1)

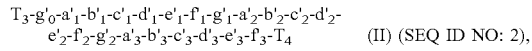

(II) (SEQ ID NO: 2), wherein:

each $a_{1-3}$, $b_{1-3}$, $c_{1-3}$, $d_{1-3}$, $e_{1-3}$, $f_{0-2}$, $g_{0-2}$, $a'_{1-3}$, $b'_{1-3}$, $c'_{1-3}$, $d'_{1-3}$, $e'_{1-3}$, $f'_{1-3}$, and $g'_{0-2}$ is independently absent or a residue selected from the group consisting of modified or unmodified amino acid residues and analogues thereof, one or more of the following residue pairs are covalently bound by a linker: $g_0$-$e'_1$, $g_1$-$e'_2$, $g_2$-$e'_3$, $d_1$-$d'_1$, $d_2$-$d'_2$, $d_3$-$d'_3$, $a_1$-$a'_1$, $a_2$-$a'_2$, $a_3$-$a'_3$, $e_1$-$g'_0$, $e_2$-$g'_1$, and $e_3$-$g'_2$;

each $T_1$ and $T_3$ is independently a point of attachment from a terminal nitrogen to one or more (preferably one or two) moieties, wherein each moiety is independently H, —PG$_1$, —C(O)R, —C(O)NR$_2$, —C(O)NH$_2$, —R, —C(O)OR, an amino acid or analogue thereof, a peptide, a targeting moiety, or a tag, where PG$_1$ is an amine protecting group and each R is independently hydrogen, an alkyl, an alkenyl, an alkynyl, a cycloalkyl, an aryl, a heteroaryl, a heterocyclyl, an arylalkyl, a peptide, a targeting moiety, or a tag; and each $T_2$ and $T_4$ is independently a point of attachment from a terminal carbonyl to H, —OPG$_2$, —NPG$_2$, —OR, —OH, —NR$_2$, —NH$_2$, —N(R)C(O)C$_{1-6}$ alkyl, —N(H)C(O)C$_{1-6}$ alkyl, an amino acid or analogue thereof, a peptide, a targeting moiety, or a tag, where PG$_2$ is a carboxylic acid protecting group and each R is independently hydrogen, an alkyl, an alkenyl, an alkynyl, a cycloalkyl, an aryl, a heteroaryl, a heterocyclyl, an arylalkyl, a peptide, a targeting moiety, or a tag;

and wherein:

the first coil comprises at least fourteen contiguous residues, wherein the at least fourteen contiguous residues have the formula $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$;

the second coil comprises at least fourteen contiguous residues, wherein the at least fourteen contiguous residues have the formula $X'_1$-$X'_2$-$X'_3$-$X'_4$-$X'_5$-$X'_6$-$X'_7$-$X'_8$-$X'_9$-$X'_{10}$-$X'_{11}$-$X'_{12}$-$X'_{13}$-$X'_{14}$; and wherein each residue is selected from the groups indicated below (superscript letters indicate each residue's location within Formula I and Formula II; residues in the a, a', d, d', e, e', g, and g' positions can optionally be modified to facilitate attachment of a linker or replaced with a linker)

| Residue | Group | Preferred Residue(s) |
|---|---|---|
| First Coil | | |
| $^fX_1$ | any residue | Val, Glu |
| $^gX_2$ | modified or unmodified Trp and analogues thereof | Trp |
| $^aX_3$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^bX_4$ | any positively charged residue | His, Arg |
| $^cX_5$ | modified or unmodified Gln and analogues thereof | Gln |
| $^dX_6$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^eX_7$ | any residue | Phe, Tyr, Trp, azidolysine, Cys |
| $^fX_8$ | any negatively charged residue, modified or unmodified Gln and | Gln, Glu |

| Residue | Group | Preferred Residue(s) |
|---|---|---|
| $^gX_9$ | analogues thereof modified or unmodified $Q^{Cy}$ and analogues thereof | $Q^{Cy}$ |
| $^aX_{10}$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^bX_{11}$ | any residue | Asp, Arg |
| $^cX_{12}$ | modified or unmodified Arg and analogues thereof | Arg |
| $^dX_{13}$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^eX_{14}$ | azidolysine and analogues thereof, modified or unmodified Glu and analogues thereof, modified or unmodified Arg and analogues thereof | azidolysine, Glu, Arg |
| Second Coil | | |
| $^gX'_1$ | any residue | Ala, Glu, azidolysine, Cys |
| $^aX'_2$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^bX'_3$ | modified or unmodified His and analogues thereof | His |
| $^cX'_4$ | any positively charged residue, modified or unmodified Gln and analogues thereof | Gln, Arg |
| $^dX'_5$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^eX'_6$ | modified or unmodified Phe and analogues thereof | Phe |
| $^fX'_7$ | any positively charged residue, modified or unmodified Gln and analogues thereof | Gln, Arg |
| $^gX'_8$ | azidolysine and analogues thereof, modified or unmodified Glu and analogues thereof, modified or unmodified Arg and analogues thereof | azidolysine, Glu, Arg |
| $^aX'_9$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^bX'_{10}$ | modified or unmodified Asp and analogues thereof | Asp |
| $^cX'_{11}$ | any negatively charged residue, modified or unmodified Asn and analogues thereof | Asn, Glu |
| $^dX'_{12}$ | any hydrophobic residue | Cys, HCys, Leu, Ile, allylleucine, Val, allylglycine, Thr, selenocysteine, hexafluoroleucine, hexafluorovaline (or analogue of any of the preceding residues) |
| $^eX'_{13}$ | modified or | Ile |

-continued

| Residue | Group | Preferred Residue(s) |
|---|---|---|
| $X'_{14}$ | unmodified Ile and analogues thereof modified or unmodified Arg and positively charged analogues thereof | Arg |

Parallel coiled-coil structures each have a first amino acid strand (or first coil) and a second amino acid strand (or second coil). As will be readily apparent to the skilled artisan, the following conventions are commonly used to characterize coiled-coil structures and are used throughout this application. The convention "A/B" or "$^x A^y/^{x'} B^{y'}$" is used to identify the sequence of each strand (either specifically or generically), where A is the sequence ($X_1$-$X_2$-$X_3$ . . . ) of the first strand, B is the sequence ($X_1'$-$X_2'$-$X_3'$ . . . ) of the second strand, x, x', y, and y' identify the starting (x, x') and ending (y, y') locations of the corresponding sequences relative to heptad(s) in each strand, and "/" separates one sequence from the other. Conventionally, the A and B sequences are both written, left to right, in an N-to-C orientation. As will be readily apparent to the skilled artisan, the strands in a parallel coiled-coil structure are spatially aligned in the same direction, e.g., in a top view taken perpendicular to the axis of a parallel coiled-coil, the N-terminal of the first strand will be top-most and the N-terminal of the second strand will be top-most. As will be readily apparent to the skilled artisan, in the compounds of the present invention, there is also at least one covalent linker between a residue in the first strand and a residue in the second strand. The location and structure of the linker(s) are sometimes identified using "Z" and "Z'" in place of X and X', respectively, in the A and B sequences. Alternatively, the location and structure of the linker(s) are identified by additional explanation (e.g., "there is a disulfide linker between residue $X_n$ and residue $X_n'$").

As will be readily apparent to the skilled artisan, the helical wheel views herein show the spatial orientation of each coil in the parallel coiled-coil structure, while the two-dimensional views show the connections between residues.

As used above, and throughout the description of the invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

As used herein, the term "alkyl" means an aliphatic hydrocarbon group which may be straight or branched having about 1 to about 8 (e.g., 1-2, 1-3, 1-4, 1-5, 1-6, 1-7, 1-8) carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 8 (e.g., 2-3, 2-4, 2-5, 2-6, 2-7, 2-8) carbon atoms in the chain. Preferred alkenyl groups have 2 to about 4 carbon atoms in the chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 8 (e.g., 2-3, 2-4, 2-5, 2-6, 2-7, 2-8) carbon atoms in the chain. Preferred alkynyl groups have 2 to about 4 carbon atoms in the chain. Exemplary alkynyl groups include ethynyl, propynyl, n-butynyl, 2-butynyl, 3-methylbutynyl, and n-pentynyl.

As used herein, the term "cycloalkyl" refers to a non-aromatic saturated or unsaturated mono- or polycyclic ring system which may contain 3 to 8 (3, 4, 5, 6, 7, 8, 3-4, 3-5, 3-6, 3-7, 4-5, 4-6, 4-7, 4-8, 5-6, 5-7, 5-8, 6-7, 6-8, 7-8) carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "alkane" refers to aliphatic hydrocarbons of formula $C_nH_{2n+2}$, which may be straight or branched having about 1 to about 8 (e.g., 1-2, 1-3, 1-4, 1-5, 1-6, 1-7, 1-8) carbon atoms in the chain. Branched means that one or more lower alkyl groups such as methyl, ethyl, or propyl are attached to a linear alkyl chain. Exemplary alkanes include methane, ethane, n-propane, i-propane, n-butane, t-butane, n-pentane, and 3-pentane. The term "alkylene" refers to a divalent group formed from an alkane by removal of two hydrogen atoms. Exemplary alkylene groups include, but are not limited to, divalent groups derived from the alkanes described above.

As used herein, the term "alkene" refers to aliphatic unsaturated hydrocarbons of formula $C_nH_{2n}$, which may be straight or branched having about 2 to about 8 (e.g., 2-3, 2-4, 2-5, 2-6, 2-7, 2-8) carbon atoms in the chain. Exemplary alkenes include ethylene, propylene, n-butylene, and i-butylene. The term "alkenylene" refers to a divalent group formed from an alkene by removal of two hydrogen atoms. Alkenylenes contain a carbon-to-carbon double bond and are represented by the formula —$(C_nH_{n2-2})$—. Exemplary alkenylene groups include, but are not limited to, divalent groups derived from the alkenes described above.

As used herein, the term "alkyne" refers to aliphatic unsaturated hydrocarbons of formula $C_nH_{2n-2}$, which may be straight or branched having about 2 to about 8 (e.g., 2-3, 2-4, 2-5, 2-6, 2-7, 2-8) carbon atoms in the chain. Exemplary alkynes include acetylene, propyne, butyne, and pentyne. The term "alkynylene" refers to a divalent groups formed from alkynes by removal of two hydrogen atoms. Alkynylene contains a carbon-to-carbon triple bond and is represented by the formula —$(C_nH_{2n-1})$—. Exemplary alkynylene groups include, but are not limited to, divalent groups derived from the alkynes described above.

Aromatic rings and heteroaromatic rings can be any single, multiple, or fused ring structures. For example, aromatic or heteroaromatic rings include 5- or 6-membered aromatic or heteroaromatic rings containing 0-3 (0, 1, 2, or 3) heteroatoms selected from O, N, and S; a bicyclic 9- or 10-membered aromatic or heteroaromatic ring system containing 0-3 (0, 1, 2, or 3) heteroatoms selected from O, N, and S; or a tricyclic 13- or 14-membered aromatic or heteroaromatic ring system containing 0-3 (0, 1, 2, or 3) heteroatoms selected from O, N, and S. Aromatic 5- to 14-membered (5-, 6-, 7-, 8-, 9-, 10-, 11-, 12-, 13-, or 14-membered) carbocyclic rings include, e.g., cyclopenta-1,3-diene, benzene, naphthalene, indane, tetralin, and anthracene. 5- to 10-Membered (5-, 6-, 7-, 8-, 9-, or 10-membered) aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole, pyrazole, benzimidazole, pyridazine, pyrrole, imidazole, oxazole, isooxazole, indazole, isoindole, imidazole, purine, triazine, quinazoline, cinnoline, benzoxazole, acridine, benzisooxazole, and benzothiazole. The term "arylene" refers to a divalent group derived from an aromatic ring by removal of a hydrogen atom from two ring carbon atoms. Exemplary arylene groups include, but are not limited to, divalent groups derived from the aromatic rings described above. The term "heteroarylene" refers to a divalent group derived from a heteroaromatic ring. Exemplary heteroarylene groups include, but are not limited to, divalent groups derived from the heteroaromatic rings described above.

The term "ether" means a group having the formula —R—O—R—. Each R can be independently selected from the group consisting of a bond, $C_{1-8}$ alkylene, $C_{2-8}$ alkenylene, arylene, and heteroarylene. Exemplary ethers include, but are not limited to, —$C_{1-8}$ alkylene-O—$C_{1-8}$ alkylene- (e.g., —$(CH_2)_2$—O—$(CH_2)_2$—), —$C_{2-8}$ alkenylene-O—$C_{2-8}$ alkenylene-, -arylene-O-arylene-, -heteroarylene-O-heteroarylene-, and —$C_{1-8}$ alkylene-O-heteroarylene-.

The term "thioether" means a group having the formula —R—S—R—. Each R can be independently selected from the group consisting of a bond, $C_{1-8}$ alkylene, $C_{2-8}$ alkenylene, arylene, and heteroarylene. Exemplary thioethers include, but are not limited to, —$C_{1-8}$ alkylene-S—$C_{1-8}$ alkylene- (e.g., —$(CH_2)_2$—S—$(CH_2)_2$—), $C_{2-8}$ alkenylene-S—$C_{2-8}$ alkenylene-, -arylene-S-arylene-, -heteroarylene-S-heteroarylene-, and —$C_{1-8}$ alkylene-S-heteroarylene-.

The term "amide" means a group having the formula —$C(O)N(R^1)(R^1)$ or —$C(O)N(R^1)$—. Amides include, e.g., —$C(O)N(R^1)$ R—, —R—$C(O)N(R^1)$ R—, —$CHR^1$—$C(O)N(R^1)$ R—, and —$C(R^1)(R^1)$—$C(O)N(R^1)$ R—. Each R can be independently selected from the group consisting of a bond, $C_{1-8}$ alkylene, $C_{2-8}$ alkenylene, arylene, and heteroarylene, and each $R^1$ can be independently selected from the group consisting of hydrogen, $C_{1-8}$ alkyl, $C_{2-8}$ alkenyl, $C_{2-8}$ alkynyl, $C_{3-8}$ cycloalkyl, aryl, heteroaryl, heterocyclyl, and arylalkyl. Exemplary amides include, but are not limited to, —$C_{1-8}$ alkylene-C(O)N(aryl)-, —$C_{2-8}$ alkenylene-C(O)N(aryl)-, and —$C_{1-8}$ alkylene-C(O)N($C_{1-8}$ alkyl)- (e.g., —$(CH_2)_2$—$C(O)N(CH_3)$—).

The term "ester" means a group having the formula —C(O)O—. Esters include, e.g., —R—C(O)O—R—, —$CHR^1$—C(O)O—R—, and —$C(R^1)(R^1)$—C(O)O—R—. Each R can be independently selected from the group consisting of a bond, $C_{1-8}$ alkylene, $C_{2-8}$ alkenylene, arylene, and heteroarylene, and each $R^1$ can be independently selected from the group consisting of hydrogen, $C_{1-8}$ alkyl, $C_{2-8}$ alkenyl, $C_{2-8}$ alkynyl, $C_{3-8}$ cycloalkyl, aryl, heteroaryl, heterocyclyl, and arylalkyl. Exemplary esters include, but are not limited to, —$C_{1-8}$ alkylene-C(O)O-arylene-, —$C_{2-8}$ alkenylene-C(O)O-arylene-, —$C_{1-8}$ alkylene-C(O)O-heteroarylene-, —$C_{1-8}$ alkylene-C(O)O—$C_{1-8}$ alkylene- (e.g., —$(CH_2)_2$—C(O)O—$(CH_2)_2$—), and —$C_{1-8}$ alkylene-C(O)O— (e.g., —$(CH_2)_2$—C(O)O—).

As used herein, the term "heterocyclyl" refers to a stable 3- to 18-membered (3-, 4-, 5-, 6-, 7-, 8-, 9-, 10-, 11-, 12-, 13-, 14-, 15-, 16-, 17-, or 18-membered) ring system that consists of carbon atoms and from one to five (1, 2, 3, 4, 5, 1-2, 1-3, 1-4, 2-3, 2-5, 3-4, 3-5, 4-5) heteroatoms selected from the group consisting of nitrogen, oxygen, and sulfur. The heterocyclyl may be a monocyclic or a polycyclic ring system, which may include fused, bridged, or spiro ring systems; and the nitrogen, carbon, or sulfur atoms in the heterocyclyl may be optionally oxidized; the nitrogen atom may be optionally quaternized; and the ring may be partially or fully saturated. Representative monocyclic heterocyclyls include piperidine, piperazine, pyrimidine, morpholine, thiomorpholine, pyrrolidine, tetrahydrofuran, pyran, tetrahydropyran, oxetane, and the like. Representative polycyclic heterocyclyls include indole, isoindole, indolizine, quinoline, isoquinoline, purine, carbazole, dibenzofuran, chromene, xanthene, and the like.

As used herein, the term "aryl" refers to an aromatic monocyclic or polycyclic ring system containing from 6 to 19 (6, 7, 8, 9, 10, 11, 12, 13, 14, 15, 16, 17, 18, 19, 6-7, 6-8, 6-9, 6-10, 6-11, 6-12, 6-13, 6-14, 6-15, 6-16, 1-17, 6-18, 7-8, 7-9, 7-10, 7-11, 7-12, 7-13, 7-14, 7-15, 7-16, 7-18, 7-19, 8-9, 8-10, 8-11, 8-12, 8-13, 8-14, 8-15, 8-16, 8-17, 8-18, 8-19, 9-10, 9-11, 9-12, 9-13, 9-14, 9-15, 9-16, 9-17, 9-18, 9-19, 10-11, 10-12, 10-13, 10-14, 10-15, 10-16, 10-17, 10-18, 10-19, 11-12, 11-13, 11-14, 11-15, 11-16, 11-17, 11-18, 11-19, 12-13, 12-14, 12-15, 12-16, 12-17, 12-18, 12-19, 13-14, 13-15, 13-16, 13-17, 13-18, 13-19, 14-15, 14-16, 14-17, 14-18, 14-19, 15-16, 15-17, 15-18, 15-19, 16-17, 16-18, 16-19, 17-18, 17-19, 18-19) carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

As used herein, "heteroaryl" refers to an aromatic ring radical which consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The term "arylalkyl" refers to a moiety of the formula —$R^aR^b$ where $R^a$ is an alkyl or cycloalkyl as defined above and $R^b$ is an aryl or heteroaryl as defined above.

Compounds described herein may contain one or more asymmetric centers and may thus give rise to enantiomers, diastereomers, and other stereoisomeric forms. Each chiral center may be defined, in terms of absolute stereochemistry, as (R)- or(S)—. This technology is meant to include all such possible isomers, as well as mixtures thereof, including racemic and optically pure forms. Optically active (R)- and (S)-, (−)- and (+)—, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "halogen" means fluorine, chlorine, bromine, or iodine.

A "peptide" as used herein is any oligomer of two or more natural or non-natural amino acids, including alpha amino acids, beta amino acids, gamma amino acids, L-amino acids, D-amino acids, and combinations thereof. In preferred embodiments, the peptide is ~2 to ~30 (e.g., ~2 to ~5, ~2 to ~10, ~5 to ~10, ~2 to ~17, ~5 to ~17, ~10 to ~17, ~5 to ~30, ~10 to ~30, or ~18 to ~30) amino acids in length. Typically, the peptide is 10-17 amino acids in length. In at least one embodiment, the peptide contains a mixture of alpha and beta amino acids, preferably in the pattern α3/β1.

An amino acid as used herein can be any natural or non-natural amino acid, including alpha amino acids, beta amino acids, gamma amino acids, L-amino acids, and D-amino acids. Amino acid side chains can be any amino acid side chain of such an amino acid.

An amino acid according to the present invention also includes an analogue of a natural or non-natural amino acid. An amino acid analogue is an alpha amino acid with a nonnatural side chain consisting of alkyl, cycloalkyl, aryl, cycloaryl, alkenyl, or alkynyl; or a beta3-amino acid with a side chain consisting of alkyl, cycloalkyl, aryl, cycloaryl, alkenyl, or alkynyl. As used herein, an amino acid analogue also refers to a natural or nonnatural amino acid that may be substituted for an amino acid residue in the coiled-coil without loss of function relative to the native coiled-coil sequence. Suitable amino acid analogues/substitutions include the natural amino acid substitions described in Betts & Russell, "Amino Acid Properties and Consequences of Substitutions," in Bioinformatics for Geneticists 289-316 (Michael R. Barnes & Ian C. Gray eds. 2003), which is hereby incorporated by reference in its entirety, as well as the nonnatural substitutions set forth below (all available from Sigma Aldrich) and the nonnatural substitutions described in Gfeller et al., "SwissSidechain: A Molecular and Structural Database of Non-Natural Sidechains," *Nucl. Acids Res.* 41: D327-D332 (2013), which is hereby incorporated by reference in its entirety. As will be understood by the skilled artisan, analogues in the table below that are listed as having a protecting group at the N- and/or C-terminal would be deprotected during conjugation to an adjacent residue.

| Amino Acid | Exemplary Non-Natural Analogue(s) |
| --- | --- |
| Alanine | N-Acetyl-3-(3,4-dimethoxyphenyl)-D-alanine, H-β-Ala-β-naphthalene, Albizziin, (R)-(+)-α-Allylalanine, (S)-(−)-α-Allylalanine, D-2-Aminobutyric acid, L-2-Aminobutyric acid, DL-2-Aminobutyric acid, DL-2-Aminobutyric acid, 2-Aminoisobutyric acid, α-Aminoisobutyric acid, (S)-(+)-2-Amino-4-phenylbutyric acid ethyl ester, Benzyl α-aminoisobutyrate, Boc-Abu-OH, Boc-D-Abu-OH, Boc-Aib-OH, Boc-β-(9-anthryl)-Ala-OH, Boc-β-(3-benzothienyl)-Ala-OH, Boc-β-(3-benzothienyl)-D-Ala-OH, Boc-Cha-OH, Boc-Cha-OMe, Boc-β-(2-furyl)-Ala-OH, Boc-β-(2-furyl)-D-Ala-OH, Boc-β-iodo-Ala-OBzl, Boc-β-iodo-D-Ala-OBzl, Boc-3-iodo-D-Ala-OMe, Boc-β-iodo-Ala-OMe, Boc-β-iodo-Ala-OMe, Boc-1-Nal-OH, Boc-D-1-Nal-OH, Boc-D-1-Nal-OH, Boc-2-Nal-OH, Boc-D-2-Nal-OH, (R)-Boc-3-(2-naphthyl)-β-Ala-OH, (S)-Boc-3-(2-naphthyl)-β-Ala-OH, Boc-β-phenyl-Phe-OH, Boc-3-(2-pyridyl)-Ala-OH, Boc-3-(3-pyridyl)-Ala-OH, Boc-3-(3-pyridyl)-D-Ala-OH, (S)-Boc-3-(3-pyridyl)-β-Ala-OH, Boc-3-(4-pyridyl)-Ala-OH, Boc-3-(4-pyridyl)-D-Ala-OH, Boc-β-(2-quinolyl)-Ala-OH, Boc-3-(2-quinolyl)-DL-Ala-OH, Boc-3-(3-quinolyl)-DL-Ala-OH, Boc-3-(2-quinoxalyl)-DL-Ala-OH, Boc-β-(4-thiazolyl)-Ala-OH, Boc-β-(2-thienyl)-Ala-OH, Boc-β-(2-thienyl)-D-Ala-OH, Boc-β-(3-thienyl)-Ala-OH, Boc-β-(3-thienyl)-D-Ala-OH, 3-Chloro-D-alanine methyl ester, N-[(4-Chlorophenyl)sulfonyl]-β-alanine, 3-Cyclohexyl-D-alanine, 3-Cyclopentyl-DL-alanine, (−)-3-(3,4-Dihydroxyphenyl)-2-methyl-L-alanine, 3,3-Diphenyl-D-alanine, 3,3-Diphenyl-L-alanine, N-[(S)-(+)-1-(Ethoxycarbonyl)-3-phenylpropyl]-L-alanine, N-[1-(S)-(+)-Ethoxycarbonyl-3-phenylpropyl]-L-alanyl carboxyanhydride, N-(3-fluorobenzyl)alanine, Fmoc-Abu-OH, Fmoc-3-(9-anthryl)-Ala-OH, Fmoc-β-azido-Ala-OH, Fmoc-(S)-2-(4-azidobutane)Ala-OH, Fmoc-(S)-2-(2-azidoethane)Ala-OH, Fmoc-(S)-2-(6-azidohexane)Ala-OH, Fmoc-(S)-2-(5-azidopentane)Ala-OH, Fmoc-Cha-OH, Fmoc-3-cyclopentyl-DL-Ala-OH, Fmoc-β-(2-furyl)-Ala-OH, Fmoc-β-(2-furyl)-D-Ala-OH, Fmoc-α-Me-Ala-OH, Fmoc-1-Nal-OH, Fmoc-D-1-Nal-OH, Fmoc-2-Nal-OH, Fmoc-D-2-Nal-OH, Fmoc-(S)-2-(7-octenyl)Ala-OH, Fmoc-(R)-2-(pentenyl)Ala-OH, Fmoc-(S)-2-(4-pentenyl)Ala-OH, Fmoc-β-phenyl-Phe-OH, Fmoc-(R)-2-(2-propenyl)Ala-OH, Fmoc-β-(2-pyridyl)-Ala-OH ≥97.0% (HPLC), Fmoc-β-(2-pyridyl)-D-Ala-OH, Fmoc-β-(3-pyridyl)-Ala-OH, Fmoc-β-(3-pyridyl)-D-Ala-OH, Fmoc-β-(4-pyridyl)-Ala-OH, Fmoc-β-(4-pyridyl)-D-Ala-OH, Fmoc-3-(2-quinolyl)-DL-Ala-OH, Fmoc-β-(4-thiazolyl)-Ala-OH, Fmoc-β-(2-thienyl)-Ala-OH, Fmoc-β-(3-thienyl)-Ala-OH, Fmoc-β-(3-thienyl)-D-Ala-OH, N-(3-Indolylacetyl)-L-alanine, Methyl (RS)-2-(aminomethyl)-3-phenylpropionate, 3-(2-Oxo-1,2-dihydro-4-quinolinyl)alanine, 3-(1-Pyrazolyl)-L-alanine, 3-(2-Pyridyl)-D-alanine, 3- |

-continued

| Amino Acid | Exemplary Non-Natural Analogue(s) |
| --- | --- |
|  | (2-Pyridyl)-L-alanine, 3-(3-Pyridyl)-L-alanine, 3-(4-Pyridyl)-D-alanine, 3-(4-Pyridyl)-L-alanine, 3-(2-Quinolyl)-DL-alanine, 3-(4-Quinolyl)-DL-alanine, D-styrylalanine, L-styrylalanine, 3-(2-Thienyl)-L-alanine, 3-(2-Thienyl)-DL-alanine, 3-(2-Thienyl)-DL-alanine, 3,3,3-Trifluoro-DL-alanine, 3-Ureidopropionic acid, Z-Aib-OH, Z-Cha-OH, Z-Dehydro-Ala-OMe, Z-dehydro-Ala-OH, Z-D-2-Nal-OH. |
| Isoleucine | Boc-allo-Ile-OH, D-allo-Isoleucine, D-allo-Isoleucine, DL-allo-Isoleucine. |
| Leucine | Homoleucine, N-[(2S,3R)-3-Amino-2-hydroxy-4-phenylbutyryl]-L-leucine, Boc-4,5-dehydro-Leu-OH, Boc-Ile-Osu, Cycloleucine, N-(3,5-Dinitrobenzoyl)-DL-leucine, Fmoc-tBu-Gly-OH, N-Formyl-Leu-OH, N-(3-Indolylacetyl)-L-isoleucine, D-tert-Leucine, D-tert-Leucine, L-tert-Leucine, L-tert-Leucine, DL-tert-Leucine, DL-tert-Leucine, L-tert-Leucine methyl ester, 5,5,5-Trifluoro-DL-leucine. |
| Valine | 3-Fluoro-DL-valine , 4,4,4,4',4',4'-Hexafluoro-DL-valine, (R)-(+)-α-Methylvaline, (S)-(−)-α-Methylvaline. |
| Phenylalanine | Boc-Homophenylalanine-OH, Boc-D-Homophenylalanine-OH, Fmoc-Homophenylalanine-OH, Fmoc-D-Homophenylalanine-OH, Z-Homophenylalanine-OH, Boc-(R)-β2-homophenylalanine, DL-homophenylalanine methyl ester, D-Homophenylalanine, L-Homophenylalanine, DL-Homophenylalanine, D-Homophenylalanine ethyl ester, Ac-p-bromo-DL-Phe-OH, (S)-N-acetyl-4-bromophenylalanine, N-Acetyl-2-fluoro-DL-phenylalanine, N-Acetyl-4-fluoro-DL-phenylalanine, 4-Amino-L-phenylalanine, Boc-4-azido-Phe-OH, Boc-Bpa-OH, Boc-D-Bpa-OH, Boc-4-tert-butyl-Phe-OH, Boc-4-tert-butyl-D-Phe-OH, Boc-4-(Fmoc-amino)-L-phenylalanine, rac-Boc-β2-homophenylalanine, (S)-Boc-4-methoxy-β-Phe-OH, Boc-2-nitro-L-phenylalanine, Boc-pentafluoro-D-phenylalanine, Boc-pentafluoro-L-phenylalanine, Boc-Phe(4-Br)—OH, Boc-D-Phe(4-Br)—OH, Boc-Phe(2-CF3)—OH, Boc-D-Phe(2-CF3)—OH, Boc-Phe(3-CF3)—OH, Boc-D-Phe(3-CF3)—OH, Boc-Phe(4-CF3)—OH, Boc-D-Phe(4-CF3)—OH, Boc-Phe(2-Cl)—OH, Boc-D-Phe(2-Cl)—OH, Boc-Phe(2,4-Cl2)—OH, Boc-D-Phe(2,4-Cl2)—OH, Boc-D-Phe(3-Cl)—OH, Boc-Phe(3,4-Cl2)—OH, Boc-D-Phe(3,4-Cl2)—OH, Boc-Phe(4-Cl)—OH, Boc-D-Phe(4-Cl)—OH, Boc-Phe(2-CN)—OH, Boc-D-Phe(2-CN)—OH, Boc-Phe(3-CN)—OH, Boc-D-Phe(3-CN)—OH, Boc-Phe(4-CN)—OH, Boc-D-Phe(4-CN)—OH, Boc-Phe(2-Me)—OH, Boc-D-Phe(2-Me)—OH, Boc-Phe(3-Me)—OH, Boc-D-Phe(3-Me)—OH, Boc-Phe(4-Me)—OH, Boc-Phe(4-NH2)—OH, Boc-Phe(4-NO2)—OH, Boc-D-Phe(4-NO2)—OH, Boc-Phe(2-F)—OH, Boc-D-Phe(2-F)—OH, Boc-Phe(3-F)—OH, Boc-D-Phe(3-F)—OH, Boc-Phe(3,4-F2)—OH, Boc-D-Phe(3,4-F2)—OH, Boc-Phe(3,5-F2)—OH, Boc-Phe(4-F)—OH, Boc-D-Phe(4-F)—OH, Boc-Phe(4-I)—OH, Boc-D-Phe(4-I)—OH, Boc-D-3,4,5-trifluorophenylalanine, 4-Borono-D-phenylalanine, 4-Borono-L-phenylalanine, 4-Borono-DL-phenylalanine, p-Bromo-DL-phenylalanine, 4-Bromo-L-phenylalanine, N-(tert-Butoxycarbonyl)-β-phenyl-D-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, N-[(9H-Fluoren-9-ylmethoxy)carbonyl]-2-methoxy-L-phenylalanine, o-Fluoro-DL-phenylalanine, m-Fluoro-L-phenylalanine, m-Fluoro-DL-phenylalanine, p-Fluoro-D-phenylalanine, p-Fluoro-D-phenylalanine, p-Fluoro-L-phenylalanine, p-Fluoro-DL-phenylalanine, 4-Fluoro-D-phenylalanine, 2-fluoro-L-phenylalanine methyl ester, H-p-fluoro-DL-Phe-OMe, Fmoc-Bpa-OH, Fmoc-D-Bpa-OH, Fmoc-D-3-bromophenylalanine, Fmoc-D-4-bromophenylalanine, L-Fmoc-β-(6-chloro-4-pyridinyl)alanine, Fmoc-D-3,5-difluorophenylalanine, L-Fmoc-3-fluorophenylalanine, L-Fmoc-4-fluorophenylalanine, L-Fmoc-β-(1H-5-indolyl)alanine, Fmoc-2-nitro-L-phenylalanine, Fmoc-pentafluoro-L-phenylalanine, Fmoc-Phe(4-Boc2-guanidino)-OH, Fmoc-Phe(3-Br)—OH, Fmoc-Phe(4-Br)—OH, Fmoc-Phe(2-CF3)—OH, Fmoc-D-Phe(2-CF3)—OH, Fmoc-Phe(3-CF3)—OH, Fmoc-D-Phe(3-CF3)—OH, Fmoc-Phe(4-CF3)—OH, Fmoc-D-Phe(4-CF3)—OH, Fmoc-Phe(2-Cl)—OH, Fmoc-D-Phe(2-Cl)—OH, Fmoc-Phe(2,4-Cl2)—OH, Fmoc-D-Phe(2,4-Cl2)—OH, Fmoc-Phe(3,4-Cl2)—OH, Fmoc-D-Phe(3,4-Cl2)—OH, Fmoc-Phe(4-Cl)—OH, Fmoc-D-Phe(4-Cl)—OH, Fmoc-Phe(2-CN)—OH, Fmoc-D-Phe(2-CN)—OH, Fmoc-Phe(3-CN)—OH, Fmoc-D-Phe(3-CN)—OH, Fmoc-Phe(4-CN)—OH, Fmoc-Phe(2-Me)—OH, Fmoc-Phe(3-Me)—OH, Fmoc-D-Phe(3-Me)—OH, Fmoc-Phe(4-NO2)—OH, Fmoc-D-Phe(4-NO2)—OH, Fmoc-D-Phe(2-F)—OH, Fmoc-Phe(3-F)—OH, Fmoc-D-Phe(3-F)—OH, Fmoc-Phe(3,4-F2)—OH, Fmoc-Phe(3,5-F2)—OH, Fmoc-Phe(4-F)—OH, Fmoc-D-Phe(4-F)—OH, Fmoc-Phe(4-I)—OH, Fmoc-D-Phe(4-I)—OH, Fmoc-4-(phosphonomethyl)-Phe-OH, L-Fmoc-4-trifluoromethylphenylalanine, Fmoc-3,4,5-trifluoro-D-phenylalanine, Fmoc-L-3,4,5-trifluorophenylalanine, 6-Hydroxy-DL-DOPA, 4-(Hydroxymethyl)-D-phenylalanine, N-(3-Indolylacetyl)-L-phenylalanine, p-Iodo-D-phenylalanine, 4-Iodo-L-phenylalanine, α-Methyl-D-phenylalanine, α-Methyl-L-phenylalanine, α-Methyl-DL-phenylalanine, α-Methyl-DL-phenylalanine methyl ester, 4-Nitro-D-phenylalanine, 4-Nitro-L-phenylalanine, 4-Nitro-DL-phenylalanine, (S)-(+)-4-Nitrophenylalanine methyl ester, 2-(Trifluoromethyl)-D-phenylalanine, 2-(Trifluoromethyl)-L-phenylalanine, 3-(Trifluoromethyl)-D-phenylalanine, 3-(Trifluoromethyl)-L-phenylalanine, 4-(Trifluoromethyl)-D-phenylalanine, 3,3',5-Triiodo-L-thyronine, Z-L-Phe chloromethyl ketone. |
| Tryptophan | 5-Fluoro-L-tryptophan, 5-Fluoro-DL-tryptophan, 5-Hydroxy-L-tryptophan, 5-Methoxy-DL-tryptophan, 5-Methyl-DL-tryptophan tryptophan analog, H-Tpi-Ome. |
| Tyrosine | 3-Amino-L-tyrosine, Boc-3-chloro-D-Tyr-OH, Boc-Tyr(3,5-I2)-Osu, 3-Chloro-L-tyrosine, Fmoc-Tyr(3-NO2)—OH, Fmoc-Tyr(3,5-I2)—OH, α-Methyl-DL-tyrosine, 3-Nitro-L-tyrosine, 3-Nitro-L-tyrosine ethyl ester, 3-Nitro-L-tyrosine ethyl ester, DL-o-Tyrosine. |
| Asparagine | Boc-Asn(Xan)-OH, Nα-Boc-Nβ-xanthenyl-L-asparagine. |
| Cysteine | Homocysteine, DL-Homocysteine, L-Homocysteine thiolactone, L-Homocysteine thiolactone, L-Homocystine, BOC-CYS(ME)—OH, L-Cysteic acid, L-Cysteinesulfinic acid, D-Ethionine, Fmoc-Cys(Boc-methyl)-OH, Seleno-L-cystine, S-(2-Thiazolyl)-L-cysteine, S-(4-Tolyl)-L-cysteine. |

| Amino Acid | Exemplary Non-Natural Analogue(s) |
|---|---|
| Glutamine | Boc-Cit-OH, D-Citrulline, Fmoc-Cit-OH, Thio-L-citrulline. |
| Serine | Fmoc-Homoser(Trt)—OH, Fmoc-D-Homoser(Trt)—OH, D-Homoserine, L-3-Homoserine, N-Trityl-L-homoserine, N-Benzoyl-(2R,3S)-3-phenylisoserine, D-Cycloserine, Fmoc-Gly-Val-OH, Fmoc-Ser[GalNAc(Ac)3-α-D]-OH, L-Isoserine, DL-Isoserine, DL-3-Phenylserine, N-Z-L-Homoserine lactone. |
| Threonine | Fmoc-Thr[GalNAc(Ac)3-α-D]-OH, L-allo-Threonine, D-Thyroxine. |
| Aspartic acid | (S)-(−)-4-tert-Butyl hydrogen 2-azidosuccinate, N-Z-L-aspartic anhydride. |
| Glutamic acid | (S)-5-tert-Butyl hydrogen 2-azidoglutarate, γ-Carboxy-DL-glutamic acid, 4-Fluoro-DL-glutamic acid, (4S)-4-(4-Trifluoromethyl-benzyl)-L-glutamic acid. |
| Arginine | L-Homoarginine hydrochloride unnatural arginine analog, L-2-Amino-3-guanidinopropionic acid, L-2-Amino-3-guanidinopropionic acid hydrochloride, 4-Guanidinobutyric acid, 3-Guanidinopropionic acid. |
| Histidine | N-Boc-3-(3-methyl-4-nitrobenzyl)-L-histidine methyl ester. |
| Lysine | (S)-(−)-1-[N-(1-Ethoxycarbonyl-3-phenylpropyl)-N-trifluoroacetyl]-L-lysine, Fmoc-β-Lys(Boc)-OH, Fmoc-Lys(palmitoyl)-OH, DL-5-Hydroxylysine, (5R)-5-Hydroxy-L-lysine. |
| Glycine | Fmoc-allyl-Gly-OH, Fmoc-propargyl-Gly-OH, (±)-Boc-α-phosphonoglycine trimethyl ester, Fmoc-D-propargyl-Gly-OH, Fmoc-D-allyl-Gly-OH, Boc-D-allyl-Gly-OH, Boc-allyl-Gly-OH, Boc-D-Chg-OH, Boc-Chg-OH, N-Fmoc-iminodiacetic acid, Di-tert-butyl-iminodicarboxylate, N-Boc-iminodiacetic acid, N-(2-Hydroxyethyl)iminodiacetic acid, Iminodiacetic acid, Fmoc-N-(1-Boc-4-piperidyl)glycine, N-Lauroylsarcosine, D-α-Cyclohexylglycine, L-α-Neopentylglycine, L-C-Propargylglycine, Sarcosine, Z-D-Chg-OH, (±)-Z-α-Phosphonoglycine trimethyl ester, Sarcosine, N-(Phosphonomethyl)glycine, Z-α-Phosphonoglycine trimethyl ester, N-[Bis(methylthio)methylene]glycine methyl ester, N-(2-Furoyl)glycine, N-(2-Furfurylideneacetyl)glycine methyl ester, N-(Chloroacetyl)glycine ethyl ester, Boc-(2-indanyl)-Gly-OH, Fmoc-(2-indanyl)-Gly-OH, Fmoc-N-(2-Boc-aminoethyl)-Gly-OH, Fmoc-N-(4-Boc-aminobutyl)-Gly-OH, Fmoc-N-(2,4-dimethoxybenzyl)-Gly-OH, Boc-D-cyclopropylglycine, Boc-(S)-2-thienylglycine, Boc-(R)-2-thienylglycine, Boc-(S)-3-thienylglycine, Boc-(R)-3-thienylglycine, Boc-L-cyclopropylglycine, L-α-Cyclopropylglycine, Boc-propargyl-Gly-OH, D-Allylglycine, (2S,3R,4S)-α-(Carboxycyclopropyl)glycine, D-Propargylglycine, N-Boc-2-(4-trifluoromethyl-phenyl)-DL-glycine, Boc-D-propargylglycine, (S)-(+)-2-chlorophenylglycine methyl ester, (R)-N-Boc-4-fluorophenylglycine, (S)-N-Boc-4-fluorophenylglycine, N-(2-fluorophenyl)-N-(methylsulfonyl) glycine, N-(4-fluorophenyl)-N-(methylsulfonyl)glycine, N-(2-chlorophenyl)-N-(methylsulfonyl)glycine, Ethyl acetamidocyanoacetate, N-(4-Hydroxyphenyl)glycine. |
| Proline | trans-1-Acetyl-4-hydroxy-L-proline, N-[3-(Acetylthio)-(2S)-methylpropionyl]-L-proline, (S)-α-Allyl-proline, Boc-(S)-α-allyl-Pro-OH, Boc-allyl-DL-Pro-OH, N-Boc-cis-4-azido-L-proline, Boc-(S)-α-benzyl-Pro-OH, Boc-α-(2-bromobenzyl)-DL-Pro-OH, Boc-α-(4-bromobenzyl)-DL-Pro-OH, Boc-α-(2-chlorobenzyl)-DL-Pro-OH, Boc-α-(3-chlorobenzyl)-DL-Pro-OH, N-Boc-4-(2,2-difluorocyclopropyl)-L-proline, Boc-α-(diphenylmethyl)-DL-Pro-OH, Boc-(R)-α-(4-fluorobenzyl)-Pro-OH, Boc-(S)-α-(4-fluorobenzyl)-Pro-OH, Boc-α-(4-fluorobenzyl)-DL-Pro-OH, N-Boc-cis-4-N-Fmoc-amino-L-proline, N-Boc-trans-4-N-Fmoc-amino-L-proline, N-Boc-cis-4-hydroxy-D-proline, N-Boc-cis-4-hydroxy-L-proline, N-Boc-trans-4-hydroxy-D-proline, N-Boc-cis-4-hydroxy-L-proline methyl ester, N-Boc-trans-4-hydroxy-L-proline methyl ester, N-Boc-4-hydroxy-D-pyrrolidine lactone, N-Boc-4-hydroxy-L-pyrrolidine lactone, Boc-Hyp(Bzl)-OH, Boc-Hyp-OH, Boc-α-Me-DL-Pro-OH, Boc-α-(4-methylbenzyl)-DL-Pro-OH, Boc-α-(1-naphthylmethyl)-DL-Pro-OH, N-Boc-2-piperidinecarboxylic acid, (R)-(+)-N-Boc-2-piperidinecarboxylic acid, Boc-Pip-OH, Boc-α-propyl-DL-Pro-OH, Boc-α-(2-propynyl)-L-proline, Boc-(R)-4-(2-propynyl)-L-proline, N-Boc-trans-4-(p-tosyloxy)-L-proline methyl ester, Boc-(R)-4-[2-(trifluoromethyl)benzyl]-L-proline, Boc-(R)-4-[4-(trifluoromethyl)benzyl]-L-proline, Boc-(R)-α-(4-trifluoromethylbenzyl)-Pro-OH, Boc-(S)-α-(4-trifluoromethylbenzyl)-Pro-OH, 3,4-Dehydro-L-proline, 3,4-Dehydro-DL-proline, Fmoc-Hyp-OH, Fmoc-Hyp(tBu)—OH, Fmoc-Pip-OH, Fmoc-D-Pip-OH, cis-3-Hydroxy-DL-proline, cis-4-Hydroxy-D-proline, cis-4-Hydroxy-L-proline collagen synthesis inhibitor, trans-4-Hydroxy-D-proline, trans-4-Hydroxy-L-proline, trans-4-Hydroxy-L-proline, L-4-Hydroxy-proline benzyl ester hydrochloride, L-4-Hydroxyproline methyl ester, (S)-(+)-Methyl indoline-2-carboxylate, α-Methyl-L-proline, (S)-1-Z-4-oxopyrrolidine-2-carboxylic acid, L-Pipecolic acid, L-Pipecolic acid Proline homolog, Pipecolinic acid, D-Pipecolinic acid, Z-Hyp-OH. |

Non-limiting examples of substitutions for certain amino acid residues include, without limitation, those shown below.

| Amino Acid | Examplary Substition |
|---|---|
| Serine | Threonine |
| Tyrosine | Phenylalanine |
| Aspartic acid | Phosphoserine |
| Glutamic acid | Phosphoserine |
| Lysine | arginine, ornithine, diaminoproprionic acid, diaminobutyric acid |
| Arginine | Lysine |

The amino acids according to the present invention may also be optionally modified. Modifications include, for example, phosphorylation (e.g., phosphoserine, phosphotyrosine, phosphothreonine), halogenation (esp. with 3-9 halogens) (preferably with fluorine, e.g., hexafluoroleucine, hexafluorovaline), methylation (e.g., aspartic acid methyl ester, glutamic acid methyl ester, methyllysine, dimethyllysine, trimethyllysine, dimethylarginine, methylarginine, methyltryptophan), and acetylation (e.g., acetyllysine).

In at least one embodiment of the present invention, (1) at least $f_0$, $g_0$, $a_1$, $b_1$, $c_1$, $d_1$, $e_1$, $f_1$, $g_1$, $a_2$, $b_2$, $C_2$, $d_2$, and $e_2$ are present in the first coil and at least $g'_0$, $a'_0$, $b'_0$, $c'_0$, $d'_0$, $e'_0$, $f_1$, $g'_0$, $a'_2$, $b'_2$, $c'_2$, $d'_2$, $e'_2$, and $f'_2$ are present in the second coil; or (2) at least $f_1$, $g_1$, $a_2$, $b_2$, $c_2$, $d_2$, $e_2$, $f_2$, $g_2$, $a_3$, $b_3$, $c_3$, $d_3$, and $e_3$ are present in the first coil and at least $g'_0$, $a'_2$, $b'_2$, $c'_2$, $d'_2$, $e'_2$, $f'_2$, $g'_2$, $a'_3$, $b'_3$, $c'_3$, $d'_3$, $e'_3$, and $f'_3$ are present in the second coil.

In at least one embodiment of the present invention, each residue independently has the formula

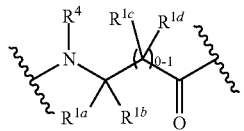

wherein:
$R^{1a}$, $R^{1b}$, $R^{1c}$, and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, $-OR^5$, or $-SR^5$; and wherein when a linker covalently binds to a residue, the linker is attached to or replaces one of $R^{1a}$, $R^{1b}$, $R^{1c}$, and $R^{1d}$, each $R^4$ is independently hydrogen, an alkyl, an alkenyl, an alkynyl, a cycloalkyl, a heterocyclyl, an aryl, a heteroaryl, or an arylalkyl; and each $R^5$ is independently selected from the group consisting of H, —PG (where PG is a protecting group), an alkyl, an alkenyl, an alkynyl, a cycloalkyl, an aryl, a heteroaryl, a heterocyclyl, and an arylalkyl.

As will be apparent to the skilled artisan, the linkers in accordance with the present invention create a covalent bridge between an amino acid residue/analogue on one coil of the coiled-coil structure and an amino acid residue/analogue on the other coil in the coiled-coil structure. As will be apparent to the skilled artisan, virtually any covalent linker can be used, provided the appropriate spatial distance between the two linked residues is maintained. The spatial distance as used herein refers to the distance of atoms in the coiled-coil structure when in its solid state, as determined using a static molecular modeling program (e.g., UCSF Chimera) and/or by evaluating the crystal structure of the macrocycle. For linkers between residue pairs $g_0$-$e'_0$, $g_1$-$e'_2$, $g_2$-$e'_3$, $e_1$-$g'_0$, $e_2$-$g'_0$, and $e_3$-$g'_2$ the appropriate spatial distance is 10-25 Å (10-11, 10-12, 10-13, 10-14, 10-15, 10-16, 10-17, 10-18, 10-19, 10-20, 10-21, 10-22, 10-23, 10-24, 11-12, 11-13, 11-14, 11-15, 11-16, 11-17, 11-18, 11-19, 11-20, 11-21, 11-22, 11-23, 11-24, 11-25, 12-13, 12-14, 12-15, 12-16, 12-17, 12-18, 12-19, 12-20, 12-21, 12-22, 12-23, 12-24, 12-25, 13-14, 13-15, 13-16, 13-17, 13-18, 13-19, 13-20, 13-21, 13-22, 13-23, 13-24, 13-25, 14-15, 14-16, 14-17, 14-18, 14-19, 14-20, 14-21, 14-22, 14-23, 14-24, 14-25, 15-16, 15-17, 15-18, 15-19, 15-20, 15-21, 15-22, 15-23, 15-24, 15-25, 16-17, 16-18, 16-19, 16-20, 16-21, 16-22, 16-23, 16-24, 16-25, 17-18, 17-19, 17-20, 17-21, 17-22, 17-23, 17-24, 17-25, 18-19, 18-20, 18-21, 18-22, 18-23, 18-24, 18-25, 19-20, 19-21, 19-22, 19-23, 19-24, 19-25, 20-21, 20-22, 20-23, 20-24, 20-25, 21-22, 21-23, 21-24, 21-25, 22-23, 22-24, 22-25, 23-24, 23-25, or 24-25 Å). In at least one embodiment, the spatial distance is 11-17 Å. In at least one embodiment, the spatial distance is 15-20 Å. For linkers between residue pairs $d_1$-$d'_0$, $d_2$-$d'_2$, $d_3$-$d'_3$, $a_1$-$a'_0$, $a_2$-$a'_2$, and $a_3$-$a'_3$ the appropriate spatial distance is 5-15 Å (5-6, 5-7, 5-8, 5-9, 5-10, 5-11, 5-12, 5-13, 5-14, 6-7, 6-8, 6-9, 6-10, 6-11, 6-12, 6-13, 6-14, 6-15, 7-8, 7-9, 7-10, 7-11, 7-12, 7-13, 7-14, 7-15, 8-9, 8-10, 8-11, 8-12, 8-13, 8-14, 8-15, 9-10, 9-11, 9-12, 9-13, 9-14, 9-15, 10-11, 10-12, 10-13, 10-14, 10-15, 11-12, 11-13, 11-14, 11-15, 12-13, 12-14, 12-15, 13-14, 13-15, or 14-15 Å). In at least one embodiment, the spatial distance is 6-8 Å. In at least one embodiment, the spatial distance is 5-10 Å. Methods of modifying amino acid residues to facilitate attachment of a suitable linker (including replacement of an amino acid side chain with the linker) will also be apparent to the skilled artisan.

In at least one embodiment of the present invention, the length of any linker between residue pairs $g_0$-$e'_0$, $g_1$-$e'_2$, $g_2$-$e'_3$, $e_1$-$g'_0$, $e_2$-$g'_0$, and $e_3$-$g'_2$ is such that the spatial distance between the Cα positions of each residue in the pair is 10-25 Å; and the length of any linker between residue pairs $d_1$-$d'_0$, $d_2$-$d'_2$, $d_3$-$d'_3$, $a_1$-$a'_0$, $a_2$-$a'_2$, and $a_3$-$a'_3$ is such that the spatial distance between the Cα positions of each residue in the pair is 5-15 Å.

In a preferred embodiment, the two amino acids/analogues may be covalently connected to each other using alkylene, alkenylene, arylene, heteroarylene, ethers, thioethers, amides, maleimides, esters, disulfides, diselenides, —O—, —S—, —Se—, and any combination thereof. As will be apparent to the skilled artisan, the linkers may be symmetrical or asymmetrical.

Suitable examples of linkers between residue pairs $g_0$-$e'_0$, $g_1$-$e'_2$, $g_2$-$e'_3$, $e_1$-$g'_0$, $e_2$-$g'_1$, and $e_3$-$g'_2$ include, without limitation, those having the formula —Zn—, wherein n is a number from 1 to 25 (1, 2, 3, 4, 5, 6, 7, 8, 9, 10, 11, 12, 13, 14, 15, 16, 17, 18, 19, 20, 21, 22, 23, 24, 25, or any range within 1 and 25, including, e.g., 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 6-10, 6-15, 6-20, 6-25, 7-10, 7-15, 7-20, 7-25, 8-10, 8-15, 8-20, 8-25, 9-10, 9-15, 9-20, 9-25, 10-15, 10-20, 10-25, 11-15, 11-20, 11-25, 12-15, 12-20, 12-25, 13-15, 13-20, 13-25, 14-15, 14-20, 14-25, 15-20, 15-25, 16-20, 16-25, 17-20, 17-25, 18-20, 18-25, 19-20, 19-25, 20-25, 21-25, 22-25, 23-25, 24-25; in at least one embodiment, n is 5-25) and each Z is independently selected at each occurrence thereof from the group consisting of alkylene, alkenylene, arylene, heteroarylene (esp. triazole-diyl, thiazole-diyl, oxazole-diyl), ethers, amides, esters, maleimides, thioethers, O, S, and Se. Suitable examples of symmetrical linkers include, without limitation,

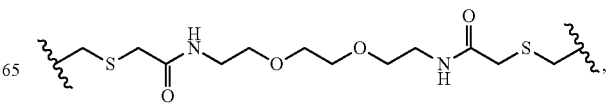

-continued

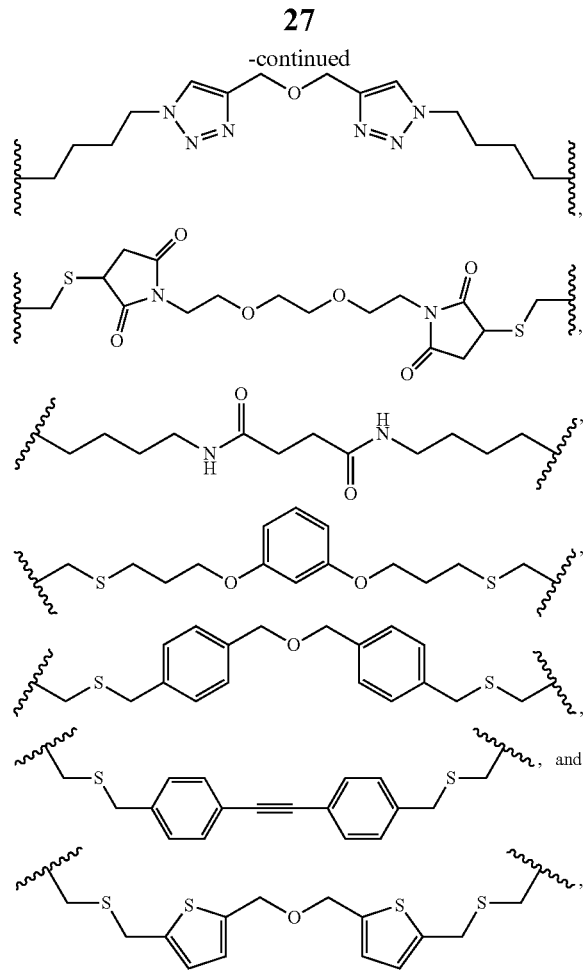

wherein each

marks a connection point to the Cα carbon in a linked residue/analogue.

In at least one embodiment of the present invention, a linker between at least one of residue pairs $g_0$-$e'_1$, $g_1$-$e'_2$, $g_2$-$e'_3$, $e_1$-$g'_0$, $e_2$-$g'_1$, and $e_3$-$g'_2$ has a formula selected from (a) the group consisting of:

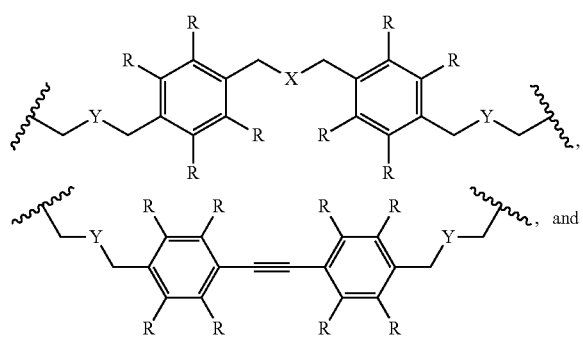

-continued

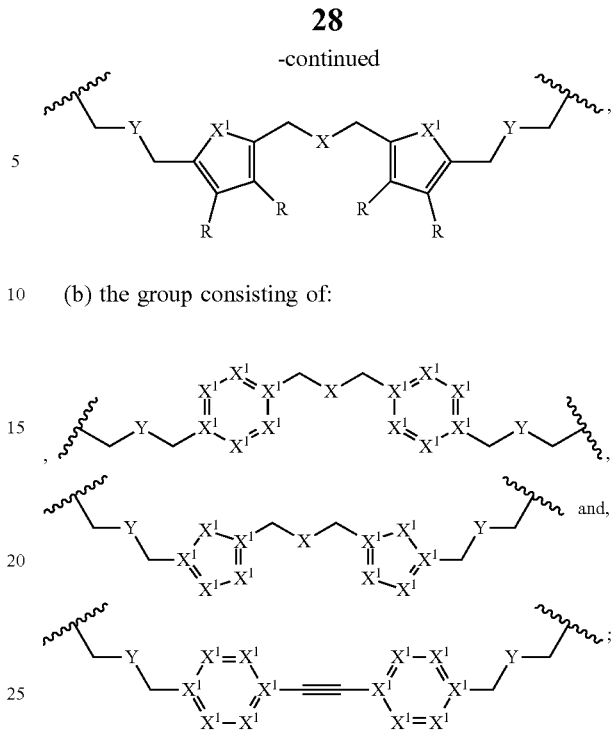

(b) the group consisting of:

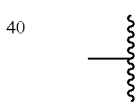

wherein:
X in group (a) and group (b) is O, S, $CR_2$, NR, or P (preferably O, S, $CH_2$ or NR);
each $X^1$ in group (a) is independently O, S, NH, or NR;
each $X^1$ in group (b) is independently O, S, C, CR, N, NH, or NR;
each R in group (a) and group (b) is independently H, alkyl, or aryl; and
each Y in group (a) and group (b) is S; and wherein each

marks a connection point to the Cα carbon in a linked residue/analogue.

As will be apparent to the skilled artisan, the parallel coiled-coil structures according to the present invention can each contain anywhere from only one of the linkers to all of the linkers. In at least one preferred embodiment, only one linker is present. In at least one embodiment of the parallel coiled-coil structures, at least one linker between a g-e' pair or between an e-g' pair is present and at least one linker between a d-d' pair or between an a-a' pair is present. Typically, the coiled-coil structures will contain the minimum number of linkers necessary to stabilize the helicity of the coiled-coil. This number will vary depending on the general stability of the native coiled-coil, as will be apparent to the skilled artisan. In a preferred embodiment, only one linker is present. In another preferred embodiment, only two linkers are present.

In at least one embodiment of the present invention, a linker between at least one of residue pairs $g_0$-$e'_1$, $g_1$-$e'_2$, $g_2$-$e'_3$, $e_1$-$g'_0$, $e_2$-$g'_1$, and $e_3$-$g'_2$ is present.

In at least one embodiment of the present invention, a linker between at least one of residue pairs $a_1$-$a'_1$, $a_2$-$a'_2$, $a_3$-$a'_3$, $d_1$-$d'_1$, $d_2$-$d'_2$, and $d_3$-$d'_3$ is present.

In at least one embodiment of the present invention, a linker between at least one of residue pairs $a_1$-$a'_1$, $a_2$-$a'_2$, $a_3$-$a'_3$, $d_1$-$d'_1$, $d_2$-$d'_2$, and $d_3$-$d'_3$ is selected from the group consisting of disulfides, diselenides, $C_{1-8}$ alkylene, $C_{2-8}$ alkenylene, arylene, heteroarylene, triazole-diyl, and thiazole-diyl.

In at least one embodiment of the present invention, a linker between at least one of residue pairs $a_1$-$a'_1$, $a_2$-$a'_2$, $a_3$-$a'_3$, $d_1$-$d'_1$, $d_2$-$d'_2$, and $d_3$-$d'_3$ is a disulfide bond from a cysteine or homocysteine residue, a diselenide from a selenocysteine residue, an alkylene from an allylglycine residue, or an arylene linker.

In at least one embodiment, there is a linker present between $X_{14}$ and $X'_8$ and/or between $X_7$ and $X'_1$.

In at least one embodiment of the present invention, the parallel coiled-coil is of Formula III:

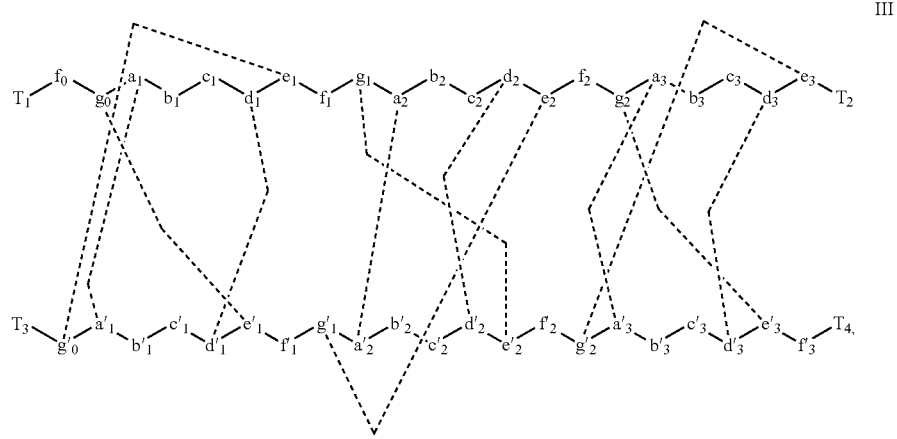

III wherein:
each dotted line represents, independently, an optional linker and
each residue independently has the formula

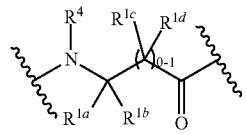

wherein:
$R^{1a}$, $R^{1b}$, $R^{1c}$, and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —$OR^5$, or —$SR^5$; and wherein when a linker covalently binds to a residue, the linker is attached to or replaces one of $R^{1a}$, $R^{1b}$, $R^{1c}$, and $R^{1d}$.

each $R^4$ is independently hydrogen, an alkyl, an alkenyl, an alkynyl, a cycloalkyl, a heterocyclyl, an aryl, a heteroaryl, or an arylalkyl; and each $R^5$ is independently selected from the group consisting of H, —PG (where PG is a protecting group), an alkyl, an alkenyl, an alkynyl, a cycloalkyl, an aryl, a heteroaryl, a heterocyclyl, and an arylalkyl.

In at least one embodiment of the present invention, at least one of the following conditions is met: (A) in at least one a, a', d, or d' residue, (i) one of $R^{1a}$ and $R^{1c}$ is the side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues, and (ii) $R^{1b}$, $R^{1d}$, and the other of $R^{1a}$ and $R^{1c}$ are each independently hydrogen, a $C_{1-3}$ alkyl, or a $C_{2-3}$ alkenyl; (B) in at least one e, e', g, or g' residue, (i) one of $R^{1a}$ and $R^{1c}$ is an amino acid side chain and (ii) $R^{1b}$, $R^{1d}$, and the other of $R^{1a}$ and $R^{1c}$ are each independently hydrogen or a $C_{1-3}$ alkyl.

Figure 16:
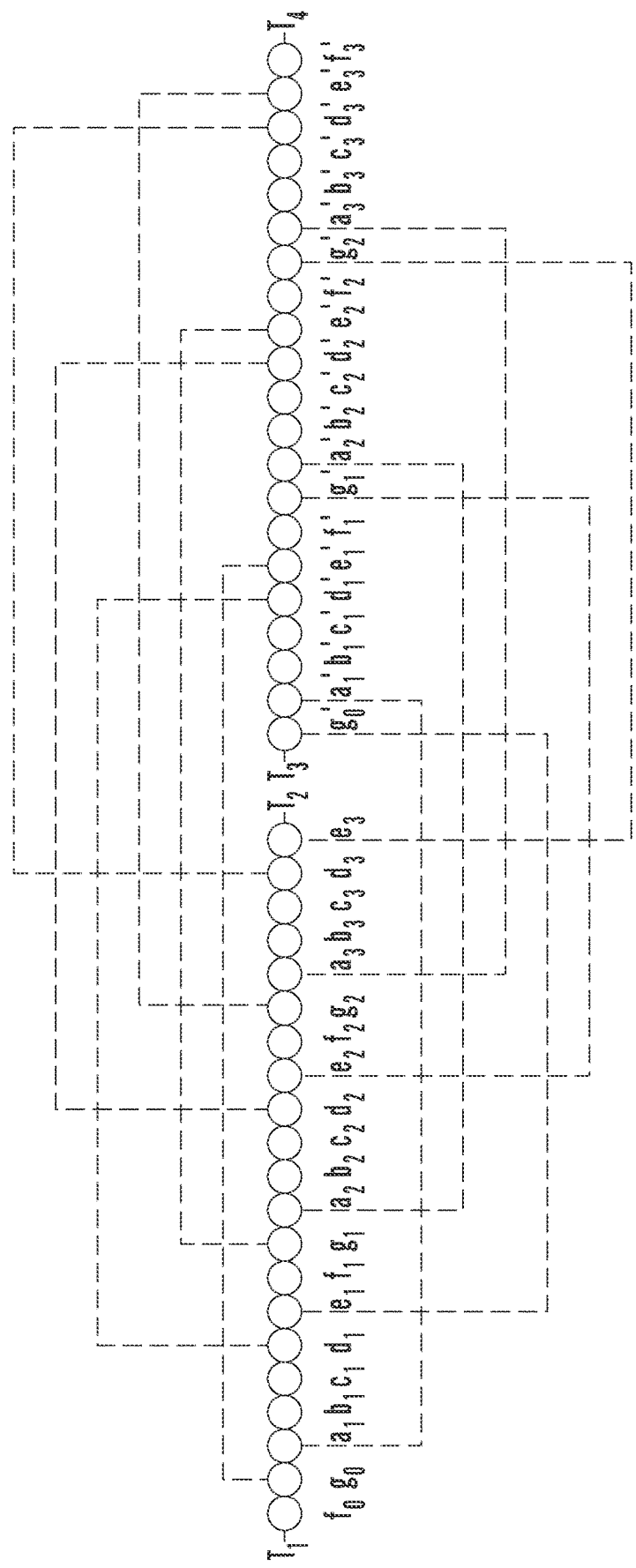
FIG. 16 shows the macrostructure of a parallel coiled-coil structure.

In at least one embodiment of the present invention, the parallel coiled-coil has the formula set forth in FIG. 16.

In at least one embodiment of the present invention, the macrostructure is $CHD3^{NEMO}$.

Protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G. M. WUTS, PROTECTIVE GROUPS IN ORGANIC SYNTHESIS 494-615 (1999), which is hereby incorporated by reference in its entirety. Suitable protecting groups according to this and all aspects of the present invention include, e.g., tert-butyloxycarbonyl ("Boc"), 9-fluorenylmethyloxycarbonyl ("Fmoc"), carbobenzyloxy ("Cbz"), and trityl. Protecting groups that are suitable for the protection of an alcohol are also well known in the art. Suitable alcohol protecting groups include, without limitation, silyl ethers, esters, and alkyl/aryl ethers. Protecting groups that are suitable for the protection of a thiol group are also well known in the art. Suitable thiol protecting groups include, without limitation, aryl/alkyl thio ethers and disulfides. As will be apparent to those of ordinary skill in the art, amino acid side chains of Asn, Asp, Gln, Glu, Cys, Ser, His, Lys, Arg, Trp, or Thr will typically need to be protected while carrying out the methods described herein. Protecting groups that are suitable for protecting these amino acid side chains are also well known in the art. Methods of protecting and deprotecting functional groups vary depending on the chosen protecting group; however, these methods are well known in the art and described in THEODORA W. GREENE & PETER G. M. WUTS, PROTECTIVE GROUPS IN ORGANIC SYNTHESIS 372-450 and 494-615 (1999), which is hereby incorporated by reference in its entirety.

A "tag" as used herein includes any labeling moiety that facilitates the detection, quantitation, separation, and/or purification of the compounds of the present invention. Suitable tags include purification tags, radioactive or fluorescent labels, and enzymatic tags.

Purification tags, such as poly-histidine ($His_{6-}$), a glutathione-S-transferase (GST–), or maltose-binding protein (MBP–), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}I$, $^{131}I$, $^{111}In$, or $^{99}TC$. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, and Texas Red. The fluorescent labels can be conjugated to the compounds using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., Methods for the Preparation of Enzyme—Antibody Conjugates for Use in Enzyme Immunoassay, in METHODS IN ENZYMOLOGY 147-66 (Langone et al. eds., 1981), which is hereby incorporated by reference in its entirety.

A targeting moiety according to the present invention functions to (i) promote the cellular uptake of the compound, (ii) target the compound to a particular cell or tissue type (e.g., signaling peptide sequence), or (iii) target the compound to a specific sub-cellular localization after cellular uptake (e.g., transport peptide sequence).

To promote the cellular uptake of a compound of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem.* 6:2242-55 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of a compound is an "importation competent" signal peptide as disclosed by U.S. Pat. No. 6,043,339 to Lin et al., which is hereby incorporated by reference in its entirety. An importation competent signal peptide is generally about 10 to about 50 amino acid residues in length-typically hydrophobic residues—that render the compound capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1 (1): 41-42 (1987), which is hereby incorporated by reference in its entirety).

Another suitable targeting moiety is a signal peptide sequence capable of targeting the compounds of the present invention to a particular tissue or cell type. The signaling peptide can include at least a portion of a ligand binding protein. Suitable ligand binding proteins include high-affinity antibody fragments (e.g., Fab, Fab' and $F(ab')_2$, single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified compound is delivered intravenously or otherwise introduced into blood or lymph, the compound will adsorb to the targeted cell, and the targeted cell will internalize the compound. For example, if the target cell is a cancer cell, the compound may be conjugated to an anti-$C_3B(I)$ antibody as disclosed by U.S. Pat. No. 6,572,856 to Taylor et al., which is hereby incorporated by reference in its entirety. Alternatively, the compound may be conjugated to an alphafeto protein receptor as disclosed by U.S. Pat. No. 6,514,685 to Moro, which is hereby incorporated by reference in its entirety, or to a monoclonal GAH antibody as disclosed by U.S. Pat. No. 5,837,845 to Hosokawa, which is hereby incorporated by reference in its entirety. For targeting a compound to a cardiac cell, the compound may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J. Proteom. Res.* 9:1610-18 (2010), which is hereby incorporated by reference in its entirety), cardiac troponin I, connexin-43, or any cardiac cell-surface membrane receptor that is known in the art. For targeting a compound to a hepatic cell, the signaling peptide may include a ligand domain specific to the hepatocyte-specific asialoglycoprotein receptor. Methods of preparing such chimeric proteins and peptides are described in U.S. Pat. No. 5,817,789 to Heartlein, et al., which is hereby incorporated by reference in its entirety.

Another suitable targeting moiety is a transport peptide that directs intracellular compartmentalization of the compound once it is internalized by a target cell or tissue. For transport to the endoplasmic reticulum (ER), for example, the compound can be conjugated to an ER transport peptide sequence. A number of such signal peptides are known in the art, including the signal peptide MMSFVSLLLVGIL-FYATEAEQLTKCEVFQ (SEQ ID NO: 19). Other suitable ER signal peptides include the N-terminus endoplasmic reticulum targeting sequence of the enzyme 17β-hydroxysteroid dehydrogenase type 11 (Horiguchi et al., "Identification and Characterization of the ER/Lipid Droplet-Targeting Sequence in 17β-hydroxysteroid Dehydrogenase Type 11," *Arch. Biochem. Biophys.* 479 (2): 121-30 (2008), which is hereby incorporated by reference in its entirety), or any of the ER signaling peptides (including the nucleic acid sequences encoding the ER signal peptides) disclosed in U.S. Patent Application Publication No. 20080250515 to Reed et al., which is hereby incorporated by reference in its entirety. Additionally, the compound of the present invention can contain an ER retention signal, such as the retention signal KEDL (SEQ ID NO: 20). Methods of modifying the compounds of the present invention to incorporate transport peptides for localization of the compounds to the ER can be carried out as described in U.S. Patent Application Publication No. 20080250515 to Reed et al., which is hereby incorporated by reference in its entirety. For transport to the nucleus, the compounds of the present invention can include a nuclear localization transport signal. Suitable nuclear transport peptide sequences are known in the art, including the nuclear transport peptide PPKKKRKV (SEQ ID NO: 21). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the compounds of the present invention.

Suitable transport peptide sequences for targeting to the mitochondria include MLSLRQSIRFFKPATRTLCSSRYLL (SEQ ID NO: 22). Other suitable transport peptide sequences suitable for selectively targeting the compounds of the present invention to the mitochondria are disclosed in U.S. Patent Application Publication No. 20070161544 to Wipf, which is hereby incorporated by reference in its entirety.

In some at least some embodiments of the compounds of the present invention, PG is independently selected at each occurrence thereof from the group consisting of a protecting group for protection of an amine, a protecting group for protection of a thiol, and a protecting group for protection of a carboxylic acid.

Another aspect of the present invention relates to pharmaceutical composition comprising any of the macrostructures described herein and a pharmaceutically acceptable vehicle. Acceptable pharmaceutical vehicles include solutions, suspensions, emulsions, excipients, powders, or stabilizers. The carrier should be suitable for the desired mode of delivery.

In addition, the pharmaceutical composition of the present invention may further comprise one or more pharmaceutically acceptable diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

Another aspect of the present invention is a method of inhibiting interaction between NEMO and a target molecule that binds to a helix dimer consisting of HLX1 and HLX2 of NEMO. This method involves contacting NEMO and/or the target molecule with a macrostructure as described herein under conditions effective to inhibit interaction between NEMO and the target molecule. In at least one embodiment, contacting is carried out in vivo (e.g., in a cell or a subject). In at least one embodiment, contacting is carried out in a subject and contacting comprises administering the compound to the subject.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid;

a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Another aspect of the present invention is a method of modulating transcription of a gene in a cell, wherein transcription of the gene is regulated by interaction between NEMO and a target molecule that binds to a helix dimer consisting of HLX1 and HLX2 of NEMO. This method involves contacting the cell with a macrostructure as described herein under conditions effective to modulate transcription of the gene.

The term "modulating" as it refers to expression of a gene means to increase or decrease expression and includes modulating transcription, translation, and/or post-translational processing. In at least one embodiment, modulating expression means increasing or decreasing the amount of mRNA produced. In at lease one embodiment, modulating expression means increasing or decreasing the amount of mature protein produced.

In at least one embodiment, modulating comprises down-regulating transcription of one or more genes that are typically up-regulated by NEMO and/or the target molecule, or up-regulating transcription of one or more genes that are typically down-regulated by NEMO and/or the target molecule.

In at least one embodiment of the present invention wherein modulation includes down-regulating transcription of one or more genes that are typically up-regulated by NEMO and/or the target molecule, regulation of the gene's transcription is mediated by NFκB signalling.

Suitable genes whose transcription can be modulated include, without limitation, the target genes of NFκB listed in Tables 6A-60 (FIG. 15).

In all aspects of the present invention involving contacting a cell, suitable cells include, without limitation, mammalian cells (e.g., primate cells including human cells, cat cells, dog cells, horse cells, cattle cells, goat cells, sheep cells, pig cells, mice cells, rat cells,). In at least one preferred embodiment, the cells are lymphoma cells (e.g., primary effusion lymphoma cells, diffuse large B cell lymphoma cells) or Kaposi sarcoma ("KS") (e.g., epidemic-associated KS, classic KS, endemic KS, iatrogenic KS) cells). In at least one embodiment, the cell expresses vFLIP In all aspects of the present invention involving a subject, suitable subjects include mammals (e.g., primates such as humans, cats, dogs, horses, cattle, goats, sheeps, pigs, mice, rats). In at least one preferred embodiment, the subject has lymphoma (e.g., primary effusion lymphoma, diffuse large B cell lymphoma) or KS (e.g., epidemic-associated KS, classic KS, endemic KS, iatrogenic KS).

In all aspects of the present invention directed to methods involving contacting a cell with one or more compounds, contacting can be carried out using methods that will be apparent to the skilled artisan, and can be done in vitro or in vivo.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

This liposome delivery system can also be made to accumulate at a target organ, tissue, or cell via active targeting (e.g., by incorporating an antibody or hormone on the surface of the liposomal vehicle). This can be achieved according to known methods.

An alternative approach for delivery of protein- or polypeptide-containing agents involves the conjugation of the desired agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of agents involves preparation of chimeric agents according to U.S. Pat. No. 5,817,789 to Heartlein et al., which is hereby incorporated by reference in its entirety. The chimeric agent can include a ligand domain and the agent (e.g., a compound of the invention). The ligand domain is specific for receptors located on a target cell. Thus, when the chimeric agent is delivered intravenously or otherwise introduced into blood or lymph, the chimeric agent will adsorb to the targeted cell, and the targeted cell will internalize the chimeric agent.

Compounds of the present invention may be delivered directly to the targeted cell/tissue/organ.

Additionally and/or alternatively, the compounds may be administered to a non-targeted area along with one or more agents that facilitate migration of the compounds to (and/or uptake by) a targeted tissue, organ, or cell. As will be apparent to one of ordinary skill in the art, the compound itself can be modified to facilitate its transport to a target tissue, organ, or cell and/or to facilitate its uptake by a target cell (e.g., its transport across cell membranes).

Another aspect of the present invention is a method of inhibiting NFκB signalling in a cell. This method involves contacting the cell with a macrostructure as described herein under conditions effective to inhibit NFκB signalling in the cell, wherein NFκB signalling in the cell is mediated by interaction between NEMO and a target molecule that binds to a helix dimer consisting of HLX1 and HLX2 of NEMO.

The term "inhibit" or "inhibiting" as it applies to inhibiting NFκB signalling means to suppress, decrease, diminish, or lower signaling. Inhibition can be partial or complete.

In at least one embodiment of the present invention, contacting induces apoptosis of the cell, inhibits proliferation of the cell, and/or inhibits NFκB translocation in the cell.

Suitable cells include those described above.

In at least one embodiment of the present invention, inhibiting comprises down-regulating transcription of one or more genes that are typically up-regulated by NFκB. Suitable genes include, without limitation, the target genes of NFκB listed in Tables 6A-60 (FIG. 15).

In at least one embodiment, inhibiting is carried out in a subject. Suitable subjects include those described above.

Another aspect of the present invention is a method of treating in a subject a disorder mediated by interaction between NEMO and a target molecule that binds to a helix dimer consisting of HLX1 and HLX2 of NEMO. This method involves administering to the subject a macrostructure or a pharmaceutical formulation as described herein under conditions effective to treat the disorder in the subject.

The term "treatment" or "treating" means any manner in which one or more symptoms of a disease or disorder are ameliorated or otherwise beneficially altered. Treatment also encompasses any pharmaceutical use of the compositions herein.

Suitable disorders include, without limitation lymphoma, diffuse large B cell lymphoma) and KS (e.g., epidemic-associated KS, classic KS, endemic KS, iatrogenic KS).

Suitable subjects include those described above.

In at least one embodiment of the present invention, the method includes inhibiting tumor growth in the subject.

In all aspects of the present inventions involving a target molecule, suitable target molecules include, without limitation, vFLIP.

These aspects of the present technology are further illustrated by the following examples. All references cited throughout this application, including in the drawings and Examples, are hereby incorporated by reference in their entirety.

EXAMPLES

The following examples are provided to illustrate embodiments of the present technology, but they are by no means intended to limit its scope.

Example 1—Materials and Methods

Design of NEMO mimics by AlphaSpace: AlphaSpace is a computational approach used to map the interface into a set of fragment-centric pockets (Rooklin et al., *J. Chem. Inf. Model* 55:1585-99 (2015), which is hereby incorporated by reference in its entirety). Pockets are represented as geometric "alpha clusters", which serve as 3-dimensional representations of the pocket and can be utilized to guide the selection or design of natural or non-natural residues to enhance pocket occupancy. This approach has been demonstrated previously in the optimization of a peptide inhibitor against a challenging protein-protein interaction target (Rooklin, et al., *J. Am. Chem. Soc.* 139:15560-63 (2017), which is hereby incorporated by reference in its entirety).

Figure 12:
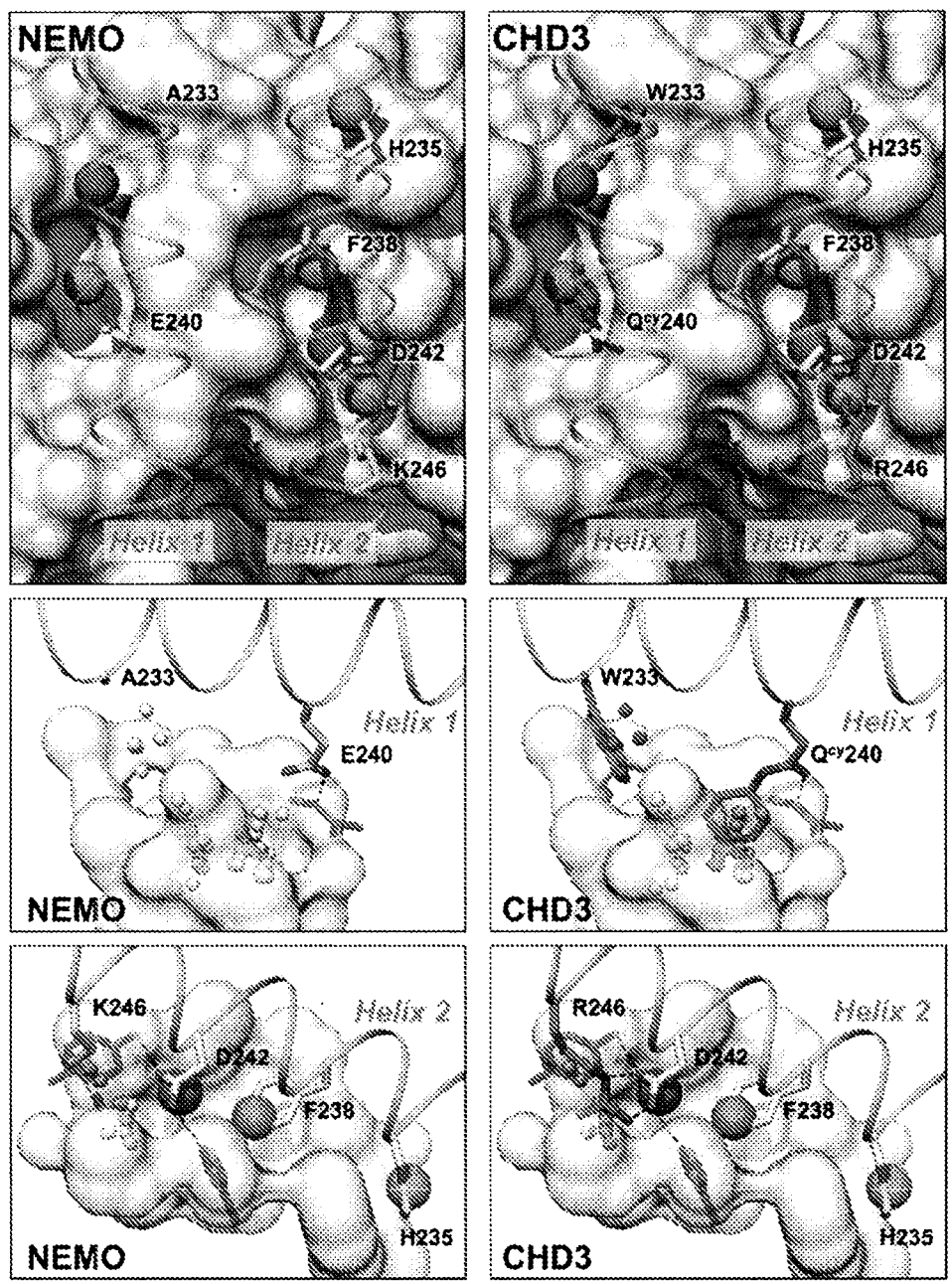
FIG. 12 is an illustration of the 6 residue-centric pockets detected on the surface of vFLIP at the NEMO interface, comparing wild type NEMO residues (on the left) and optimized CHD3$^{NEMO}$ residues (on the right). Residues are colored tan (NEMO wild type), red (CHD3$^{NEMO}$ mutants), or light blue (unmodified). Pocket centroids are indicated by large spheres and colored green (alpha-space volume>100 Å$^3$), blue (alpha-space volume>50 Å$^3$), or pink (alpha-space volume>10 Å³). The alpha-space volume correlates well with a combination of pocket surface area and curvature. In lower panels, pockets targeted by optimization are shown as alpha clusters to highlight enhanced pocket occupancy in CHD3$^{NEMO}$; occupied alpha atoms are colored green/blue by pocket and unoccupied alpha atoms are colored white. Key polar interactions are highlighted by dashed black lines with participating vFLIP residues shown in dark grey.

Starting from the vFLIP-NEMO crystal complex structure (PDB Code 3CL3) (Bagneris et al., *Mol. Cell* 30:620-31 (2008), which is hereby incorporated by reference in its entirety), vFLIP (chain A) was selected as the target interface and NEMO (chains D and E) as the template coiled coil to be optimized. Using AlphaSpace the surface of vFLIP was mapped to detect fragment-centric pockets at the NEMO interface and then the residue-centric pockets were characterized by associating alpha-atoms with their nearest residue in NEMO. This yields 6 interface pockets: 3 high-volume pockets (associated with Glu240 on Helix 1, Phe238 on Helix 2, and Lys246 on Helix 2), 2 moderate-volume pockets (associated with Ala233 on Helix 1 and Asp242 on Helix 2), and 1 low-volume pocket (associated with His235 on Helix 2). All pockets and their associated residues are illustrated are illustrated in FIG. 12.

The alpha-space volume and pocket occupancy data are listed below (Table 1). AlphaSpace calculations are calculated with the software AlphaSpace1.0 (http://www.nyu.edu/projects/yzhang/AlphaSpace/). Suggested mutations to optimize the interface were selected or designed by hand and evaluated using AlphaSpace.

TABLE 1

Pockets Detected on the Surface of vFLIP at the NEMO Interface Ranked by Alpha-Space Volumes, Along with Associated NEMO/CHD3$^{NEMO}$ Residues, and % Pocket Occupancies.

| Pocket | Binding Residue (NEMO > CHD3) | Alpha-Space Volume (Å$^3$) | % Occupancy (NEMO) | % Occupancy (CHD3) |
|---|---|---|---|---|
| 1 | Asp240 > Q$^{cy}$ | 251 | 0% | 46% |
| 2 | Phe238 | 213 | 81% | |
| 3 | Lys246 > Arg | 111 | 45% | 75% |
| 4 | Asp242 | 58 | 30% | |
| 5 | Ala233 > Trp | 52 | 0% | 55% |
| 6 | His235 | 18 | 96% | |

Helix 2 is the primary binding helix in the native vFLIP-NEMO interaction. His235 and Phe238 both exhibit high pocket occupancy with Pocket 6 and Pocket 2 respectively. Asp242 only partially occupies Pocket 4 but is well-positioned to form dual-hydrogen bonds to pocket-lining residues in vFLIP: His82 and Tyr90. Lys246, however, is not observed to engage in a polar interaction with vFLIP, nor does it extend into the adjacent pocket. It was proposed that a mutation to arginine could reinforce the hydrogen bonding network of Asp242 by forming an intrahelical salt bridge that is well-accommodated by the crystal complex, by increasing pocket occupancy, and by promoting pi-cation stabilization with Tyr90 in vFLIP.

A large volume of non-polar pocket space was detected adjacent to Helix 1 that is unoccupied in the native vFLIP-NEMO crystal complex. The moderate-volume Pocket 5 can be targeted directly by tryptophan in a high-probability rotamer state by mutating Ala233. The high-volume Pocket 1 adjacent to Glu240, however, is located beyond the reach of any natural amino acid. A non-natural cyclohexyl amine was designed as a glutamine derivative (Q$^{cy}$) to both preserve the hydrogen-bond observed between Glu240 and the backbone of pocket-lining residue Phe53 in vFLIP and to extend the cyclohexyl group into the hydrophobic vFLIP pocket with good complementarity. All three suggested mutations are integrated into the CHD3$^{NEMO}$ coiled coil mimic.

Peptide Synthesis: Peptides were synthesized on a GYROS Protein Technologies Prelude X instrument using standard Fmoc solid phase chemistry with Knorr Amide MBHA resin. Peptides were cleaved from the resin using 95% trifluoroacetic acid, 2.5% TIPS, and 2.5% H$_2$O, and purified by reversed-phase HPLC (gradient 15-60 acetonitrile/water with 0.1% TFA over 60 min) and characterized by MALDI-TOF.

Synthesis of Hydrogen-Bond Surrogate NEMO Mimic (HBS$^{NEMO}$): HBS$^{NEMO}$ was synthesized as described previously (Patgiri, et al., Org. Biomol. Chem. 8:1773-76 (2010), which is hereby incorporated by reference in its entirety). Peptide sequences up to the i+3rd residue of the parent strand were synthesized on solid phase on a GYROS Protein Technologies Prelude X instrument. A solution containing premixed o-nitrobenzesulfonyl chloride (10 eq) and 2,4,6-collidine (10 eq) in DCM was added to resin containing Fmoc-deprotected peptide. Resin was washed sequentially with dichloromethane, dimethylformamide, and diethyl ether (3×5 mL each). Resin was dried overnight under vacuum. Dried resin, PPh3, and Pd$_2$(dba)$_3$ were flushed under inert argon for 30 minutes. The resin with reactants was swelled in THF, and allymethylcarbonate was added to the reaction vessel. The solution was agitated at room temperature for 3 to 5 hours under argon to afford allylated peptide. Resin was filtered and washed with DCM, DMF, 0.2 M sodium diethylcarbamate trihydrate in NMP, and diethyl ether (3×5 mL). The nosyl protecting group was then removed by the addition of 1,8-diazabicyclo [5.4.0] undec-7-ene (DBU, 5 eq) and 2-mercaptoethanol (10 eq.) in DMF. Resin was washed with DMF, DCM, and diethyl ether (3×5 mL) and treated with the desired Fmoc amino acid (20 eq.), DIC (20 eq.), and HOAt (10 eq.) in DMF. The reaction was allowed to agitate at room temperature for 12 to 16 hours. Resin containing elongated peptide was washed, and coupled to the desired Fmoc amino acid residue (5 eq.) and 4-pentenoic acid (5 eq.) with HBTU (5 eq.) and DIEA (10 eq.) in DMF. Ring-closing metathesis of bis-olefin 9 was performed with HoveydaGrubbs II catalyst (20 mol %) in 1,2-dichloroethane under microwave irradiation at 120° C. for 10 min as previously described (Miller et al., Curr. Protoc. Chem. Biol. 6:101-16 (2014); Patgiri et al., Nat. Protoc. 5:1857-65 (2010), which are hereby incorporated by reference in their entirety). The ring-closing reaction was monitored by MALDI-TOF. Peptides were cleaved from the resin using 95% trifluoroacetic acid, 2.5% TIPS, and 2.5% H$_2$O, and purified by reversed-phase HPLC (gradient 15-60 acetonitrile/water with 0.1% TFA over 60 min) and characterized by MALDI-TOF.

Synthesis of Crosslinked Helix Dimer NEMO Mimic (CHD3$^{NEMO}$): Crosslinked helix dimers were synthesized as previously described with minor modifications (Wuo et al., J. Am. Chem. Soc. 137:11618-21 (2015), which is hereby incorporated by reference in its entirety). Parent peptide (0.25 mmol) Helix 1 was synthesized on a GYROS Protein Technologies Prelude X instrument using standard Fmoc solid phase chemistry with Knorr Amide MBHA resin. Fmoc-Glu (OAllyl)-OH was incorporated into precursor parent peptide, Helix 1. The resin bearing Helix 1 was transferred to a fritted polypropylene SPE tube and washed with DMF, DCM, and MeOH (3×5 mL). Allyl deprotection was performed using Pd(PPh$_3$)$_4$ (3 equiv) in a solution of chloroform: acetic acid: N-methylmorpholine (37:3:1). After 3 hours, the resin was washed again with DCM, DMF, MeOH (3×5 mL each). Following addition of PyBOP (3 equiv) and DIPEA (3 equiv) for 10 minutes, cyclohexylamine (6 equiv) was added resulting in Q$^{Cy}$-installed peptide. MALDI-TOF confirmed complete amidation of glutamate. The resin was washed, transferred to a microwave tube, and subsequently swelled in 3 mL of NMP and the bisalkyne propargyl ether (257 µL, 2.5 mmol, 10 equiv) was added.

A solution of CuSO$_4$ (20 mg, 0.125 mmol, 0.5 equiv) dissolved in 500 µL of water was separately prepared. To this solution, Tris [(1-benzyl-1H-1,2,3-triazol-4-yl)methyl]amine (132 mg, 0.25 mmol, 1 equiv) dissolved in 1 mL of NMP was added. This mixture was added to a solution of sodium ascorbate (495 mg, 2.5 mmol, 10 equiv) prepared in 1.5 mL of water. The resulting mixture was pipetted into the microwave tube containing propargyl ether and peptide. A magnetic stir bar was added, and the reaction mixture was subjected to microwave irradiation at 85° C. for 45 min, after which the resin was transferred to a fritted polypropylene SPE tube and washed with a 20 mM solution of sodium diethyldithiocarbamate in water (3×15 mL) followed by NMP (3×15 mL). A microcleavage of resin (95% trifluoroacetic acid, 2.5% TIPS, and 2.5% H$_2$O) showed the starting material to be consumed after one reaction. A microcleavage of resin (95% trifluoroacetic acid, 2.5% TIPS, and 2.5% H$_2$O) showed the starting material to be consumed after one reaction. Helix 2 was synthesized using the same protocol. Importantly, no copper catalyzed azide alkyne cycloaddition (CuAAC) was performed on Helix 2, leaving a functional azide handle. Each peptide was treated with a solution containing 95% trifluoroacetic acid, 2.5% TIPS, and 2.5% H$_2$O. Separately, both peptides were precipitated with cold diethyl ether and dried under a stream of nitrogen gas. HPLC purification (gradient 15-65 acetonitrile/water with 0.1% TFA over 60 min) and lyophilization yielded peptide as a white powder characterized by MALDI-TOF. Unconstrained peptide yield, sequence dependently, 25 mg of peptide from a 0.25 mmol scale.

For reaction on 1 µmol scale, purified peptides were dissolved in a ratio of 1:2 by weight (azide: alkyne) with final concentration at least 200 µM in 1 mL NMP and diluted with 1×PBS pH 7.4 (1:4) to give 4 mL of reaction solvent. 10 µL of a 10× solution of CuSO$_4$ (16 mg, 100 µmol, 100 equiv) dissolved in 1 mL of 1×PBS was prepared separately. To the CuSO4 solution, Tris [(1-benzyl-1H-1,2,3-triazol-4-yl)methyl]amine (TBTA) (2.8 mg, 5 µmol, 5 equiv) dissolved in 100 µL of NMP was added. Sodium ascorbate (10.2 mg, 50 µmol, 50 equiv.) was dissolved in 1 mL of 1×PBS. The TBTA-CuSO$_4$ solution was added to the peptide mixture, followed by sodium ascorbate solution. The reaction was allowed to proceed for 4 hours. Crude reaction mixture was filtered. HPLC purification (gradient 15-65 acetonitrile/water with 0.1% TFA over 60 min) and lyophilization yielded peptide as a white powder characterized by MALDI-TOF.

Synthesis of Fluoroscein Isothiocyanate (FITC) Labeled Peptides: Parent CHD monomers were synthesized as described above. Prior to acetyl capping, Fmoc-β-alanine was added to the N-terminus of Helix 1. Following deprotection with 20% piperidine in NMP and washing with DMF, DCM, and MeOH (3×5 mL), FITC (1.2 equiv) and DIEA (2 equiv) were added to the solid phase tube and gently agitated for 2 hours. The reaction was washed with DMF, DCM, and MeOH (3×5 mL), and characterized by MALDI-TOF. CHD synthesis and characterization proceeded as described above.

Figure 13:
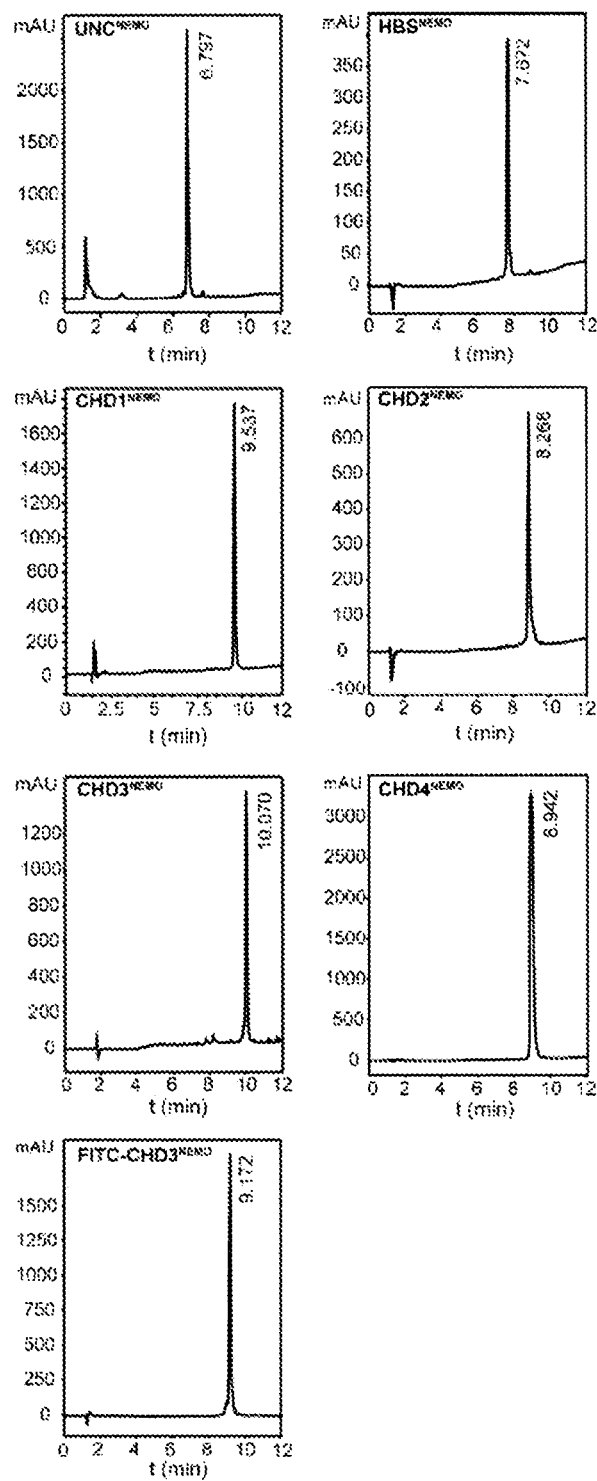
FIG. 13 shows the analytical High-performance liquid chromatography (HPLC) traces of the purified peptides.

Compound Characterization: FIG. 13 shows analytical HPLC traces of purified peptides. Table 2 shows mass spectometry analysis of synthetic peptides.

TABLE 2

Mass Spectroscopic Analysis of Synthetic Peptides

| Compound | Mass calculated, $[M + H]^+$ | Mass observed, $[M + H]^+$ |
|---|---|---|
| $UNC^{NEMO}$ | 2084.02 | 2084.36 |
| $HBS^{NEMO}$ | 2122.03 | 2122.57 |
| $CHD1^{NEMO}$ | 3840.12 | 3840.40 |
| $CHD2^{NEMO}$ | 4020.24 | 4020.16 |
| $CHD3^{NEMO}$ | 4101.33 | 4123.93 |
| $CHD4^{NEMO}$ | 3920.26 | 3920.38 |
| $FITC-CHD3^{NEMO}$ | 4517.38 | 4517.55 |

Fluorescence Polarization Assay: The relative affinity of $FITC-CHD3^{NEMO}$ to MBP-vFLIP were determined using fluorescence polarization-based direct binding assay. The polarization experiments were performed using a DTX 880 Multimode Detector (Beckman) at 25° C. with excitation and emission wavelengths of 485 and 525 nm, respectively. Each polarization experiment was performed in a 96-well round bottom plate (Greiner) in assay buffer: Tris glycerol pluronic acid. The binding affinity ($K_D$) values reported for each peptide are from experiments performed in triplicate. Raw values were fit to a signmoidal dose-response enonlinear regression model in Graphad Prism 6.0.

All binding experiments with FITC-labeled CHD peptide to MBP-vFLIP were performed under the same conditions. Briefly, serial dilutions of MBP-vFLIP were made from 75 μM into 100 nM of FITC-labeled CHD peptide in assay buffer.

$$K_D = (R_T \times (1-F_{SB}) + L_{ST} \times F_{SB}^2)/F_{SB} - L_{ST})$$

where, $R_T$=Total concentration of MBP-vFLIP; $L_{ST}$=Total concentration of FITC-CHD peptide; $F_{SB}$=Fraction of bound FITC-CHD peptide.

Circular Dichroism Spectroscopy: CD spectra were recorded on a Jasco J-1500 Circular Dichroism Spectrophotometer equipped with a temperature controller using 1 mm length cells and a scan speed of 4 nm/min at 298K. The spectra were averaged over 4 scans with the background subtracted to the analogous experimental conditions. Each sample was prepared in a 50 mM potassium fluoride solution in water (pH 7.4) to a final concentration of 20 μM. The concentrations of each peptide were determined by the UV absorption at 280 nm.

Analytical Size Exclusion Chromatography: Peptides and standards were prepared at 10 mg/mL in 2×PBS supplemented with 10% ACN. Samples were injected onto an Agilent analytical HPLC equipped with a Superdex 30 Increase 3.2/300 column (Part No. 29219758) and visualized at 220 nm. Flow rate 200 μL/min over 60 min using 2×PBS 10% ACN. The concentrations of each peptide were determined by the UV absorption at 280 nm.

Serum Stability Assay: Proteolytic stability of $CHD3^{NEMO}$ was determined using 25% fetal bovine serum in RPMI. Time points of 30 minutes, 1 hr, 2 hr, 8 hr, and 24 hrs were analyzed in triplicate. Each reaction was started upon addition of FBS to 60 μM peptide. Reactions were quenched at time points with addition of 100% EtOH, chilled on ice for 10 minutes, and pelleted at 12,000 RPM. Supernatant was injected onto an Agilent analytical HPLC equipped with an XTerra RP18 3.5 μm 2.1×150 mm column (Part No. 186000410) and visualized at 220 nm. Integration of peak areas was used to determine percent degradation of peptides. Mass of cleaved products were determined using Matrix assisted laser desorption ion time of flight (MALDI-TOF) spectroscopy.

Cell Lines and Culture Conditions: BC1 and BC3 PEL cell lines were established from lymphomatous effusions as described previously (Cesarman, 1995; Arvanitakis, 1996). BCBL-1 was obtained from the AIDS and Cancer Specimen Bank. Namalwa Burkitt lymphoma cell line was purchased from American Type Culture Collection (ATCC). Cells were grown in RPMI 1640 (GE Healthcare) supplemented with 10% (Namalwa) or 20% heat-inactivated FBS (Atlanta Biologicals) and 50 ug/ml of gentamicin (Atlanta Biologicals). vFLIP WT and NF-kB dead inducible cell lines were established by cloning WT FLAG-tagged vFLIP and mutant vFLIP into cloned pLVX-Tetone-puro vector backbone which is a component of the XLenti-X™ Tet-One™ Inducible Expression system (Clontech). Mutant vFLIP contains three amino acids mutation at position 57 where 3 amino acids ECL are replaced with three alanines, AAA. These plasmids were packaged in 293T cells and lentiviral particles were used to transduce parental Namalwa cell line. Stable transduced cell lines were established by puromycin selection at 1 μg/mL. Induction of WT vFLIP or mutant vFLIP expression was attained by adding doxycycline (Sigma) at 1 μg/mL.

The double reporter cell line BC3NFRen-luc #3 was generated by transduction of this cell line using a lentiviral construct expressing renilla luciferase controlled by a constitutive promoter (retroviral LTR). These cells were maintained in RPMI-1640 supplemented with 20% FBS and 50 μg/mL Gentamicin, as well as 1.2 mg/mL Geneticin or G418 (Life Technologies) to maintain clonal selection.

Protein Expression and Purification: vFLIP (1-178) and NEMO (150-272) were cloned into pET28a vector. his-NEMO pET28a (150-272) and pET28a his-MBP vFlip (1-178) were transformed into BL21 (DE3) cells (Invitrogen) and plated on kanamycin plates. Colonies were picked and cultured in LB broth containing kanamycin (50 μg/ml). Cultures were inoculated to 1 liter of LB broth with kanamycin and incubated at 37° C. for 3 hours then allowed to cool down at $R_T$ for 1 hr. Cultures were placed in incubator at 18° C. and induced with 0.1 mM IPTG where optical density was 0.5 and incubated overnight with shaking. Next day, cells were pelleted and resuspended in lysis buffer and lysed using microfluidizer in the presence of PMSF. Supernatants were spun down using ultracentrifuge with vaccum at 17000 rpm for 50 min (TI-45 rotor). Proteins were purified on a pre-equilibrated nickel column Ni-NTA Super Flow resin (Qiagen) and eluted using elution buffer (20 mMTris-HCl, 250 mM imidazole, 150 mM NaCl, 0.5 mM TCEP). Further purification of the protein was performed using gel filtration column (superdex200) and eluted in size exclusion buffer (20 mM Tris-HCl pH=8,150 mM NaCl, 10% glycerol and 0.5 mM TCEP). HPLC fractions were analyzed on 15% SDS-PAGE gels. Proteins were concentrated (calculated assuming an extinction coefficient), aliquoted and flash frozen at −80° C.

TR-FRET Competition Assay: For the competition assay, two fold serial dilution of the different NEMO mimetics were prepared in DMSO then diluted in TR-FRET buffer to 5× and added in triplicates to a 384 low volume well plate. His-MBP vFLIP diluted to 5× in TR-FRET buffer (250 nM) was then added to each well and incubated for 15 min at RT. His-Biotinylated NEMO diluted to 5× in TR-FRET buffer (250 nM) was then added to the mixture followed by addition of 5× or 200 nM) streptavidin-XL665 and (5× or 1 nM) of the antibody-tagged fluorophore anti-MBPK labeled with Europium cryptate). The final concentration of the NEMO mimetics ranged from 0.195 μM to 100 μM. Total assay volume was 20 μL. The plate was incubated for 1 hr at RT then read using BioTek Synergy NEO. Titration of non-biotinylated NEMO (0.0195-10 μM) was used as a positive control in every run. The effect of the peptides on vFLIP/NEMO interaction was normalized to the control and expressed as percent inhibition (% of control):

$$\% \text{ of control} = \frac{FRET_{CHD} - FRET_{background}}{FRET_{control} - FRET_{background}}$$

where FRET control is the TR-FRET signal in DMSO treated wells (highest signal) and FRET background is TR-FRET signal in wells containing the highest concentration of non-biotinylated NEMO (10 µM) which provides the lowest signal. Normalized TR-FRET data was plotted using Graphpad Prism.

Cell Viability Assays: Cell viability assays were performed by plating log-phase BC1, BC3, and BCBL-1 PEL cells or Namalwa Burkitt lymphoma cell line in RPMI complete media in serum free medium at a density of $1*10^5$ cells/mL after which cells were treated with DMSO or a range of concentrations of NEMO mimetics varying from from 5 nM to 50 µM. Media was supplemented with 20% FBS 3 hours post-peptide treatment. ATP content which correlates with metabolically active cells was measured using CellTiter-Glo kit (Promega, Madison, WI) at 24, 48 and 72 hours post-treatment. The LC50 for each NEMO mimetic in each cell line was determined using GraphPad Prism.

Figure 14:
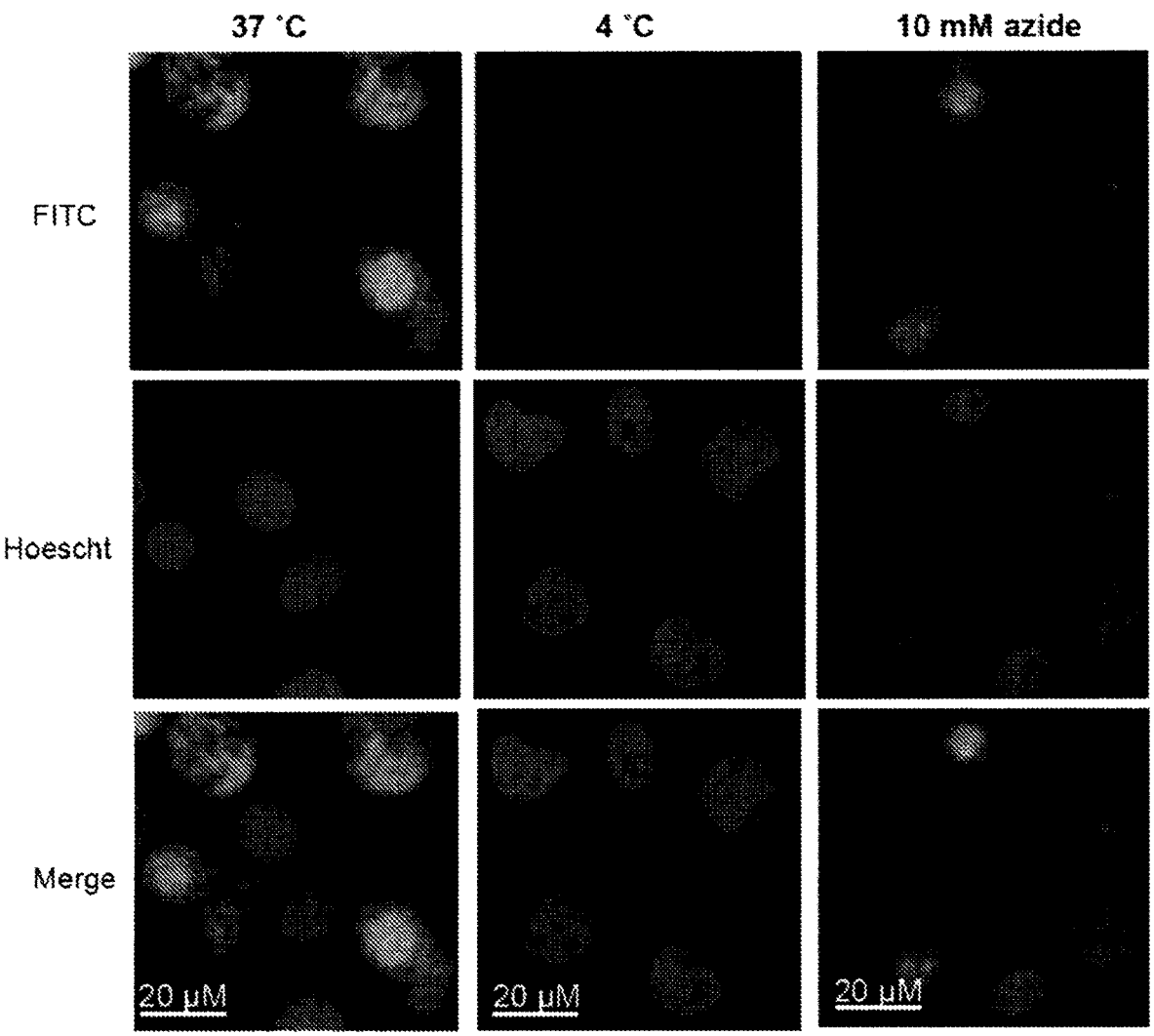
FIG. 14 shows the live confocal microscopy images of FITC-CHD3$^{NEMO}$ treated cells. Cellular uptake is visualized after 1 hr incubation period. The effect of temperature and 10 mM sodium azide on cellular uptake is observed.

Live Cell Confocal Microscopy and Analysis: BC1 PEL cells in the exponential phase were resuspended in RPMI 1640 media supplemented with 50 µg/ml gentamicin in the absence of serum and treated with a final concentration of 0.125% DMSO or 500 nM FITC-labeled peptide at 37° C., cold or in the presence of 10 mM sodium azide. Cells were then added to 35 mm glass bottom MatTek poly-lysine coated plates (p356c-0-10C) and immunofluorescence images were captured using LSM880 confocal microscope with Airyscan resolution detector, spectral detector and incubation. Images were processed using Fiji software (FIG. 14).

Exponentially growing BC-3-derived reporter cell lines (BC3-NFκB-luc #3), were resuspended in RPMI-1640 complete media plus 1.2 mg/ml selection antibiotic G418 in the absence of any serum and plated in a 96-well tissue culture microplate at $0.1*10^6$ cells/mL. Cells were then treated with DMSO or varying concentrations of NEMO peptides (at final concentration of 1 µM, 5 µM, 10 UM or 25 µM). As a positive control, BC3NFκB-luc #6 cells were treated with DMSO or 1 µM or 10 µM of the HSP90 inhibitor PU—H71 or 5 µM and 10 µM of BAY-11 in the presence of serum. 3 hours post-treatment with the different peptides, 10% FBS was added to the media. The luciferase activity was measured 5 hours and 24 hours post-treatment using Dual-Glo Luciferase assay system (Promega, Madison, WI), according to the manufacturer's instructions.

Co-Immunoprecipiation: FLAG-tagged WT vFLIP or a vFLIP NF-κB dead mutant (vFLIP$^{AAA(58-60)}$) inducible Namalwa Burkitt lymphoma cell lines were used. Expression of WT vFLIP or mutant vFLIP was attained by treating cells with 1 µg/mL doxcycline for 24 hrs. Next day, cells expressing WT vFLIP were seeded in serum-free media and treated with DMSO or increasing concentrations of NEMO peptides (at a final concentration 5 µM, 25 µM or 50 µM) in the presence of 1 µg/mL doxycycline to enable continuous expression of vFLIP. 4 hours post-treatment, media was supplemented with 20% FBS and treatment continued for another 24 hrs. Next day, uninduced Namalwa WT vFLIP cell line, treated Namalwa WT vFLIP expressing cell lines as well as Namalwa expressing mutant vFLIP and parental Namalwa cell lines were harvested, washed in PBS and lysed on ice for 30 minutes using CelLytic M lysis reagent (Sigma, cat. $C_{2978}$) supplemented with protease inhibitor cocktail (calbiochem, cat 539134). Cells were spun down and some of supernatants was saved for input and the rest was immunoprecipitated overnight using anti-FLAG M2beads (Sigma, cat. A2220) that were pre-equilibrated with the same buffer. Next day, beads were washed with CelLytic buffer five times and protein complexes were eluted using SDS lammeli buffer and boiling at 95° C.

Immunoblotting: For co-immunoprecipitation study, eluted protein lysates were separated using pre-casted 10% sodium dodecyl sulfate-polyacrylamide gel electrophoresis SDS-PAGE gel (Bio-rad). Proteins were transferred to a PVDF membrane and blocked in 5% w/v nonfat dry milk-TBST for 1 hour at room temperature. Membrane was then washed and incubated overnight with primary antibodies diluted in 5% BSA-TBST overnight. The following primary antibodies were used: FLAG antibody (1:1000) (Rockland, cat. 600-401-383), NEMO antibody (1:1000) (GeneTex, GTX107582). Secondary anti-HRP rabbit antibody was used at 1:5000 dilution (GE healthcare) and chemiluminescent signal was detected using enhanced chemiluminescence (ECL) substrate (thermo Fisher Scientific) and autoradiography.

Annexin V Staining: BC-1 cells were treated with DMSO or increasing concentrations of the CHD3$^{NEMO}$ or CHD4$^{NEMO}$ peptide for one hour in the absence of serum then 20% FBS was added 1 hr after serum starvation. Cells were harvested at 24 hrs or 48 hrs post-treatment, washed once in PBS and resuspended in Annexin V staining buffer (BD Pharmingen Catalog No. 556454) containing 3 µL/test AnnexinV-Alexa Fluor 647 (ThermoFisher A23204) and 1 µL/test DAPI (Sigma D9542) and incubated at room temperature for 15 minutes in the dark. Data were acquired with a BD LSRII analytical flow cytometer and analyzed using FlowJo software. Necrotic/late apoptotic cells were defined as Annexin V$^-$/DAPI$^+$, AnnexinV$^+$/DAPI$^+$ and early apoptotic cells were defined as Annexin V$^+$/DAPI$^-$.

PEL in Vivo Xenograft Mouse Model Study: $10 \times 10^{67}$ BC3NFRen-luc #3 were injected intraperitoneally into 4-6 week-old male NOD/SCID mice. Mice were followed by in vivo luciferase imaging using IVIS Imaging system (PerkinElmer) to confirm tumor engraftment after which mice were randomized to vehicle (n=12) and CHD3$^{NEMO}$ treated groups (n=5) with average tumor burden distributed evenly across the groups. Mice were treated intraperitoneally with vehicle (PBS-0.05% Tween-80) or with the CHD3$^{NEMO}$ peptide (20 mg/kg/day) for 9 consecutive days. The tumor burden or bioluminescence (photons/s/cm²/steradian) was monitored by live imaging and weighing, with the sacrificial endpoint determined to be a net gain or loss of 10% body weight over a week. The effect of CHD3$^{NEMO}$ on overall survival was assessed using Kaplan-Meier curves generated using GraphPad Prism software, and determined p values by analysis using log-rank (Mantel-Cox) tests.

Code availability: AlphaSpace fragment-centric topographical mapping computer code can be found at http://www.nyu.edu/projects/yzhang/AlphaSpace/.

Example 2—Design and Evaluation of NEMO Coiled Coil Mimics

We employed a target-based approach to identify inhibitors of the vFLIP-NEMO interaction (Modell et al., *Trends Pharmacol. Sci.* 37:702-13 (2016), which is hereby incorporated by reference in its entirety). We began by developing a high-throughput Time-Resolved Fluorescence Resonance Energy Transfer (TR-FRET) assay to screen for small molecule vFLIP inhibitors (FIGS. 7A-7D). This in vitro binding assay uses recombinant vFLIP and NEMO fusion protein linked to donor and acceptor fluorophores, respectively. The assay was sensitive and robust with a Z' value of 0.92 and is well-suited for high throughput screening of compound libraries. We screened a library of approximately 40,000 diverse and drug-like compounds and identified 20 hits with >40% inhibition which were validated with dose response curves (Table 3A).

TABLE 3A

| vFLIP/NEMO High-Throughput Small Molecule Screening Data Summary ||| 
|---|---|---|
| Category | Parameter | Description |
| Assay | Type of assay | Time Resolved Fluorescence Assay (TR-FRET) |
|  | Target | vFLIP/NEMO interaction |
|  | Primary measurement | Fluorescence emission at 620 nm for the donor |
|  | Key reagents | (Eu 3+ cryptate) and 665 nm for the XL665 acceptor |
|  | Assay protocol | Purified his-MBP vFLIP, biotinylated his-NEMO, anti-MBP- Eu cryptate (61MBPKAB,Cisbio) , Strepavidin XL665 (610SAXLB, Cisbio) |
|  | Additional comments | 20 µl final volume in low-volume white 384-well plate (Greiner biointernational): biotinylated his-NEMO and his-MBP vFLIP proteins were diluted to a working concentration (5x or 250 nM) in TR-FRET buffer (20 mM Tris pH = 7.5, 50 mM NaCl, 0.01% NP40, 0.5 mM TCEP, 0.1% BSA, 400 mM KF). The fluorophores anti-MBP-Eu cryptate and Strepavidin XL665 were diluted to a working concentration of (5x or 5 nM) and (5x or 200 nM) respectively. Order of addition: 4 µl/well of his-MBP vFLIP was added to the screening plate containing 4 µl of compound diluted in buffer. 5 minutes later, 4 µl/well of biotinylated his-NEMO or 4 µl/well of buffer (negative control: vFLIP only) was added and the plate was incubated for 15 min at RT. 8 µl of the mixed diluted fluorophores anti-MBP- Eu cryptate, and strepavidin XL665 were added to each well. The plate was spun down for 30 sec then incubated for 1 hr at RT. TR-FRET signal was detected using BioTek Synergy NEO To determine the optimal signal, titrations of both his-biotinylated NEMO and his-MBPvFLIP recombinant proteins and of the flurophores streptavidin-XL665 and the antibody-tagged fluorophore anti-MBPK labeled with Europium cryptate (Cisbio) were carried out. Optimal incubation time and DMSO tolerance were also determined |
| Libraries screened | Library size | 38,506 pure compounds |
|  | Library composition | Low molecular weight screening compounds |
|  | Source | LOP AC (Sigma, 1280 compounds), Enamine 3 (33,135 compounds), NIH clinical (727 compounds), HTRSC clinical (294 compounds), Prestwick (1109 compounds), Pharmakon (905 compounds). All compounds were dissolved in DMSO at 5 mM stock and stored at −28° C. |
|  | Additional comments | Library description www.rockefeller.edu/htsrc/libraries/ |
| Screen | Format | 384-well plate |
|  | Concentration tested | 12.5 µM, 0.2% DMSO |
|  | Plate controls | His-MBP vFLIP only (no NEMO, positive control), both His-MBP vFLIP and biotinylated his-NEMO (negative control) |
|  | Compounds/Reagents dispensing system | Janus Automated Workstation with Nanohead (Perkin Elmer) for compounds; MultiDrop Combi with RapidStack (Thermo Scientific) for reagents |
|  | Detection instrument | BioTek Synergy NEO multi-plate reader |
|  | Assay Validation/QC | Hit compounds were validated using dose-response titration (10 fold serial dilutions) in triplicates and a dose- response curve was fitted using CDD software. All confirmed hits were tested by HPLC-MS for purity and integrity |
|  | Normalization data | The TR-FRET signal or delta ratio was calculated as follows: Fluorscence of acceptor (665 nm)/ fluorescence of donor (620 nm) *10000 |

TABLE 3A-continued vFLIP/NEMO High-Throughput Small Molecule Screening Data Summary

| Category | Parameter | Description |
|---|---|---|
| | | Normalized percent inhibition (NPI) was calculated as the ratio of the sample to the positive control mean, after subtracting the background response, i.e. the negative control mean × 100 (NPI = (sample-mean of negative control)/(mean of positive control-mean of negative control) × 100. To evaluate the quality of the HTS TR-FRET assay, we calculated Z' factor which was determined to be 0.92. Z' was calculated according to the following formula: Z' = 1 − [3*(standard deviation positive control + standard deviation negative control)/(average positive control − average negative control)] |
| Post-HTS analysis | Hit criteria | Normalized percentage inhibition ≥ 30% |
| | Hit rate | 0.13% |
| | Additional assays | Cytotoxicity assay using CellTiter-Glo |
| | Confirmation of hit purity and integrity | All confirmed hits were retested using HPLC-MS and found to be at least 85% pure. Powders were ordered and retested in dose-response curves |

Of these compounds, nine with $IC_{50}$<65 μM were independently confirmed in the TR-FRET assay. Cytotoxicity of these hits was assayed using CellTiter Glo viability assay. Six of these compounds were active with $LC_{50}$ between 293 nM and 62 μM in KSHV-infected cell lines. However, none of these compounds had toxicity specific to PEL cells (BC-3), indicating toxicity due to vFLIP-independent mechanisms (Table 3B).

TABLE 3B

Top Nine Hits from the Small Molecule Screen Determined Using the TR-FRET Assay.

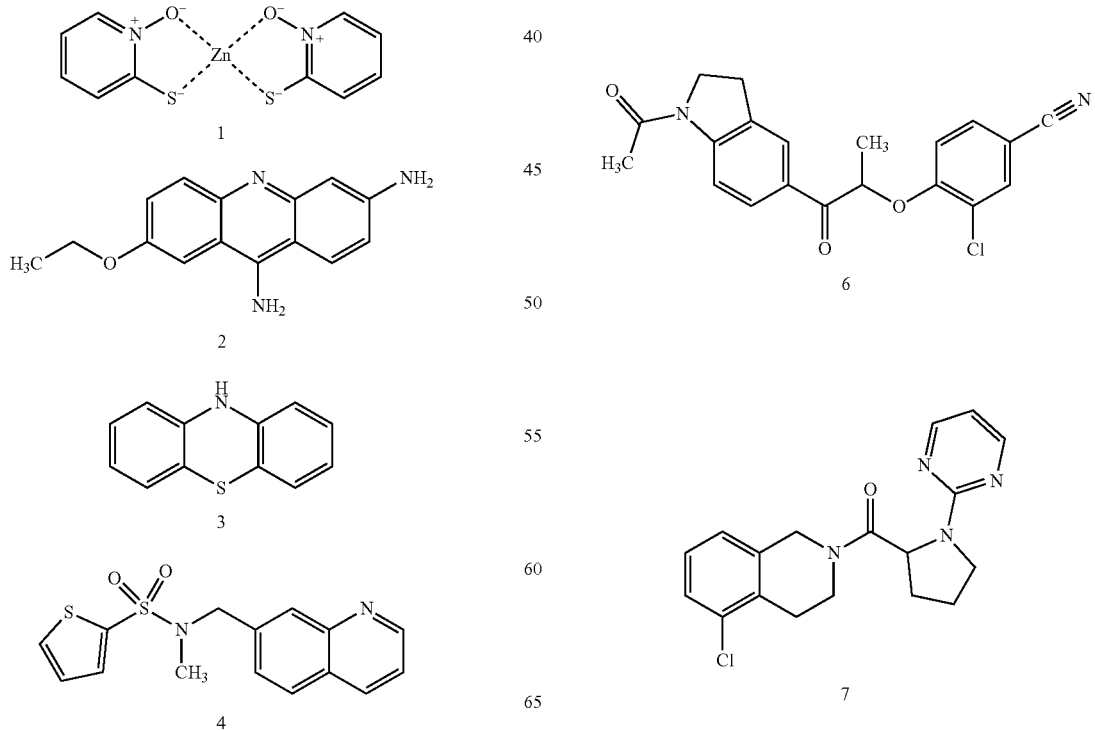

TABLE 3B-continued

TABLE 3B-continued

| Compound | TR-FRET IC$_{50}$ (µM) | BC-3 LC$_{50}$ (µM) | IBL-1 LC$_{50}$ (µM) |
|---|---|---|---|
| 1 | 40.2 | 0.30 | 0.3 |
| 2 | 53.0 | 12.2 | 7.7 |
| 3 | 51.9 | 62.7 | 63.0 |
| 4 | 23.7 | >100 | >100 |
| 5 | 61.3 | >100 | >100 |
| 6 | 61.9 | 35.9 | 69.7 |
| 7 | 55.7 | 39.9 | 31.6 |
| 8 | 37.8 | >100 | >100 |
| 9 | 20.1 | 3.9 | 3.8 |

Cytotoxic effect of the hits on cells that express vFLIP (BC3 PEL cell line) compared to a non-vFLIP expressing cell line (IBL-1 immunoblastic lymphoma cell line) was examined. Data shown is representative of three replicate experiments.

We next turned to a rational design approach to develop specific NEMO/vFLIP inhibitors. High resolution structures and computational alanine scanning (Kortemme et al., *Science STKE* 2004: p12 (2004), which is hereby incorporated by reference in its entirety) reveal residual contact from both helices of the NEMO parallel coiled coil; however, key hot spot residues primarily lie on Helix 2 of NEMO (Tyr234, His235, Phe238, Tyr241, Asp242, Ile245) as depicted in its helical wheel diagram (FIG. 2A) (Bagneris et al., *Mol. Cell* 30:620-31 (2008), which is hereby incorporated by reference in its entirety). To mimic the presentation of these hot spot residues, we designed linear and constrained peptides, that span the vFLIP binding region of NEMO (residues 232-245). We utilized the hydrogen bond surrogate (HBS) strategy to lock the peptide into the helical conformation (Sawyer et al., *Acc. Chem. Res.* 50:1313-22 (2017); Patgiri et al., *Acc. Chem. Res.* 41:1289-300 (2008), which are hereby incorporated by reference in their entirety). Unfortunately, neither the unconstrained (NEMO$^{232-245}$) or the HBS (HBS$^{NEMO}$) peptide inhibited the vFLIP-NEMO complex formation in the TR-FRET assay at 100 µM concentration (FIG. 8A-8B). At higher peptide concentrations, observable peptide aggregation is observed. The inefficient binding and low solubility of NEMO peptides and stabilized helices has also been observed in other studies (Briggs et al., *J. Virol.* 91 (2017), which is hereby incorporated by reference in its entirety).

Although one helix of the NEMO coiled coil engages vFLIP with stronger contacts, as suggested by the crystal structure of the complex (Bagneris et al., *Mol. Cell* 30:620-31 (2008), which is hereby incorporated by reference in its entirety) and the computational analysis, it was predicted that Helix 2 of NEMO is unable to properly orient itself on the vFLIP binding surface without the coiled coil partner. Based on this premise, the aim was to develop a NEMO coiled-coil mimic to modulate the target interaction. The coiled coil motif is not stable in short peptide sequences because short sequences do not offer enough interhelical contacts to enable formation of the dimeric assembly. We recently reported a strategy to generate synthetic coiled coil mimics, termed Crosslinked Helix Dimers (CHDs), by judiciously replacing an interhelical salt bridge with a covalent bond and sculpting optimal knob-into-hole helix packing (Wuo et al., *J. Am. Chem. Soc.* 137:11618-21 (2015), which is hereby incorporated by reference in its entirety). The optimized salt bridge surrogate and helix packing are required for high conformational stability. A parallel coiled coil mimic is optimal with e-g' position azidolysine residues crosslinked with propargyl ether using copper-catalyzed azide-alkyne cycloaddition (Meldal et al., *Chem. Rev.* 108: 2952-3015 (2008), which is hereby incorporated by reference in its entirety).

We attempted to develop a NEMO coiled coil mimic with native residues; however, the native sequence features non-optimal knob-into-hole helix packing (FIG. 2A) (Walshaw et al., *J. Struct. Biol.* 144:349-61 (2003), which is hereby incorporated by reference in its entirety). While imperfect packing can be tolerated in long coiled coils, synthetic mimics required us to mutate the helical interface to optimize conformational stability. Specifically, Tyr234 and Tyr241 were replaced with isoleucine residues and His244 mutated to leucine. Unfortunately, both tyrosine residues make critical contacts with the vFLIP surface (Table 4), which significantly diminished the binding affinity in the designed CHDs.

TABLE 4

Rosetta Computational Alanine Scanning Results for NEMO-vFLIP Structure (PDB: 3CL3)*.

| Residue | ΔΔG (R.E.U.) from 3CL3 |
|---|---|
| Q 231 | 0.94 |
| V 232 | — |
| A 233 | — |
| Y 234 | 2.77 |
| H 235 | 1.48 |
| Q 236 | — |
| L 237 | — |
| F 238 | 3.75 |
| Q 239 | 1.30 |
| E 240 | — |
| Y 241 | 1.18 |
| D 242 | 0.28 |
| N 243 | — |
| H 244 | — |
| I 245 | 1.03 |
| K 246 | 0.68 |

All hot spots were on Chain D from the PDB (Helix 2). Hot spot residues are highlighted in bold.
Rosetta Energy Unit (R.E.U.) is approximately 1 kcal/mol.
*Bagneris, C. et al. Crystal structure of a vFlip-IKKgamma complex: insights into viral activation of the IKK signalosome. Mol Cell 30, 620-31 (2008).

The failure of the CHDs bearing wild-type residues to provide potent inhibition prompted us to optimize the NEMO coiled coil with noncanonical residues to overcome the loss of the two tyrosine hot spot residues. We utilized AlphaSpace to obtain fragment-centric topographical mapping of protein surfaces to identify underutilized pockets in PPIs (Rooklin et al., *J. Chem. Inf. Model.* 55:1585-99 (2015), which is hereby incorporated by reference in its entirety). The topographical maps have proven useful in designing non-canonical residues to enhance target engagement (Rooklin et al., *J. Am. Chem. Soc.* 139:15560-63 (2017), which is hereby incorporated by reference in its entirety). We discovered several key pockets on the vFLIP surface that could be targeted using natural and non-natural amino acids displayed from the coiled-coil scaffold. AlphaSpace provides a pocket occupation score, which can be used as a guide to predict optimal noncanonical residues.

We utilized an iterative process of design, synthesis, biophysical and biological characterization to optimize NEMO coiled coil mimics. The sequences and TR-FRET derived inhibitory constants for each peptide are listed in FIG. 2B. A detailed discussion of the steps involved in optimization is included in Example 1 supra. Briefly, AlphaSpace predicted that incorporation of Lys246 to Arg246 mutation would increase occupancy of pocket iv from 45 to 75% (FIG. 2C). CHD1$^{NEMO}$ was synthesized to evaluate the effect of this modification while maintaining essential hot spot residues such as F238, which has a native pocket occupancy of 81% (pocket ii). In order to impart optimal interhelical packing, the interhelix residue Tyr234, which is a key hot spot residue, was mutated to Leu234. This mutation was compensated for by converting the neighboring Ala233 residue on Helix 1 to tryptophan. Typtophan is predicted to occupy 55% of pocket i. The native alanine residue did not engage this pocket. CHD2$^{NEMO}$ contains this change along with K246R. The highest-ranking underutilized pocket is detected near Helix/but is located too far from the NEMO backbone to be contacted by canonical amino acids. We derivatized Glu240 of Helix 1 with a cyclohexylamine group to obtain glutamine cycloxehyl amide ($Q^{Cy}$), and this substitution is predicted to provide 46% pocket occupancy (FIG. 2C). CHD3$^{NEMO}$ combines the earlier mutations with $Q^{Cy}$. AlphaSpace predicts that CHD3$^{NEMO}$ would be a high affinity ligand for vFLIP. We also designed and synthesized CHD4$^{NEMO}$ as a specificity control for CHD3$^{NEMO}$. CHD4$^{NEMO}$ contains alanines in place of one key hot spot residue on each helix at positions 233 of Helix 1 and 235 of Helix 2 (FIG. 2B).

The in vitro binding results support the computational predictions. CHD1$^{NEMO}$, CHD2$^{NEMO}$, and CHD4$^{NEMO}$ provided only partial inhibition of the vFLIP-NEMO complex at 100 μM concentrations (FIG. 3A); whereas CHD3$^{NEMO}$ led to robust inhibition of vFLIP-NEMO complex formation ($K_i$=6.9±1.4 μM). Under similar conditions, the wild-type NEMO coiled coil (NEMO$^{193-252}$) modulates the complex with a submicromolar inhibitory constant ($K_i$=0.39±0.10 μM). We also developed a fluorescence polarization binding assay to gauge the affinity of fluorescein-labeled derivative of CHD3$^{NEMO}$ for vFLIP. In this direct binding assay with the dye derivative, the $K_d$ of FITC-CHD3$^{NEMO}$ for vFLIP was calculated to be 240±70 nM (FIG. 3B). This NEMO mimic failed to bind wild-type NEMO coiled coil providing confidence that changes in the TR-FRET signal resulted from binding of the CHDs to vFLIP and not non-specific binding to NEMO.

Figure 9:
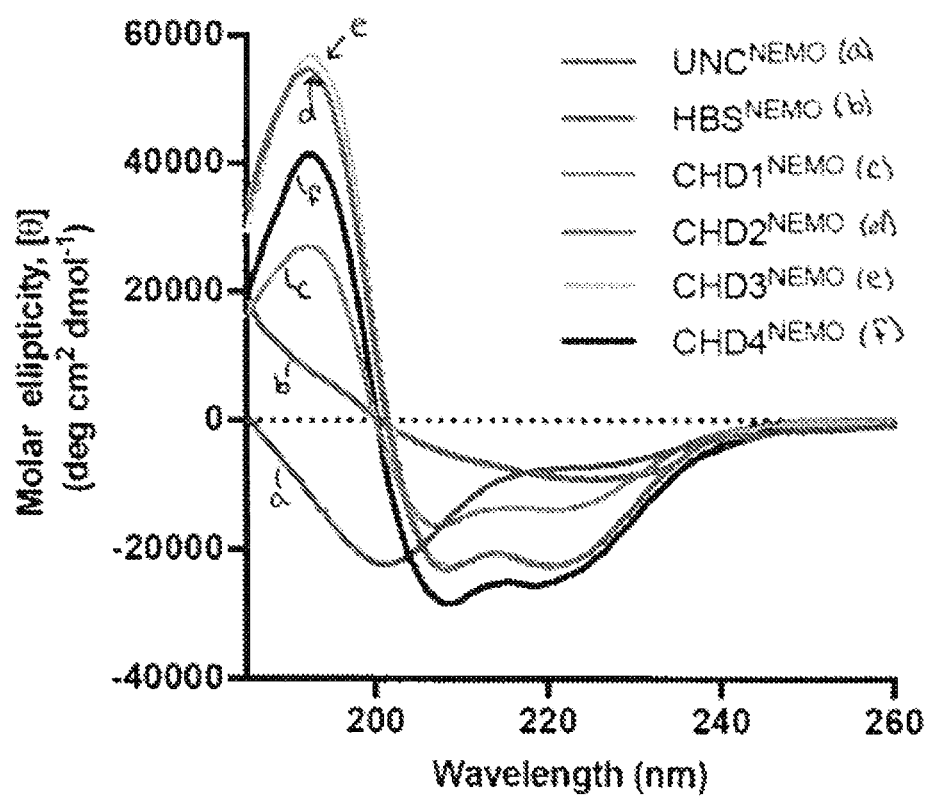
FIG. 9 shows the Circular Dichroism spectra of unconstrained, HBS, and CHD peptides. CD spectra of peptides were recorded in at 20 μM concentration in aqueous buffer: 50 mM KF pH 7.4. HBS$^{NEMO}$ (50 μM) contained buffer solution supplemented with 10% TFE. Data plotted is representative of two independent experiments.
Figure 10:
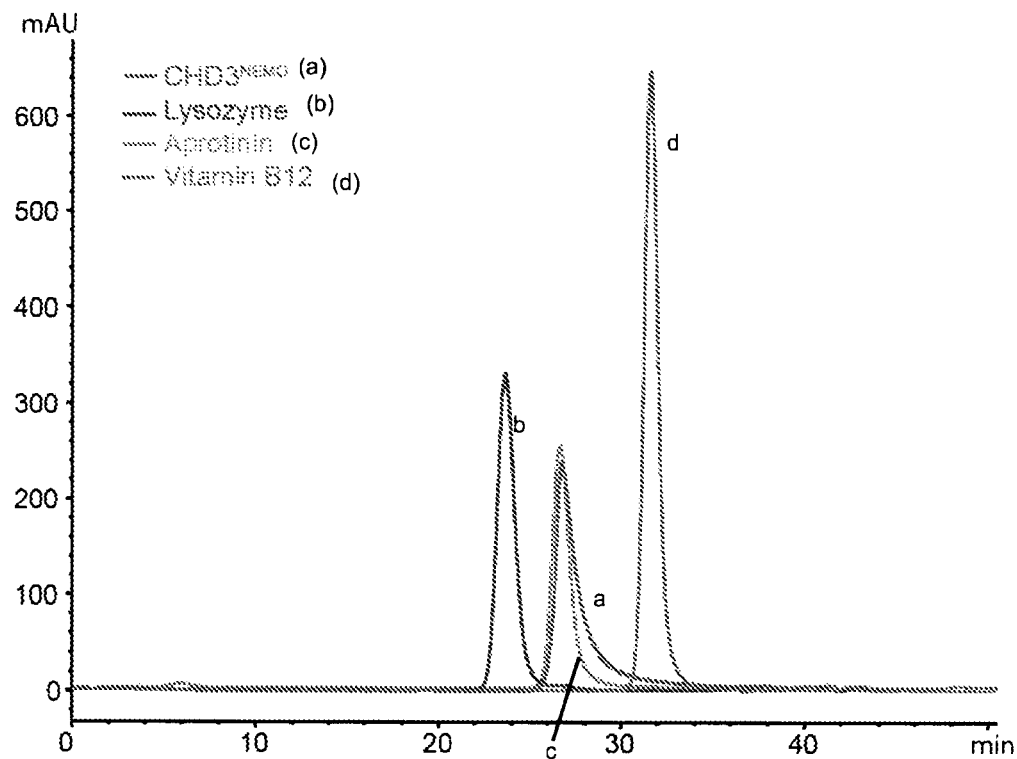
FIG. 10 shows the analytical size exclusion chromatography of CHD3$^{NEMO}$. Peptide standards lysozyme (14.3 kDa) and Aprotinin (6.5 kDa) and small molecule standard Vitamin B12 (1.4 kDa) are shown on the same plot. Solvent system: 2×PBS pH 7.4 10% Acetonitrile.

Together the three unoptimized CHDs (CHD1$^{NEMO}$, CHD2$^{NEMO}$, and CHD4$^{NEMO}$) highlight the role of the native and noncanonical hot spot residues in affording a potent designed ligand for vFLIP. We obtained circular dichroism spectra of the CHDs under aqueous buffers to gauge the impact of conformational stability on binding. Each mimetic shows a convincing alpha helical signature as demonstrated by local minima at 222 nm and 208 nm typical of coiled coils (FIG. 3C). Each CHD is highly helical, with the exception of CHD1$^{NEMO}$ (FIG. 9). Without being bound by theory, we predict that mutation of Asn243 to arginine results in an additional salt bridge aiding the helical stability of CHD2-4. Coiled coils have a tendency to multimerize or aggregate into larger assemblies. We utilized high performance size exclusion chromatography with appropriate protein molecular weight markers to determine if the CD signature of the mimics reflects constrained dimers, as designed, or higher order assemblies. This assay confirmed that CHD3$^{NEMO}$ does not aggregate in aqueous buffers (FIG. 10).

Example 3—CHD3$^{NEMO}$ Is Conformationally and Proteolytically Stable and Enters Live Cells Next, we analyzed the conformational stability of CHD3$^{NEMO}$ by monitoring changes in its circular dichroism spectrum as a function of temperature (FIG. 3D). We found the NEMO mimic to retain a significant proportion of helix percentage at high temperatures. We also probed the ability of CHD3$^{NEMO}$ to withstand serum proteases as a prelude to cellular assays. CHD3$^{NEMO}$ was observed to be highly resistant to degradation as roughly 80% of the initial peptide remained intact after 24 h of serum incubation (FIG. 3E). Together the thermal denaturation and serum stability assays reveal the high conformational and proteolytic stability of CHD3$^{NEMO}$.

Inhibition of the vFLIP-NEMO complex formation in KSHV-infected PEL cells requires the inhibitor to be cell permeable. Peptides often do not enter cells without exogenous delivery strategies or peptide modifications (Fujiwara et al., *Angew. Chem. Int. Ed. Engl.* 55:10612-5 (2016); Lian et al., *J. Am. Chem. Soc.* 136:9830-3 (2014); Bruce et al., *Cell Chem. Biol.* 24:924-34 (2017), which are hereby incorporated by reference in their entirety). We tested the ability of the fluorescein-derivatized coiled-coil mimic, FITC-CHD3$^{NEMO}$, to enter PEL cells using live cell confocal microscopy. We found that this compound enters BC-1 cells within 30 minutes; although not all cells had observable amounts of the fluorescein signal. Hoechst nuclear stain was employed in combination with FITC-CHD3$^{NEMO}$ and is shown as an overlay (FIG. 3F). In order to probe cellular entry mechanism, we performed cellular uptake experiments at 4° C. as well as with sodium azide poisoning to reduce ATP-mediated active transport mechanisms without affecting overall cellular viablity (Patgiri et al., *Nat. Chem. Biol.* 7:585-7 (2011); which is hereby incorporated by reference in its entirety). The reduction in cellular uptake at cold temperatures and in the presence of sodium azide suggests an active transport mechanism for CHD3$^{NEMO}$. We predict that the arginine-rich nature of CHD3$^{NEMO}$ is aiding its uptake (Nakase et al., *Mol. Ther.* 10:1011-22 (2004), which is hereby incorporated by reference in its entirety).

Example 4—CHD3$^{NEMO}$ Inhibits vFLIP-Mediated NF-κB Activation in a Dose-Dependent Manner The cellular uptake of CHD3$^{NEMO}$ provided impetus for further evaluation of this vFLIP ligand as modulator of cytosolic NEMO-vFLIP in cellular models. To probe the potential of NEMO mimetics to specifically engage vFLIP and modulate NF-κB transcriptional activity in PEL cells, we treated BC-3 NF-κB luciferase reporter cell line (BC-3-NF-κB-luc) with increasing doses of the CHD3$^{NEMO}$ or CHD4$^{NEMO}$ peptides (FIGS. 4A-B). NF-κB inhibitor Bay 11-7082 and HSP90 inhibitor PU—H71 were used as positive controls because the HSP90 chaperone is known to destabilize both vFLIP and NEMO (Nayar, et al., *Blood* 122:2837-47 (2013), which is hereby incorporated by reference in its entirety). We found that CHD3$^{NEMO}$ significantly inhibited NF-κB transcriptional activity in a dose-dependent manner both at t=5 h (FIG. 4A) and t=24 h (FIG. 4B) post-treatment in contrast to CHD4$^{NEMO}$, which showed minimal activity. Treatment of cells with 10 μM CHD3$^{NEMO}$ for 24 h led to 90 percent suppression of NF-κB activity as compared to 20 percent reduction with the same concentration of CHD4$^{NEMO}$, demonstrating the importance of critical hot spot residues in engaging vFLIP. This data suggests that CHD3$^{NEMO}$ can specifically engage vFLIP in PEL cells and modulate vFLIP-mediated activation of NF-κB signaling.

Example 5—CHD3$^{NEMO}$ Disrupts vFLIP/NEMO Complex Formation in Lymphoma Cells

Figure 11:
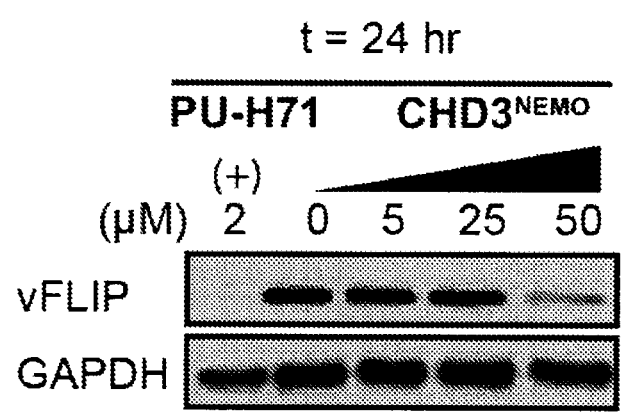
FIG. 11 is an image of a western blot showing that CHD3$^{NEMO}$ treatment downregulates vFLIP levels in BC1 PEL cells. The western blot using vFLIP rat $4C_1$ antibody shows that vFLIP protein levels decrease upon treatment with 50 μM dose of the CHD3$^{NEMO}$ peptide. The HSP90 inhibitor PU-H71 was used as a control since it destabilizes vFLIP levels. GAPDH was used as a gel loading control. Data shown is a representative of two independent experiments.

We next used co-immunoprecipitation studies to investigate whether the attenuation of NF-κB activity was a result of disrupting vFLIP/NEMO complex formation. Since currently available antibodies to vFLIP do not perform well in immunoprecipitation studies, we used a Namalwa Burkitt lymphoma cell line, which was stably transfected with the tetracycline-inducible FLAG-tagged wildtype (WT vFLIP) or mutant (Mut vFLIP) plasmid. We used Mut vFLIP as a positive control for vFLIP/NEMO complex disruption, since it is an NF-κB dead vFLIP that cannot engage intracellular NEMO. We induced expression of WT vFLIP or Mut vFLIP with doxycycline for 24 hrs. Following treatment, we dosed cells expressing wild-type vFLIP with DMSO or increasing concentrations of CHD3$^{NEMO}$ or CHD4$^{NEMO}$ peptides for an additional 24 hrs. Cells were lysed and immunoprecipitated using anti-FLAG antibody beads followed by immunoblot analysis using NEMO antibody (FIG. 4C). Treatment of cells with increasing concentrations of CHD3$^{NEMO}$ resulted in a dose-dependent disruption of the vFLIP/NEMO complex indicated by the reduced levels of NEMO that are pulled down by the FLAG beads. However, this was not the case when cells were treated with CHD4$^{NEMO}$. Interestingly, we observed overall low levels of vFLIP protein in the vFLIP NF-κB dead mutant control suggesting that NEMO binding is essential to stabilize vFLIP expression-consistent with earlier observations (Bagneris et al., Mol. Cell 30:620-31 (2008), which is hereby incorporated by reference in its entirety). Similarly, treating cells with the HSP90 inhibitor PU—H71 disrupted the complex and destabilized both vFLIP and NEMO, in agreement with the NF-κB reporter assay results. We observed similar reduction in vFLIP total protein levels upon treatment with CHD3$^{NEMO}$ as seen in the input blots and confirmed by western blot (FIG. 11). This data suggests that CHD3$^{NEMO}$ downregulates NF-κB activity by directly inhibiting the vFLIP/NEMO complex, and vFLIP protein stability is complex dependent.

Example 6—Designed Mimetics Show Selective Cytotoxicity Towards vFLIP Expressing Cell Lines To determine whether the inhibition of vFLIP-induced NF-κB activation in PEL cells was accompanied with cell death, we examined cytotoxicity of different NEMO mimetics in a panel of PEL cell lines (BC-1, BC-3, BCBL-1) and Namalwa cells, a Burkitt B-cell lymphoma cell line that does not express vFLIP. CHD3$^{NEMO}$ significantly decreased the cellular viability of BC-3 and BCBL-1 cells as early as t=24 h assessed using CellTiter-Glo assay that measures metabolic activity of cells. Significant killing of the BC-1 cell line that expresses higher levels of vFLIP protein occurred at t=48 h and t=72 h post-treatment. All PEL cell lines were sensitive to CHD3$^{NEMO}$ treatment (FIG. 5A), but PEL cells that expressed lower levels of vFLIP protein (Guasparri et al., J Exp Med 199:993-1003 (2004), which is hereby incorporated by reference in its entirety) (BC-3) were more sensitive to CHD3$^{NEMO}$ treatment (IC$_{50}$=5.8 μM). In addition, we found that PEL cells were relatively resistant to treatment with negative control peptide CHD4$^{NEMO}$ (FIG. 5A). Similar experiments conducted in vFLIP-negative Namalwa cells showed little to no sensitivity upon treatment with all three peptides. Both PEL and Namalwa cell lines showed sensitivity to PU—H71 (Table 5). Taken together, these data suggest that CHD3$^{NEMO}$ is selective to cells that express the vFLIP target and depend on this oncoprotein for cell survival.

TABLE 5

Panel of Lymphoma Cell Lines with Viral Status and Sensitivity to the HSP90 Inhibitor PU-H71 (Represented as LC$_{50}$ in Nanomolar Concentration).*±

| Cell line | Cell Type | PU-H71 LC$_{50}$ (nM) | Viral Status |
|---|---|---|---|
| BC-1 | PEL | 36.9 | KSHV$^+$/EBV$^+$ |
| BC-2 | PEL | 27.1 | KSHV$^+$/EBV$^+$ |
| BC-3 | PEL | 63.4 | KSHV$^+$ |
| BCBL-1 | PEL | 217 | KSHV$^+$ |
| Namalwa | Burkitt | 337.1 | EBV$^+$ |

*Nayar, U. et al. Targeting the Hsp90-associated viral oncoproteome in gammaherpesvirus-associated malignancies. Blood 122, 2837-47 (2013)
±Giulino-Roth, L. et al. Inhibition of Hsp90 Suppresses PI3K/AKT/mTOR Signaling and Has Antitumor Activity in Burkitt Lymphoma. Mol Cancer Ther 16, 1779-1790 (2017).

Example 7—CHD3$^{NEMO}$ Induces Apoptosis in BC-1 PEL Cell Line

To elucidate the mechanism of CHD3$^{NEMO}$ induced cell death, we performed Annexin V staining to detect whether PEL cells underwent apoptosis upon CHD3$^{NEMO}$ treatment (FIG. 5B). Annexin-V binds to phosphatidylserine (PS) that become exposed at the cell surface when cells undergo apoptosis. We treated BC-1 (FIG. 5B, left) or Namalwa cells (FIG. 5B, right) with DMSO or increasing concentrations of CHD3$^{NEMO}$ or CHD4$^{NEMO}$ under serum-starved conditions subsequently supplemented with 20% FBS one hour post-treatment. Cells were treated with peptides for t=24 h or t=48 h after which cells were stained with Annexin V and DAPI and analyzed by flow cytometry for cell death. We observed a significant increase in early apoptotic cells (Annexin V positive, p<0.05) in cells treated with 25 μM CHD3$^{NEMO}$ compared to DMSO (FIG. 5C) as early as t=24 h post-treatment and this increase was more prominent at t=48 h (FIG. 5B). Cells treated with 50 μM dose showed a significant increase in Annexin V/DAPI double positive and single DAPI positive cells indicating late apoptosis. However, we did not detect any apoptosis upon treating BC-1 cells with CHD4$^{NEMO}$ or in the control non-PEL Namalwa cell line. Collectively, these data suggest that CHD3$^{NEMO}$ treatment inhibits NF-κB and selectively promotes apoptosis in vFLIP-expressing PEL cell lines.

Example 8—In Vivo Assessment of CHDs in a PEL Xenograft Murine Model

The above results suggest that CHD3$^{NEMO}$ is highly efficacious in cellular assays. We next tested its antitumor activity in vivo. We injected 10×10$^6$ BC-3-luc PEL cells into the peritoneal cavity of NOD-SCID mice and monitored tumor burden by bioluminescence imaging. After tumor engraftment, mice were randomized, and were treated with vehicle alone (n=10) or with 20 mg/kg of CHD3$^{NEMO}$ (n=5)

for 9 consecutive days. All mice in the control arm showed clear tumor growth, however mice in the treated group showed a remarkable delay in tumor growth without any observed toxicity (FIGS. 6A-6B, p<0.05 at day 20). Moreover, Kaplan-Meier analysis showed that mice treated with CHD3$^{NEMO}$ had a significant survival advantage compared to the control group (FIG. 6C, p<0.05).

Discussion of Examples 1-8

The topological complexity of NEMO-mediated protein-protein interactions underscores the difficulty in identifying small molecule leads or short peptides. The NEMO protein is characterized by a large and flat binding surface containing dispersed critical binding residues over a long coiled coil architecture (Johnson et al., *J. Am. Chem. Soc.* 133:10038-41 (2011), which is hereby incorporated by reference in its entirety). We rationally designed a potent NEMO coiled coil mimetic, CHD3$^{NEMO}$, to bind viral oncoprotein vFLIP and disrupt its role in the pathogenesis of PEL. These studies demonstrate the potential of CHD molecules to replicate the complex binding mode of NEMO and inhibit its central role in NF-κB signaling. We evaluated the ability of the computationally-optimized ligand to engage intracellular vFLIP using biophysical and biochemical assays, and demonstrated the compound's efficacy using cellular assays and an in vivo experimental animal model. CHD3$^{NEMO}$ reduces vFLIP-mediated NF-κB transcriptional activity and disrupts the NEMO-vFLIP complex in competitive pull-down assays. Our results indicate that CHD3$^{NEMO}$-induced cytotoxicity occurs through programmed cell death, which in turn supports the premise that NEMO-vFLIP complex inhibition is critical to reducing NF-κB activity and regulating genes that encode anti-apoptotic proteins involved in cell survival. Importantly, the activity of the designed ligand is sequence selective as a closely related alanine mutant, CHD4$^{NEMO}$ had a diminished effect on NF-κB activation, underscoring the specificity imparted by the designed hot spot residues. Coiled coil-mediated protein interactions often display complex epitopes suggesting that the CHD strategy may prove useful in targeting this intractable class of interactions (Watkins et al., *J. Am. Chem. Soc.* 137:11622-30 (2015), which is hereby incorporated by reference in its entirety).

The in vivo efficacy of CHD3$^{NEMO}$ was determined using a vFLIP-driven PEL xenograft model derived from BC-3 cells. Intraperitoneal injections of CHD3$^{NEMO}$ significantly reduced tumor volume and granted survival advantage over the untreated group without any observed toxicity. The tumor growth reduction demonstrated by CHD3$^{NEMO}$ supports our expectation that the complex binding epitope of coiled coils can be mimicked using CHDs, and targeting the NEMO-vFLIP interaction is a promising approach for treating KSHV$^+$-associated lymphomas and likely other KSHV-associated diseases, such as KS, that also express vFLIP. The present strategy offers a proof-of-principle for targeting complex intracellular protein-protein interactions as well as the first lead compound to have activity in the experimental disease model.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of inhibiting interaction between NEMO and a target molecule that binds to a helix dimer consisting of HLX1 and HLX2 of NEMO, said method comprising:

contacting NEMO and/or the target molecule with a macrostructure comprising a parallel coiled-coil selected from the group consisting of CHD1$^{NEMO}$, CHD2$^{NEMO}$, CHD3$^{NEMO}$, and CHD4$^{NEMO}$ under conditions effective to inhibit interaction between NEMO and the target molecule, wherein the target molecule is vFLIP.

2. The method of claim 1, wherein said contacting is carried out in vivo.

3. The method of claim 1, wherein said contacting is carried out in a cell.

4. The method of claim 1, wherein said contacting is carried out in a subject.

5. The method of claim 3, wherein said contacting induces apoptosis of the cell, inhibits proliferation of the cell, and/or inhibits NFκB translocation in the cell.

6. The method of claim 3, wherein the cells are mammalian cells.

7. The method of claim 3, wherein the cells are primate cells.

8. The method of claim 3, wherein the cells are lymphoma cells or Kaposi sarcoma ("KS") cells.

9. The method of claim 1, wherein the method is carried out in a subject.

10. The method of claim 1, wherein the macrostructure comprising the parallel coiled-coil is CHD3$^{NEMO}$.

* * * * *